US012486333B2

(12) United States Patent
Keith, Jr. et al.

(10) Patent No.: US 12,486,333 B2
(45) Date of Patent: Dec. 2, 2025

(54) TISSUE PLASMINOGEN ACTIVATOR ANTIBODIES AND METHOD OF USE THEREOF

(71) Applicant: EMSTOPA LIMITED, Sandwich (GB)

(72) Inventors: James Carl Keith, Jr., Andover, MA (US); Alexander Noel Fraser Brown, Stevenage (GB); Preeti Bakrania, Stevenage (GB)

(73) Assignee: EMSTOPA LIMITED, Sandwich (GB)

( * ) Notice: Subject to any disclaimer, the term of this patent is extended or adjusted under 35 U.S.C. 154(b) by 1241 days.

(21) Appl. No.: 17/292,883

(22) PCT Filed: Nov. 13, 2019

(86) PCT No.: PCT/EP2019/081225
§ 371 (c)(1),
(2) Date: May 11, 2021

(87) PCT Pub. No.: WO2020/099508
PCT Pub. Date: May 22, 2020

(65) Prior Publication Data

US 2021/0395393 A1 Dec. 23, 2021

(30) Foreign Application Priority Data

Nov. 13, 2018 (GB) ..................................... 1818477

(51) Int. Cl.

| | |
|---|---|
| ***C07K 16/40*** | (2006.01) |
| ***A61K 39/00*** | (2006.01) |
| ***A61P 7/02*** | (2006.01) |

(52) U.S. Cl.
CPC ................ *C07K 16/40* (2013.01); *A61P 7/02* (2018.01); *A61K 2039/505* (2013.01); *C07K 2317/24* (2013.01); *C07K 2317/76* (2013.01); *C07K 2317/94* (2013.01)

(58) Field of Classification Search
CPC ................ C07K 16/40; C07K 2317/24; C07K 2317/76; C07K 2317/94; A61P 7/02; A61K 2039/505
See application file for complete search history.

(56) References Cited

U.S. PATENT DOCUMENTS

| | | | |
|---|---|---|---|
| 4,816,567 | A | 3/1989 | Cabilly et al. |
| 5,641,870 | A | 6/1997 | Rinderknecht et al. |
| 2015/0353647 | A1 | 12/2015 | Reed |

FOREIGN PATENT DOCUMENTS

| | | | |
|---|---|---|---|
| WO | WO 88/01649 | A1 | 3/1988 |
| WO | WO 90/05144 | A1 | 5/1990 |
| WO | WO 91/17271 | A1 | 11/1991 |
| WO | WO 94/04678 | A1 | 3/1994 |
| WO | WO 94/13804 | A1 | 6/1994 |
| WO | WO 94/29348 | A2 | 12/1994 |
| WO | WO 98/25971 | A1 | 6/1998 |
| WO | WO 98/48837 | A1 | 11/1998 |
| WO | WO 01/79258 | A1 | 10/2001 |
| WO | WO 02/056910 | A1 | 7/2002 |
| WO | WO 03/050531 | A2 | 6/2003 |
| WO | WO 2004/003019 | A2 | 1/2004 |
| WO | WO 2004/041865 | A2 | 5/2004 |
| WO | WO 2004/081026 | A2 | 9/2004 |
| WO | WO 2014/116706 | A1 | 7/2014 |

OTHER PUBLICATIONS

Barber et al., "D-Dimer Predicts Early Clinical Progression in Ischemic Stroke: Confirmation Using Routine Clinical Assays," *Stroke* 37: 1113-1115 (2006).
Burtet et al., "Production of a Recombinant Fab in Pichia pastoris from a Monocistronic Expression Vector," J. Biochem 142(6): 665-669 (2007).
Cajot et al., "Monoclonal antibodies directed against human tissue-type plasminogen activator: a characterization of their species specificity, affinity and heavy-chain binding," *Thrombosis Research* 46(1): 141-152 (1987).
Cardenas et al., "Elevated Tissue Plasminogen Activator and Reduced Plasminogen Activator Inhibitor Promote Hyperfibrinolysis in Trauma Patients," *Shock* 41(6): 514-521 (2014).
Carmen et al., "Concepts in antibody phage display," Briefings in Functional Genomics and Proteomics 1(2): 189-203 (2002).
Chapman et al., "Overwhelming tPA Release, not PAI-1 Degradation, is Responsible for Hyperfibrinolysis in Severely Injured Trauma Patients," *J Trauma Acute Care Surg*. 80(1): 16-25 (2016).
Database Medline, US National Library of Medicine, Ball et al., "Selection of monoclonal antibodies that bind and inhibit tissue-type plasminogen activator," Accession No. NLM8359825 (1993).
Donnan et al., "How to make better use of thrombolytic therapy in acute ischemic stroke," *Nat Rev Neural*. 7: 400-409 (2011).
Duque et al., "Pathophysiological Response to Trauma-Induced Coagulopathy: A Comprehensive Review," *Anesth Analg* 130(3): 654-664 (2020).
Fergusson et al., "A comparison of aprotinin and lysine analogues in high-risk cardiac surgery," *New England Journal of Medicine* 358(22): 2319-2331 (2008).
Gebhardt et al., "Fibrinolysis in patients with mild-to-moderate bleeding tendency or unknown cause," *Ann Hematol* 96: 489-495 (2017).

(Continued)

*Primary Examiner* — Jeffrey Stucker
*Assistant Examiner* — Brittney E Donoghue
(74) *Attorney, Agent, or Firm* — Leydig, Voit & Mayer, Ltd.

(57) ABSTRACT

The present invention provides tissue plasminogen activator antibody molecules and their uses. More particularly, the presently-disclosed invention provides humanised antibody molecules which specifically bind tissue plasminogen activator (TPA) and their use in treating TPA induced haemorrhage, in particular treating systemic haemorrhage such as brain haemorrhage after treatment of ischemic stroke or myocardial infarction, or systemic bleeding after TPA treatment of pulmonary embolism, ischemic stroke or myocardial infarction.

19 Claims, 38 Drawing Sheets

Specification includes a Sequence Listing.

(56) References Cited

OTHER PUBLICATIONS

Holliger et al., "Diabodies: small bivalent and bispecific antibody fragments," *Proc Natl Acad Sci USA* 90(14): 6444-6448 (1993).
Huston et al., "Medical Applications of Single-Chain Antibodies," International Reviews of Immunology 10(2-3): 195-217 (1993).
Khan et al., "Severely Injured Trauma Patients With Admission Hyperfibrinolysis; Is There a Role of Tranexemic Acid? Findings From the PROPPR Trial," *J Trauma Acute Care Surg* 85(5): 851-857 (2018).
Kizhedath et al., "Applicability of predictive toxicology methods for monoclonal antibody therapeutics: status Quo and scope," *Arch Toxicol* 91(4): 1595-1612 (2017).
Knappik et al., "Fully synthetic human combinatorial antibody libraries (HuCAL) based on modular consensus frameworks and CDRs randomized with trinucleotides," *J Mol Biol* 296(1): 57-86 (2000).
Leiper et al., "Tissue plasminogen activator, plasminogen activator inhibitors, and activator-inhibitor complex in liver disease," *J Clin Pathol* 47: 214-217 (1994).
Longstaff et al., "A proposed reference method for plasminogen activators that enables calculation of enzyme activities in SI units," *J Thromb Haemost* 2(8): 1416-1421 (2004).
Manji et al., "Seizures following cardiac surgery: the impact of tranexamic acid and other risk factors," *Can J Anesth* 59: 6-13 (2012).
Matsuo et al., "Monoclonal antibody to human tissue plasminogen activator," *Thrombosis Research* 36(6): 517-526 (1984).
Morgenstern et al., "Guidelines for the Management of Spontaneous Intracerebral Hemorrhage: A Guideline for Healthcare Professionals From the American Heart Association/American Stroke Association," *Stroke* 41(9): 2108-2129 (2010).
Morrison et al., "Chimeric human antibody molecules: Mouse antigen-binding domains with human constant region domains," *Proc Natl Acad Sci USA* 81(21): 6851-6855 (1984).
Munoz et al., "Is ε-Aminocaproic Acid as Effective as Aprotinin in Reducing Bleeding With Cardiac Surgery? A Meta-Analysis," *Circulation* 99: 81-89 (1999).
Nelson et al., "Demystified: Monoclonal antibodies," *J Clin Pathol: Mol Pathol* 53: 111-117 (2000).
Riechmann et al., "Reshaping human antibodies for therapy," *Nature* 332(6162): 323-327 (1988).
Rippmann et al., "Procaryotic Expression of Single-Chain Variable-Fragment (scFv) Antibodies: Secretion in L-Form Cells of Proteus mirabilis Leads to Active Product and Overcomes the Limitations of Periplasmic Expression in *Escherichia coli," Applied and Environmental Microbiology* 64(12): 4862-4869 (1998).
Rønning et al., "Tenecteplase Versus Alteplase Between 3 and 4.5 Hours in Low National Institutes of Health Stroke Scale," *Stroke* 50(2): 498-500 (2019).
Saver, "Hemorrhage After Thrombolytic Therapy for Stroke. The Clinically Relevant Number Needed to Harm," *Stroke* 38(8): 2279-2283 (2007).
Sazonova et al., "Reprogrammed streptokinases develop fibrin-targeting and dissolve blood clots with more potency than tissue plasminogen activator," *J Thromb Haemost* 7(8): 1321-1328 (2009).
Su et al., "Activation of PDGF-CC by Tissue Plasminogen Activator Impairs Blood Brain Barrier Integrity During Ischemic Stroke," *Nat Med* 14(7): 731-737 (2008).
Swanson et al., "A Semiautomated Method for Measuring Brain Infarct Volume," *J Cereb Blood Flow Metab* 10(2): 290-293 (1990).
World Health Organization, Expert Committee on Biological Standardization (WHO/BS/07.2068), Geneva, Oct. 8-12, 2007 (37 pgs.).
Willems et al., "Optimizing expression and purification from cell culture medium of trispecific recombinant antibody derivatives," *J Chromatogr B* 786(1-2): 161-176 (2003).
Xu et al., "Different doses of tenecteplase vs alteplase in thrombolysis therapy of acute ischemic stroke: evidence from randomized controlled trials," *Drug Des Devel Ther* 12: 2071-2084 (2018).
European Patent Office, International Search Report in International Application No. PCT/EP2019/081225 (Mar. 9, 2020).
European Patent Office, Written Opinion in International Application No. PCT/EP2019/081225 (Mar. 9, 2020).
International Bureau of WIPO, International Preliminary Report on Patentability in International Application No. PCT/EP2019/081225 (May 18, 2021).
Ball et al., "Selection of monoclonal antibodies that bind and inhibit tissue-type plasminogen activator," *Hybridoma* 12(3): 317-326 (2009).
Bayes-Genis et al., "D-Dimer is an early diagnostic marker of coronary ischemia in patients with chest pain," *Am Heart J* 140(3): 379-384 (2000).
Eberle et al., "Clinical update on thrombolytic use in pulmonary embolism: A focus on intermediate-risk patients," *Am J Health-Syst Pharma* 75: 1275-1285 (2018).
Gupta et al., "Safety and outcomes of thrombolysis with tissue plasminogen activator for treatment of intravascular thrombosis in children," *J Pediatr*. 139(5): 682-688 (2001).
Gurwitz et al., "Risk for intracranial haemorrhage after tissue plasminogen activator treatment for acute myocardial infarction. Participants in the National Registry of Myocardial Infarction 2," *Ann Intern Med*. 129(8): 597-604 (1998).
James et al., "Predictors of symptomatic intracranial haemorrhage in patients with an ischaemic stroke with neurological deterioration after intravenous thrombolysis," *J Neurol Neurosurg Psychiatry* 89(8): 866-869 (2018).

Figure 1: PCR primers for amplifying mouse VK

| Name | Sequence (5' → 3') | |
|---|---|---|
| MKV1 | *TGTAAAACGACGGCCAGT*ATGAAGTTGCCTGTTAGGCTGTTGGTGCTG | SEQ ID No 43 |
| MKV2 | *TGTAAAACGACGGCCAGT*ATGGAGWCAGACACACTCCTGYTATGGGTG | SEQ ID No 44 |
| MKV3 | *TGTAAAACGACGGCCAGT*ATGAGTGTGCTCACTCAGGTCCTGGSGTTG | SEQ ID No 45 |
| MKV4 | *TGTAAAACGACGGCCAGT*ATGAGGRCCCCTGCTCAGWTTYTTGGMWTCTTG | SEQ ID No 46 |
| MKV5 | *TGTAAAACGACGGCCAGT*ATGGATTTWAGGTGCAGATTWTCAGCTTC | SEQ ID No 47 |
| MKV6 | *TGTAAAACGACGGCCAGT*ATGAGGTKCKKTGKTSAGSTSCTGRGG | SEQ ID No 48 |
| MKV7 | *TGTAAAACGACGGCCAGT*ATGGGCWTCAAGATGGAGTCACAKWYYCWGG | SEQ ID No 49 |
| MKV8 | *TGTAAAACGACGGCCAGT*ATGTGGGGAYCTKTTTYCMMTTTTTCAATTG | SEQ ID No 50 |
| MKV9 | *TGTAAAACGACGGCCAGT*ATGGTRTCCWCASCTCAGTTCCTTG | SEQ ID No 51 |
| MKV10 | *TGTAAAACGACGGCCAGT*ATGTATATATGTTTGTTGTCTATTTCT | SEQ ID No 52 |
| MKV11 | *TGTAAAACGACGGCCAGT*ATGGAAGCCCCAGCTCAGCTTCTCTTCC | SEQ ID No 53 |
| CL12A | *TGTAAAACGACGGCCAGT*ATGRAGTYWCAGACCCAGGTCTTYRT | SEQ ID No 54 |
| CL12B | *TGTAAAACGACGGCCAGT*ATGGAGACACATTCTCAGGTCTTTGT | SEQ ID No 55 |
| CL13 | *TGTAAAACGACGGCCAGT*ATGGATTCACAGGCCCAGGTTCTTAT | SEQ ID No 56 |
| CL14 | *TGTAAAACGACGGCCAGT*ATGATGAGTCCTGCCCAGTTCCTGTT | SEQ ID No 57 |
| CL15 | *TGTAAAACGACGGCCAGT*ATGAATTTGCCTGTTCATCTCTTGGTGCT | SEQ ID No 58 |
| CL16 | *TGTAAAACGACGGCCAGT*ATGGATTTTCAATTGGTCCTCATCTCCTT | SEQ ID No 59 |
| CL17A | *TGTAAAACGACGGCCAGT*ATGAGGTGCCTARCTSAGTTCCTGRG | SEQ ID No 60 |
| CL17B | *TGTAAAACGACGGCCAGT*ATGAAGTACTCTGCTCAGTTTCTAGG | SEQ ID No 61 |
| CL17C | *TGTAAAACGACGGCCAGT*ATGAGGCATTCTCTTCAATTCTTGGG | SEQ ID No 62 |
| MKC | *CAGGAAACAGCTATGACC*ACTGGATGGTGGGAAGATGG | SEQ ID No 63 |

Ambiguity codes: W = A or T; Y = C or T; K = G or T

MKV indicates primer that hybridizes to leader sequences of the mouse kappa light chain variable region genes; MKC indicates the primer that hybridizes to the mouse kappa constant region gene. Italicised section indicates the M13 Forward or the M13 Reverse Sequencing Primer. Wobble bases are defined in Abbreviations.

Figure 2: PCR primers for amplifying mouse VH

| Name | Sequence (5' → 3') | |
|---|---|---|
| MHV1 | *TGTAAAACGACGGCCAGT*ATGAAATGCAGCTGGGGCATSTTCTTC | SEQ ID No 64 |
| MHV2 | *TGTAAAACGACGGCCAGT*ATGGGATGGAGCTRTATCATSYTCTT | SEQ ID No 65 |
| MHV3 | *TGTAAAACGACGGCCAGT*ATGAAGWTGTGGTTAAACTGGGTTTTT | SEQ ID No 66 |
| MHV4 | *TGTAAAACGACGGCCAGT*ATGRACTTTGGGYTCAGCTTGRTTT | SEQ ID No 67 |
| MHV5 | *TGTAAAACGACGGCCAGT*ATGGACTCCAGGCTCAATTTAGTTTTCCTT | SEQ ID No 68 |
| MHV6 | *TGTAAAACGACGGCCAGT*ATGGCTGTCYTRGSGCTRCTCTTCTGC | SEQ ID No 69 |
| MHV7 | *TGTAAAACGACGGCCAGT*ATGGRATGGAGCKGGRTCTTTMTCTT | SEQ ID No 70 |
| MHV8 | *TGTAAAACGACGGCCAGT*ATGAGAGTGCTGATTCTTTTGTG | SEQ ID No 71 |
| MHV9 | *TGTAAAACGACGGCCAGT*ATGGMTTGGGTGTGGAMCTTGCTATTCCTG | SEQ ID No 72 |
| MHV10 | *TGTAAAACGACGGCCAGT*ATGGGCAGACTTACATTCTCATTCCTG | SEQ ID No 73 |
| MHV11 | *TGTAAAACGACGGCCAGT*ATGGATTTTGGGCTGATTTTTTTTATTG | SEQ ID No 74 |
| MHV12 | *TGTAAAACGACGGCCAGT*ATGATGGTGTTAAGTCTTCTGTACCTG | SEQ ID No 75 |
| MHCG1 | *CAGGAAACAGCTATGACC*CAGTGGATAGACAGATGGGGG | SEQ ID No 76 |
| MHCG2a | *CAGGAAACAGCTATGACC*CAGTGGATAGACCGATGGGGC | SEQ ID No 77 |
| MHCG2b | *CAGGAAACAGCTATGACC*CAGTGGATAGACTGATGGGGG | SEQ ID No 78 |
| MHCG3 | *CAGGAAACAGCTATGACC*CAAGGGATAGACAGATGGGGC | SEQ ID No 79 |

Ambiguity codes: R = A or G; K = G or T; M = A or C

MHV indicates primers that hybridize to the leader sequences of mouse heavy chain variable region genes, MHCG indicates primers that hybridize to the mouse constant region genes. Italicized section indicates the M13 Forward or the M13 Reverse Sequencing Primer. Primer MHCmix consists of an equimolar mix of primers MHCG1, MHCG2a, MHCG2b and MHCG3. 'Wobble' bases are defined in Abbreviations Figure 3: General PCR and sequencing primers

| Name | Sequence (5' → 3') | |
|---|---|---|
| HCMVi promotor Forward | TGT TCC TTT CCA TGG GTC TT | SEQ ID No 80 |
| HuG1 LIC Rev | GCC GGA GGT GGA CTT GGA GG | SEQ ID No 81 |
| HuK LIC Rev | GCA GTT CCA GAT TTC AAC TG | SEQ ID No 82 |
| E1_alpha_rev | GAC CGT TCT TCC ACC ACT GAT TA | SEQ ID No 83 |
| M13-Forward | TGT AAA ACG ACG GCC AGT | SEQ ID No 84 |
| M13-Reverse | CAG GAA ACA GCT ATG ACC | SEQ ID No 85 |

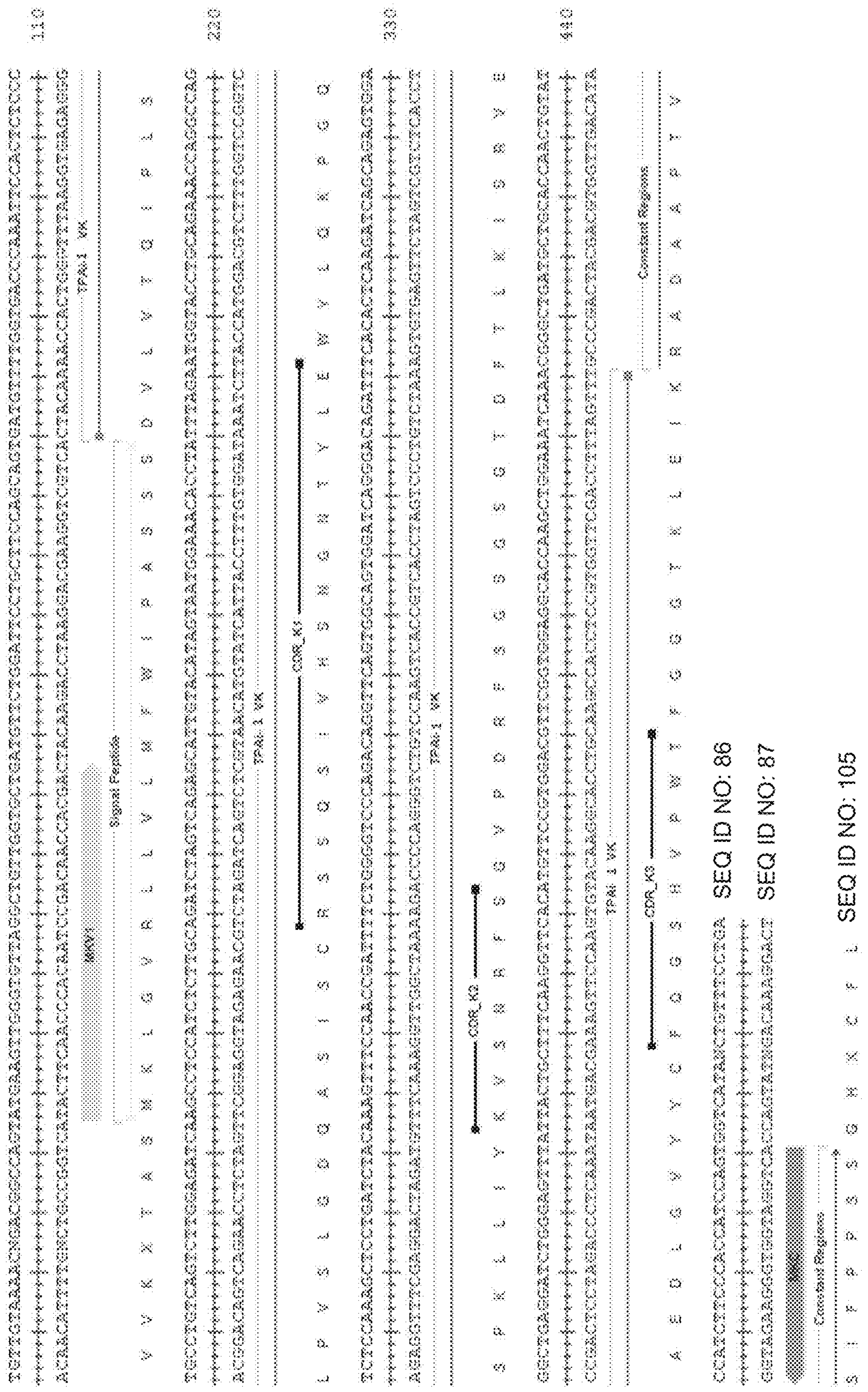
Figure 4: Protein and DNA sequence of TPAi-1 Kappa Light Chain Variable Region Figure 5: Protein and DNA sequence of TPAi-1 Heavy Chain Variable Region
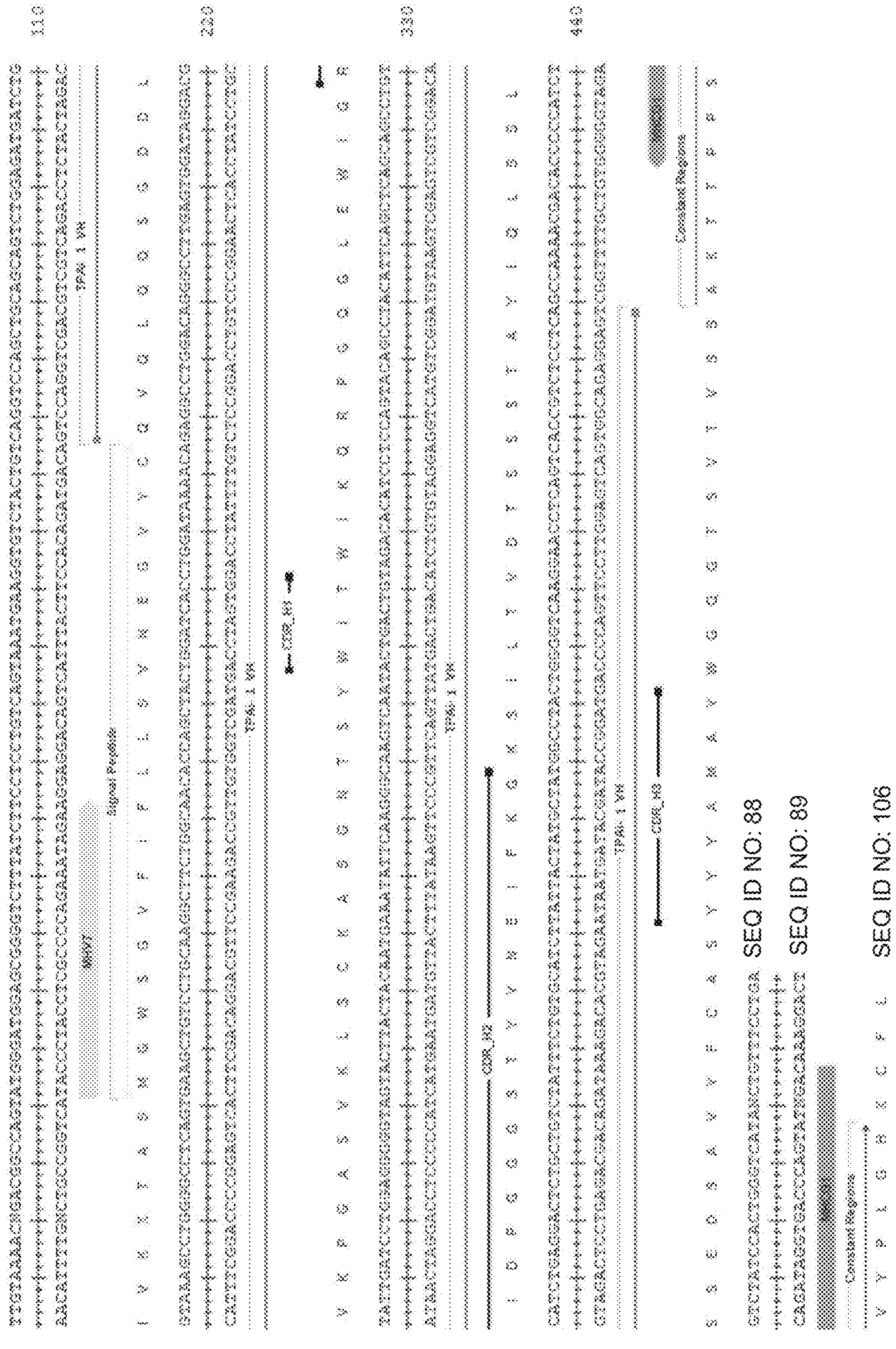

Figure 6: TPAi-1 Kappa Light Chain Germ Line Analysis SEQ ID NO: 90 and SEQ ID NO: 107

| Species | Gene and allele | Score | % identity |
|---|---|---|---|
| Mus musculus | IGKV1-117*01 | 658 | 98.0 |
| Mus musculus | IGKV1-117*02 | 638 | 95.0 |
| Mus musculus | IGKV1-110*02 | 633 | 92.0 |
| Mus musculus | IGKV1-110*01 | 619 | 91.0 |
| Rattus norvegicus | IGKV1S25*01 | 607 | 87.0 |

```
             ----------+---------+---------+---------+---------+---------+---------+---------+---------+----------
             1        10        20        30        40        50        60        70        80        90
             ----------+---------+---------+---------+---------+---------+---------+---------+---------+----------
IGKV1-117*01 DVLMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVP
TPAi-1_MKV1  ...V..I.............................................................................................
```

Figure 7: TPAi-1 Heavy Chain Germ Line Analysis SEQ ID NO: 91 and SEQ ID NO: 108

| Species | Gene and allele | score | % identity |
|---|---|---|---|
| Mus musculus | IGHV1S132*01 | 515 | 80.4 |
| Mus musculus | IGHV1-55*01 | 511 | 80.4 |
| Mus musculus | IGHV1-75*01 | 498 | 79.4 |
| Mus musculus | IGHV1S12*01 | 493 | 79.4 |
| Mus musculus | IGHV1-85*01 | 493 | 79.4 |

```
              ----------+---------+---------+---------+---------+---------+---------+---------+---------+----------
              1        10        20        30        40        50        60        70        80        90
              ----------+---------+---------+---------+---------+---------+---------+---------+---------+----------
IGHV1S132*01  QVQLQQSGAELVKPGASVKLSCKTSGYTFTSYWIQWVKQRPGQGLGWIGEIFPGTGTTYYNEKFKGKATLTIDTSSSTAYMQLSSLTSEDSAVYFCAR
TPAi-1  MHV7  ........ED..............ASG~N~.....T.I........E...R.D..G.S.....I....SI..V........I.....S..........S
```

Figure 8: pHuG1 LIC vector
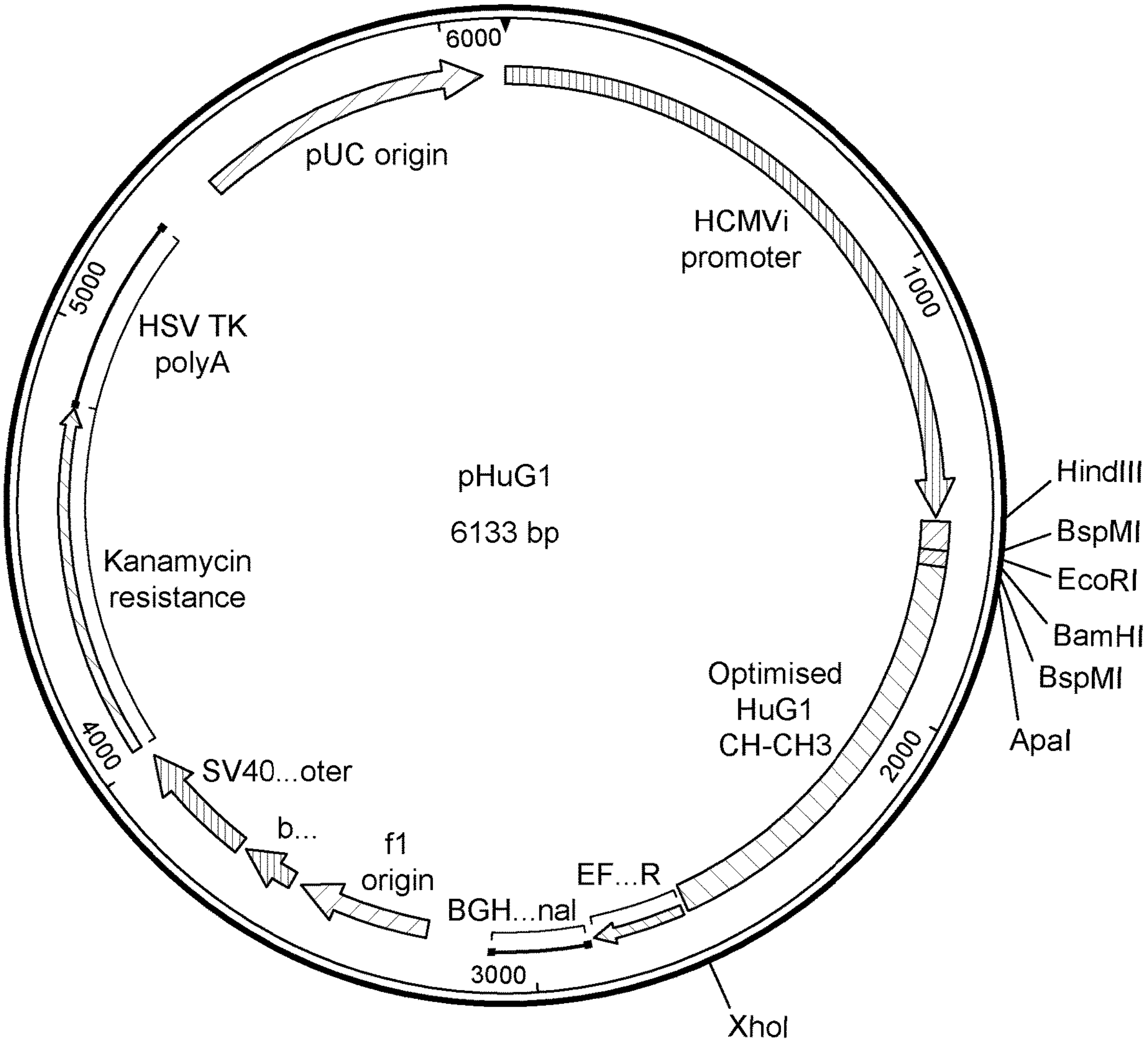

Figure 9: pHuK LIC vector
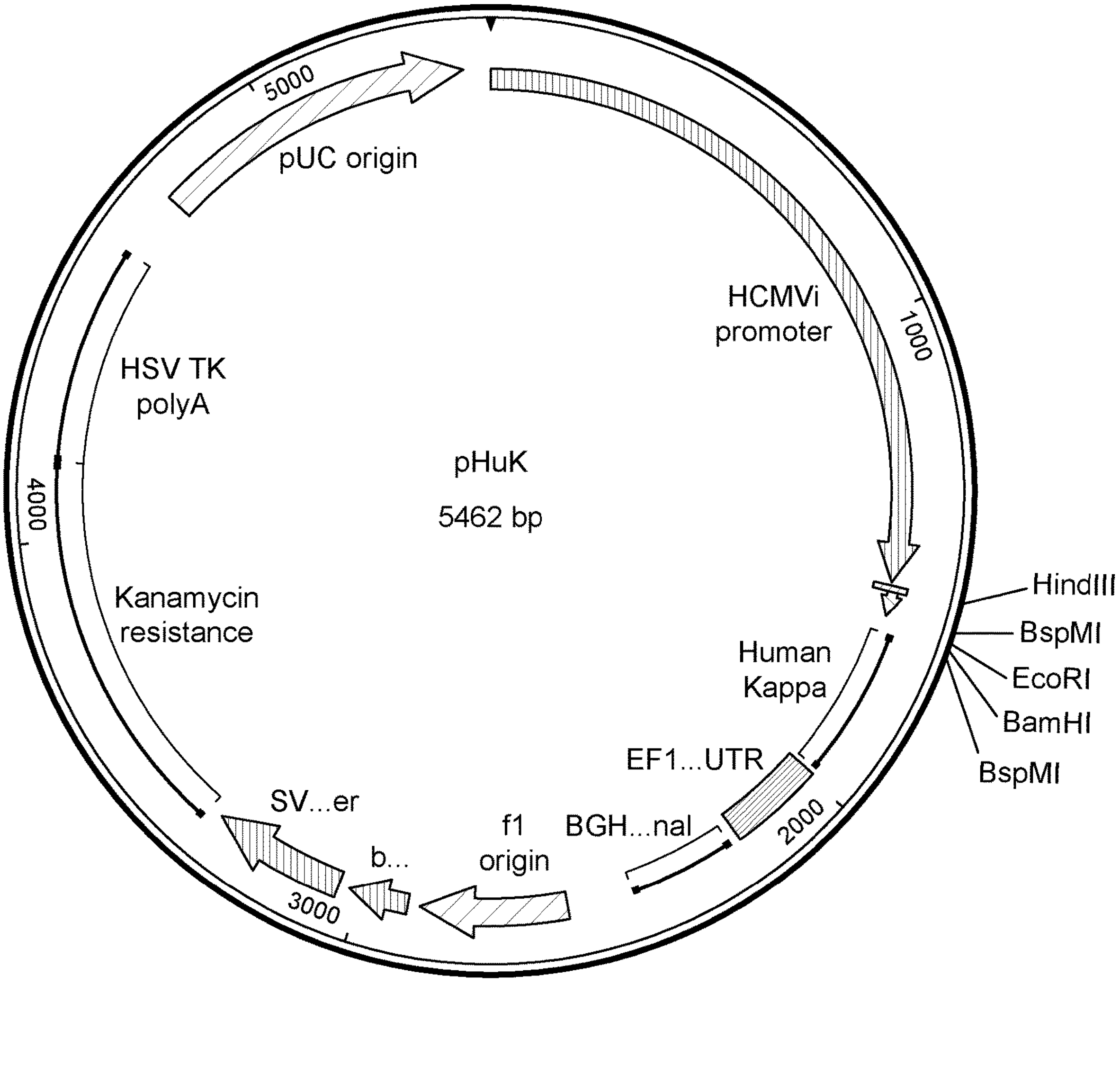

Figure 10: pHuG1_Fab LIC vector
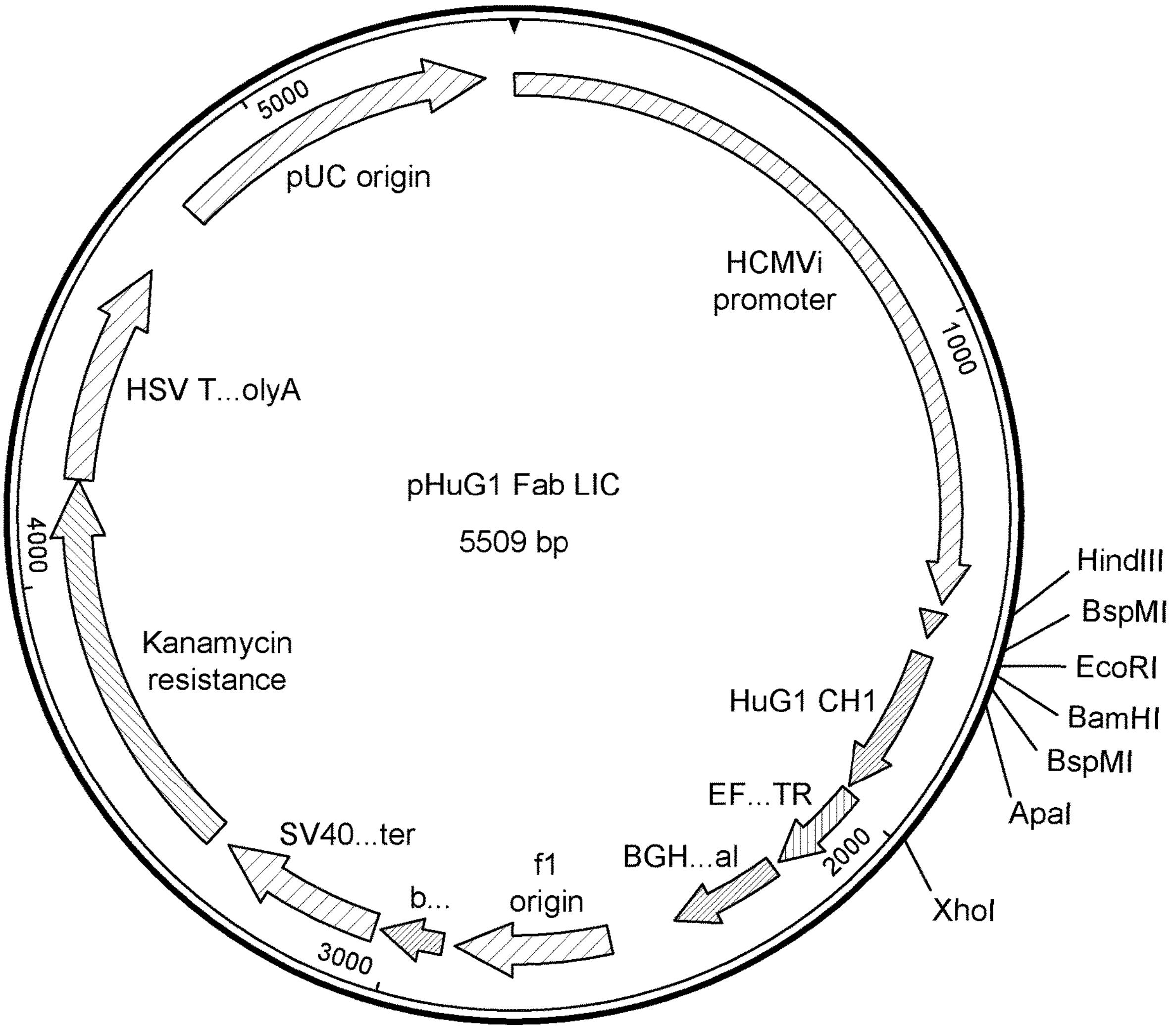

Figure 11: TPAi-1 Kappa Light Chain Variable Region (GenScript Optimised)

CDR_K1

D V L V T Q I P L S L P V S L G D Q A S I S C R S S Q S I V H S N G N T Y L E W Y L Q

CDR_K2

K P G Q S P K L L I Y K V S N R F S G V P D R F S G S G S G T D F T L K I S R V E A E D

SEQ ID NO: 92

SEQ ID NO: 93

CDR_K3

L G V Y Y C F Q G S H V P W T F G G G T K L E I K

SEQ ID NO: 109

Figure 12: TPAi-1 Heavy Chain Variable Region (GenScript Optimised)

CDR_H1

Q V Q L Q Q S G D D L V K P G A S V K L S C K A S G N T S Y W I T W I K Q R P G Q G L

CDR_H2

E W I G R I F P G G G S T Y Y N E I F K G K S I L T V D T S S S T A Y I Q L S S L S S E

SEQ ID NO: 94

SEQ ID NO: 95

CDR_H3

D S A V Y F C A S Y Y Y A M A Y W G Q G T S V T V S S

SEQ ID NO: 110

Figure 13: Binding of chimeric and murine TPAi-1 Antibody to tPA Antigen
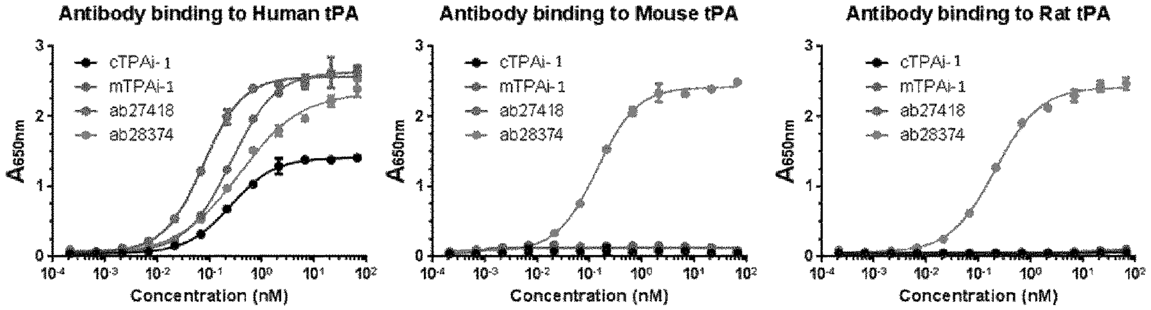
| EC50 values (nM) | Human (rh-tPA)) | Mouse (mr-tPA) | Rat (rr-tPA) |
|---|---|---|---|
| chimeric TPAi- 1 | 0.249 | NB | NB |
| mouse TPAi-1 | 0.249 | NB | NB |
| Anti-TPA tPA antibody ab27418 (abcam) | 0.075 | NB | NB |
| Anti-TPA tPA antibody ab28374 (abcam) | 0.369 | 0.140 | 0.207 |

Figure 14: Cloning and mutagenesis primers

| Name | Sequence (5' → 3') | |
|---|---|---|
| CTD956_RHC | CAC CAG CTA TTG GAT CAC ATG GGT GAG GCA GGC AAC | SEQ ID No 96 |
| CTD956_RHD | GCT ATT GGA TCA ATT GGA TCA GGC AGG CAA CAG GAC | SEQ ID No 97 |
| CTD956_RHE | CCT GGA GTG GAT GGG AAG AAT CGA CCC TGG AGG AGG | SEQ ID No 98 |
| CTD956_RHF | GGA GGA GGC TCC ACC TAC TAT GCA CAG AAG TTC C | SEQ ID No 99 |
| CTD956_RHG | GGC TCC ACC GGA TAT AAC CAG AAG TTC CAG GG | SEQ ID No 100 |
| CTD956_RHH | CCA GGG CCG GGT GAC CCT GAC AAG AAA CAC CTC C | SEQ ID No 100 |
| CTD956_RHI | CCG GGT GAC CAT GAC AGT GAA CAC CTC CAT CTC TAC | SEQ ID No 101 |
| CTD956_RHP | GGT GAC CAT GAC AAG AGA CAC CTC CAT CTC TAC | SEQ ID No 102 |
| CTD956_RHU | GGT GAC CCT GAC AAG AGA CAC CTC CAT CTC TAC | SEQ ID No 103 |
| CTD956_RHV | GGT GAC CAT GAC AGT GGA CAC CTC CAT CTC TAC | SEQ ID No 104 |

Figure 15: Binding of humanised TPAi-1 to human tPA
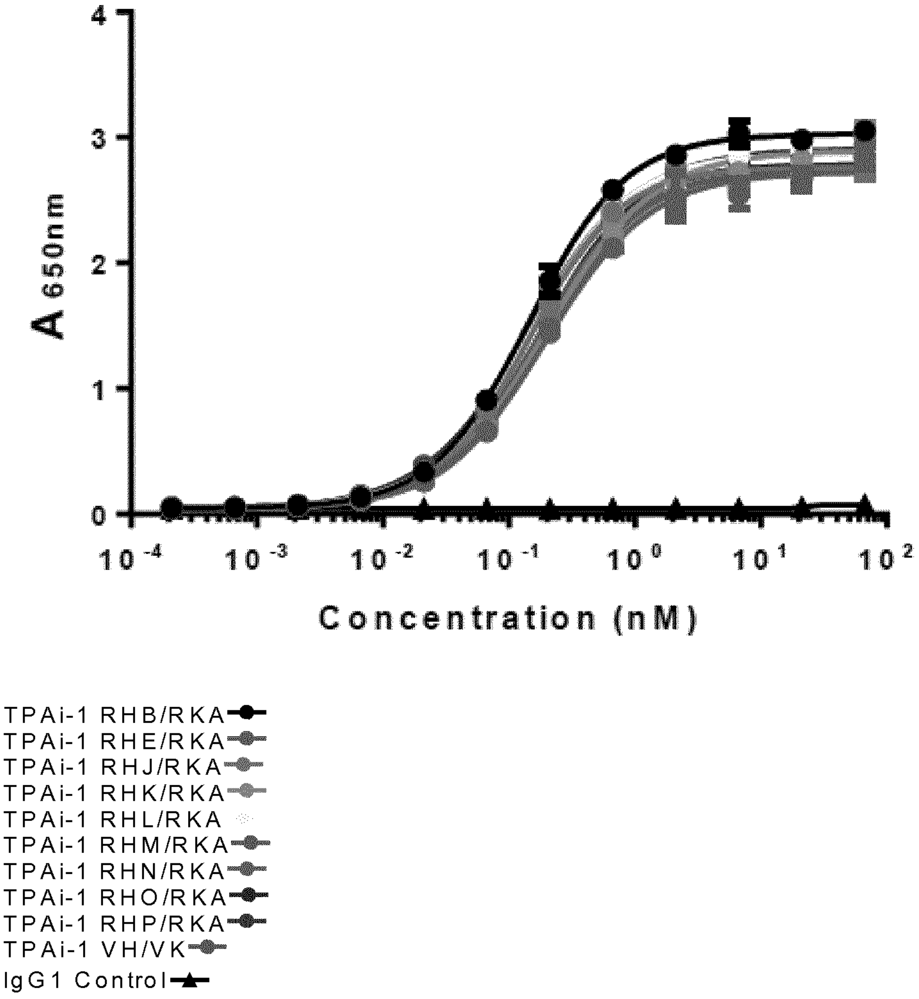
| | $EC_{50}$ (nM) | Expression (µg/ml) |
|---|---|---|
| RHB/RKA | 0.146 | 229.2 |
| RHE/RKA | 0.197 | 189.9 |
| RHJ/RKA | 0.150 | 170.2 |
| RHK/RKA | 0.199 | 202.3 |
| RHL/RKA | 0.151 | 224.5 |
| RHM/RKA | 0.166 | 196.1 |
| RHN/RKA | 0.194 | 160.0 |
| RHO/RKA | 0.177 | 174.8 |
| RHIPRKA | 0.151 | 211.5 |
| Chimeric TPAi-1 | 0.143 | 145.8 |
| IgG1 Control | NR | 402.1 |

Figure 15A: Binding of humanised TPAi-1 to human tPA
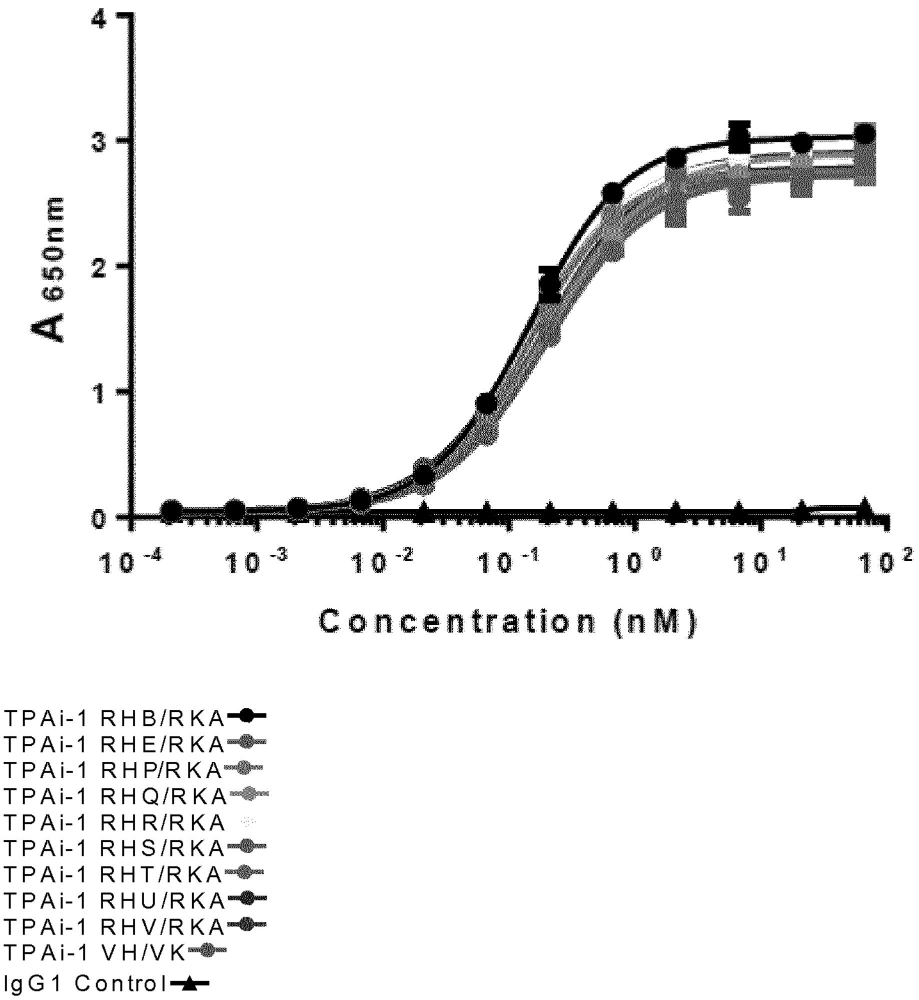
| | IC50 (nM) | Expression (µg/ml) |
|---|---|---|
| RHB/RKA | 0.1572 | 228.0 |
| RHE/RKA | 0.2376 | 160.5 |
| RHP/RKA | 0.2366 | 201.2 |
| RHQ/RKA | 0.2482 | 142.0 |
| RHR/RKA | 0.2151 | 215.6 |
| RHS/RKA | 0.2018 | 208.2 |
| RHT/RKA | 0.2061 | 208.8 |
| RHU/RKA | 0.2132 | 172.2 |
| RHV/RKA | 0.2492 | 144.8 |
| VH/VK | 0.1967 | 99.8 |
| IgG1 Control | NR | 247.5 |

Figure 16: Thermal shift analysis of the purified humanised candidate antibodies
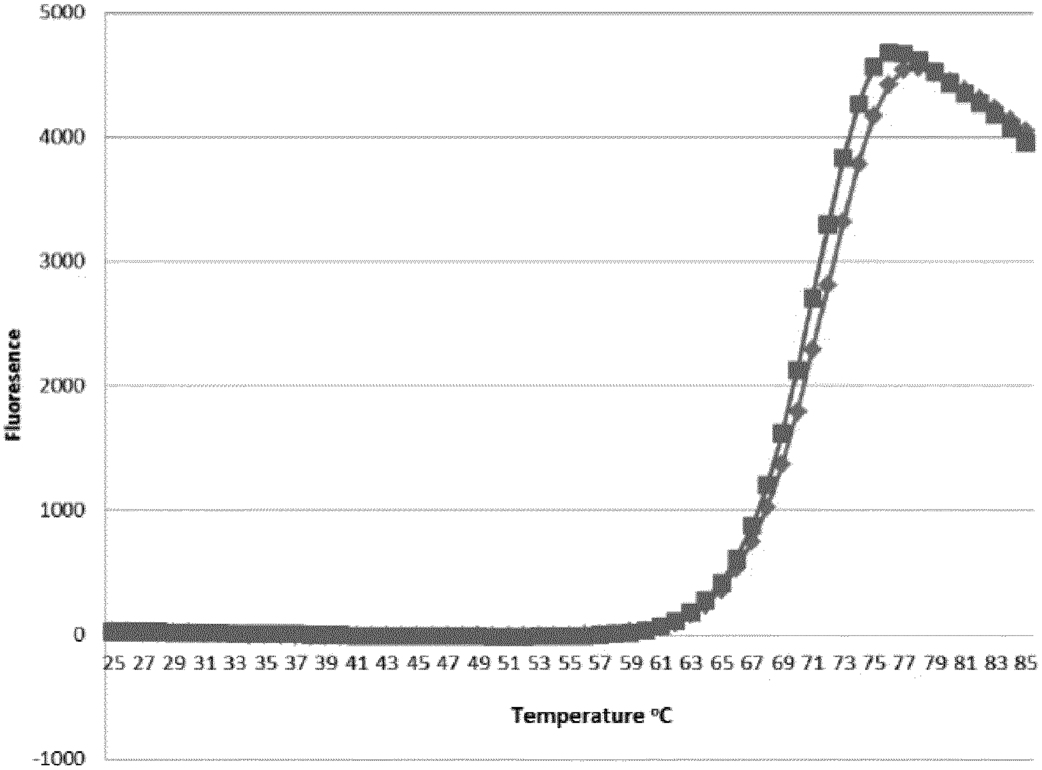
| Antibody | Melting temperature (Tm, °C) |
|---|---|
| RHE/RKA | 71 |
| RHP/RKA | 70 |

Figure 17: Humanised antibody candidates aggregration analysis by DLS

| Sample Name | Z-ave | PdI |
|---|---|---|
| RHE/RKA<br>control IgG | 11.1<br>10.27 | 0.05<br>0.05 |

| Sample Name | Z-ave | PdI |
|---|---|---|
| RHE/RKA<br>control IgG | 10.92<br>10.65 | 0.045<br>0.021 |

For a monomeric antibody, the hydrodynamic diameter of Z-average (Z-ave) is expected around 10.
For a monodisperse sample, the polydisersity index PdI $\leq$ 0.1.

Figure 18: Non-specific protein-protein interactions (Cross-interaction chromatography)

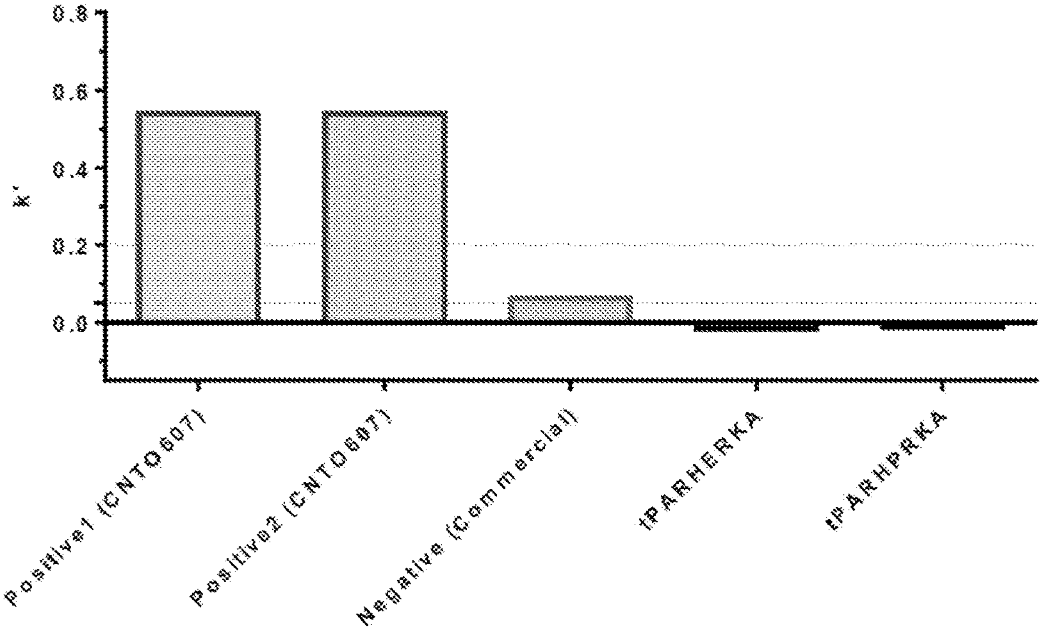

| Antibody | Retention index k' |
|---|---|
| Positive 1 (CNTO607) | 0.55 |
| Positive 2 (CNTO607) | 0.55 |
| Negative (Commercial) | 0.07 |
| RHE/RKA | -0.009 |
| RHP/RKA | -0.004 |

Figure 19: Purified humanised antibody candidates assessed for solubility
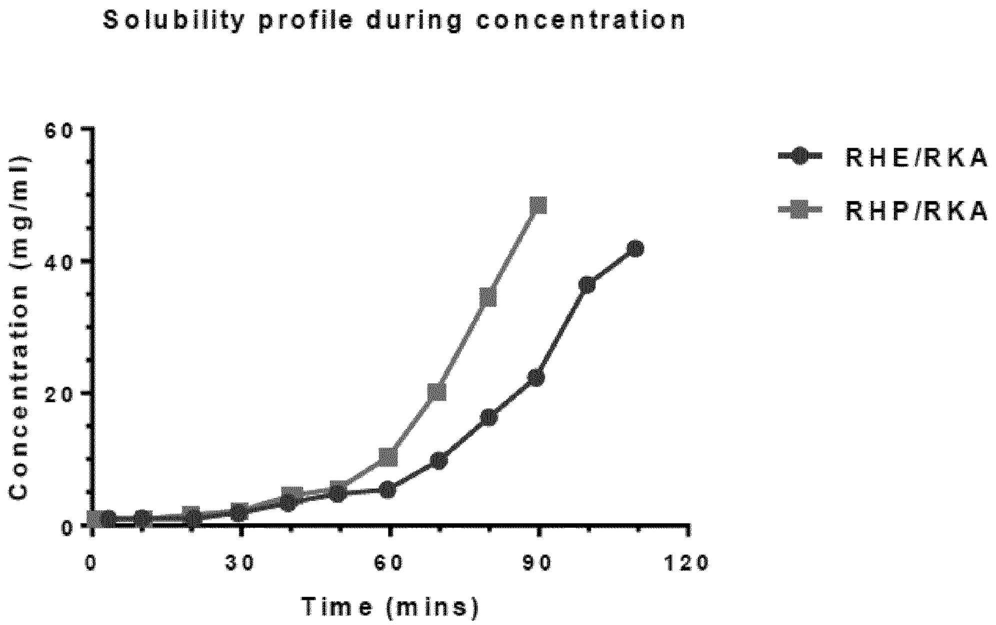
| RHE/RKA | | RHP/RKA | |
|---|---|---|---|
| Time (min) | Concentration(mg/ml) | Time (min) | Concentration(mg/ml) |
| 3.3 | 1.00 | 0.5 | 0.99 |
| 10.0 | 1.04 | 10.5 | 1.01 |
| 20.5 | 1.00 | 19.9 | 1.56 |
| 29.4 | 1.84 | 29.7 | 2.17 |
| 39.4 | 3.35 | 39.7 | 4.36 |
| 49.4 | 4.72 | 40.8 | 4.57 |
| 59.5 | 5.39 | 49.6 | 5.55 |
| 69.8 | 9.76 | 59.6 | 10.33 |
| 79.9 | 16.34 | 69.4 | 20.22 |
| 89.4 | 22.39 | 79.7 | 34.56 |
| 99.7 | 36.44 | 89.8 | 48.36 |
| 109.4 | 41.86 | | |

Freeze/Thaw stress analysis of humanised candidate antibodies

FIG. 20A TPAi-1RHE/RKA

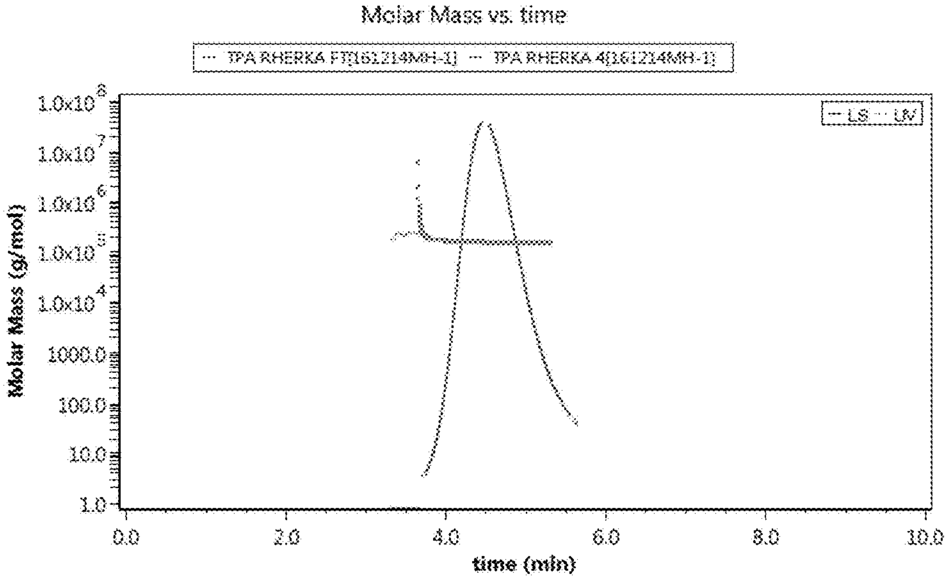

Light scattering data (solid line) and corresponding UV data (dotted line)

| Sample | Mw (kDa) | | Polydispersity (Mw/Mn) | | Monomeric mass fraction (%) |
|---|---|---|---|---|---|
| RHE/RKA Freeze/Thaw Control | 151.75 | ± 0.70 | 1.01 | ± 0.01 | 100.00 |
| RHE/RKA Freeze/Thaw | 151.76 | ± 0.55 | 1.00 | ± 0.00 | 100.00 |

QC criteria: Polydispersity < 1.05; Monomeric mass fraction > 95 % (or < 5 % aggregate).

The monomeric mass fraction is calculated using the light scattering (LS) signal and not the UV signal. It is expressed as a percentage of the total sample (that can be analysed) and corresponds to protein that is not aggregated. Please note, light scattering is intensity weighted and therefore aggregate species (if present) will always 'visually' appear to represent a larger fraction than they actually do.

FIG. 20B TPAi-1 RHP/RKA

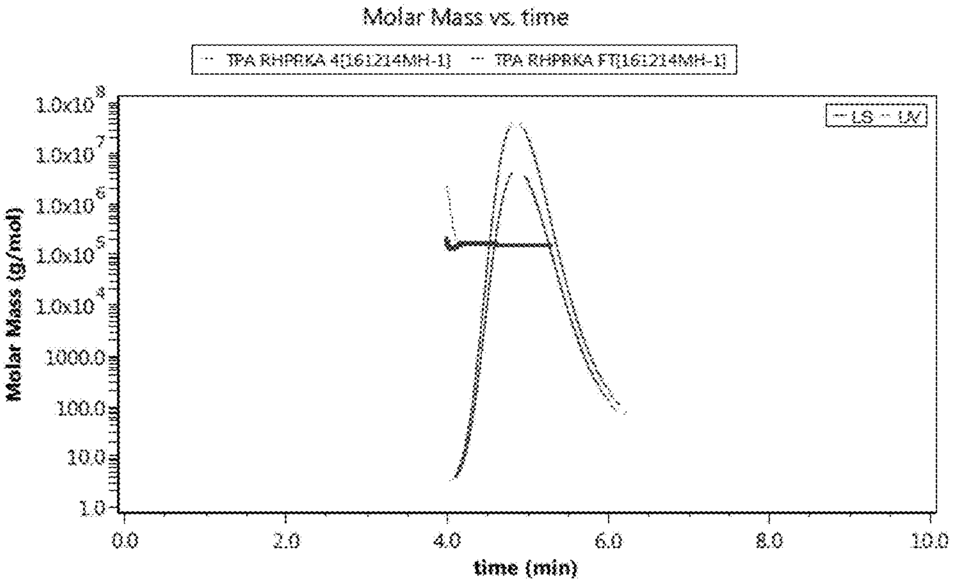

Light scattering data (solid line) and corresponding UV data (dotted line)

| Sample | Mw (kDa) | | Polydispersity (Mw/Mn) | | Monomeric mass fraction (%) |
|---|---|---|---|---|---|
| RHP/RKA Freeze/Thaw Control | 150.47 | ± 1.23 | 1.01 | ± 0.01 | 100 |
| RHP/RKA Freeze/Thaw | 149.00 | ± 0.84 | 1.00 | ± 0.01 | 100 |

QC criteria: Polydispersity < 1.05; Monomeric mass fraction > 95 % (or < 5 % aggregate).

The monomeric mass fraction is calculated using the light scattering (LS) signal and not the UV signal. It is expressed as a percentage of the total sample (that can be analysed) and corresponds to protein that is not aggregated. Please note, light scattering is intensity weighted and therefore aggregate species (if present) will always 'visually' appear to represent a larger fraction than they actually do.

Freeze/Thaw stress analysis of humanised candidate antibodies

FIG. 21A TPAi-1 RHE/RKA

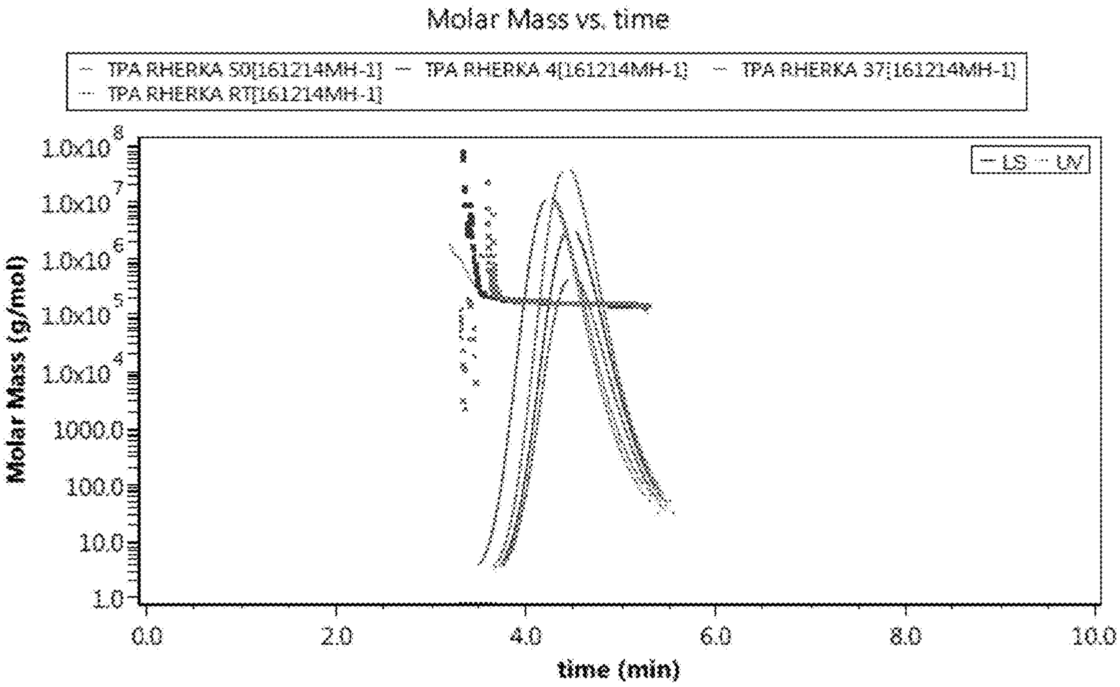

Light scattering data (solid line) and corresponding UV data (dotted line)

| | Mw (kDa) | | Polydispersity (Mw/Mn) | | Monomeric mass fraction (%) |
|---|---|---|---|---|---|
| RHE/RKA 4°C (blue) | 151.75 | ± 0.70 | 1.01 | ± 0.01 | 100 |
| RHE/RKA room temp (green) | 152.43 | ± 0.54 | 1.00 | ± 0.00 | 100 |
| RHE/RKA 37°C (cyan) | 151.01 | ± 0.48 | 1.00 | ± 0.00 | 100 |
| RHE/RKA 50°C (red) | 149.99 | ± 1.16 | 1.01 | ± 0.01 | 100 |

QC criteria: Polydispersity < 1.05; Monomeric mass fraction > 95 % (or < 5 % aggregate).

The monomeric mass fraction is calculated using the light scattering (LS) signal and not the UV signal. It is expressed as a percentage of the total sample (that can be analysed) and corresponds to protein that is not aggregated. Please note, light scattering is intensity weighted and therefore aggregate species (if present) will always 'visually' appear to represent a larger fraction than they actually do.

FIG 21B TPAi-1 RHP/RKA
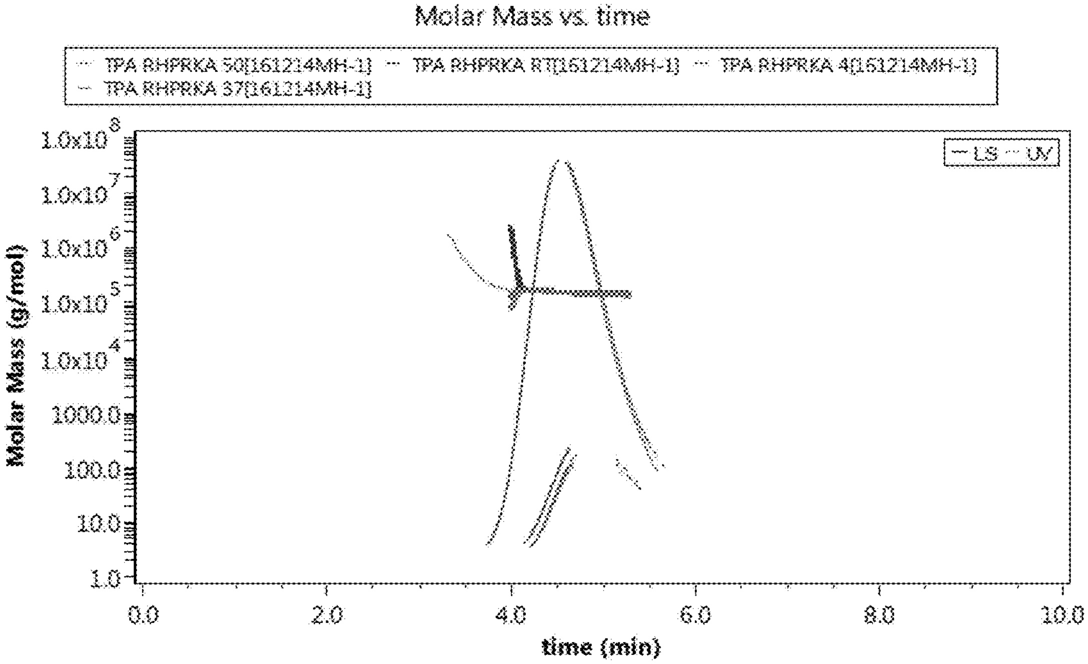
Light scattering data (solid line) and corresponding UV data (dotted line)
| Sample | Mw (kDa) | | Polydispersity (Mw/Mn) | | Monomeric mass fraction (%) |
|---|---|---|---|---|---|
| RHP/RKA 4°C (cyan) | 150.47 | ± 1.23 | 1.01 | ± 0.01 | 100 |
| RHP/RKA room temp (blue) | 149.65 | ± 1.08 | 1.00 | ± 0.01 | 100 |
| RHP/RKA 37°C (green) | 144.81 | ± 0.71 | 1.00 | ± 0.01 | 100 |
| RHP/RKA 50°C (red) | 146.47 | ± 0.48 | 1.01 | ± 0.00 | 100 |

Humanised antibody candidates serum stability assessment
FIG. 22A TPAi-1 RHE/RKA
Plate 1
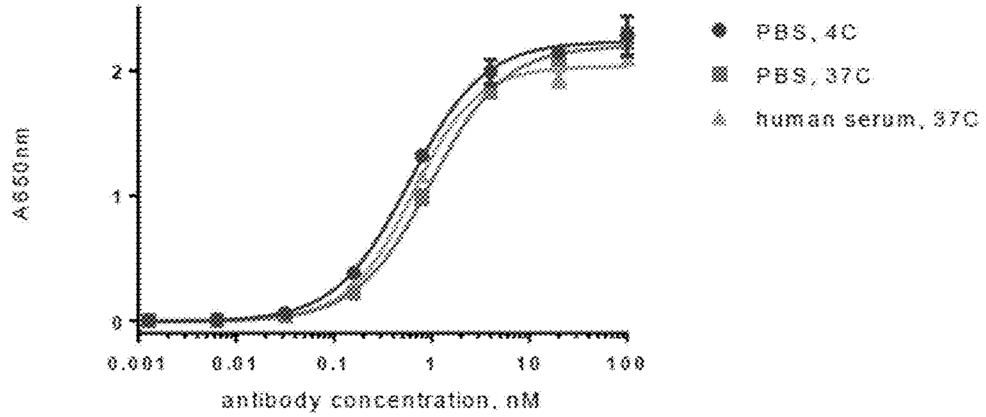
Plate 2
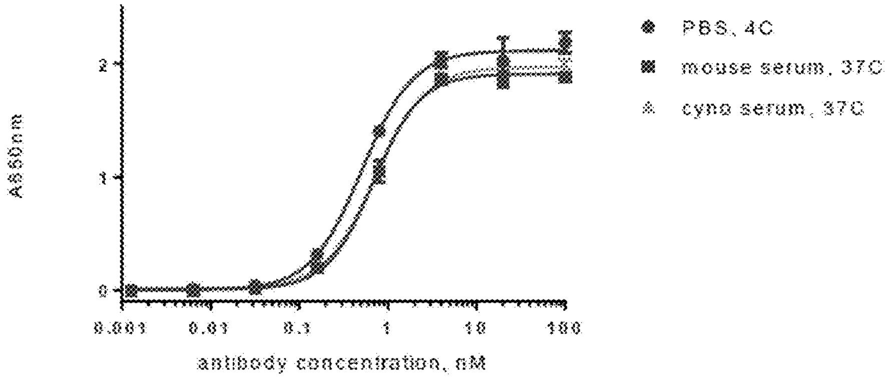
| RHE/RKA sample | | $EC_{50}$ (nM) |
|---|---|---|
| Plate 1 | PBS, 4°C | 0.596 |
| | PBS, 37°C | 0.972 |
| | human serum, 37°C | 0.647 |
| Plate 2 | PBS, 4°C | 0.510 |
| | mouse serum, 37°C | 0.694 |
| | cynomolgus serum,37°C | 0.717 |

FIG. 22B TPAi-1 RHP/RKA
Plate 1
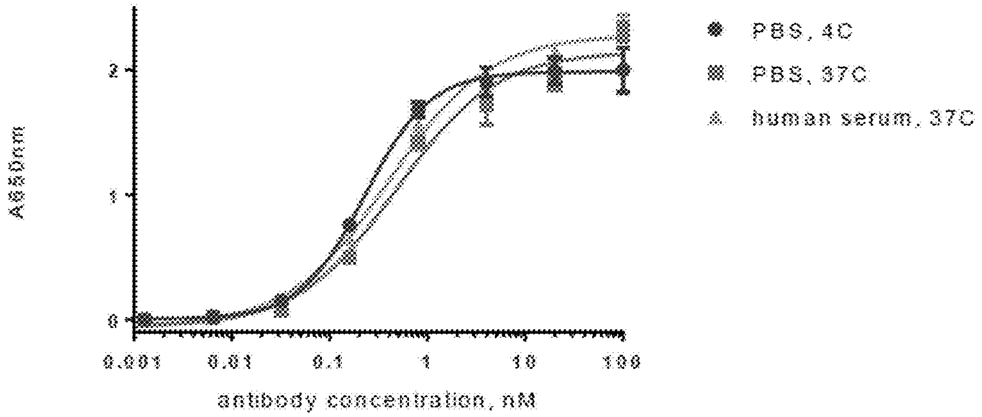
Plate 2
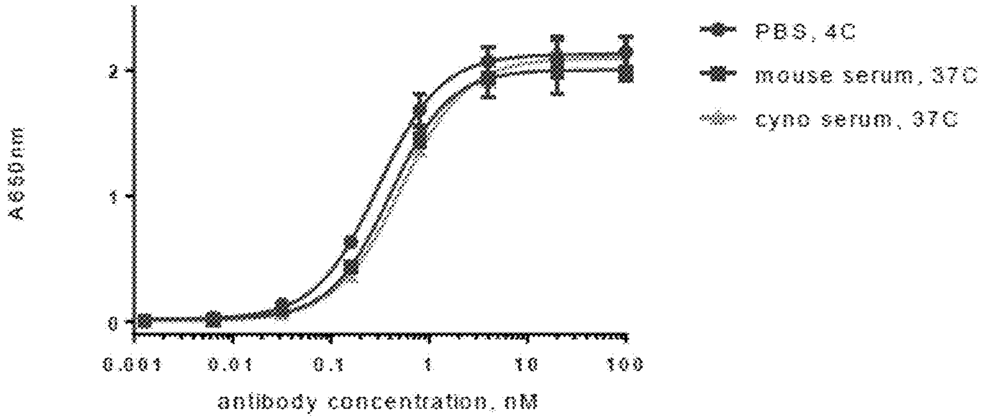
| RHP/RKA sample | | $EC_{50}$ (nM) |
|---|---|---|
| Plate 1 | PBS, 4°C | 0.229 |
| | PBS, 37°C | 0.482 |
| | human serum, 37°C | 0.404 |
| Plate 2 | PBS, 4°C | 0.304 |
| | mouse serum, 37°C | 0.403 |
| | cynomolgus serum,37°C | 0.514 |

Binding of TPAi-1 RHP/RKA Fab to human tPA
FIG. 23A Binding of TPAi-23 RHP/RKA Fab as cell culture
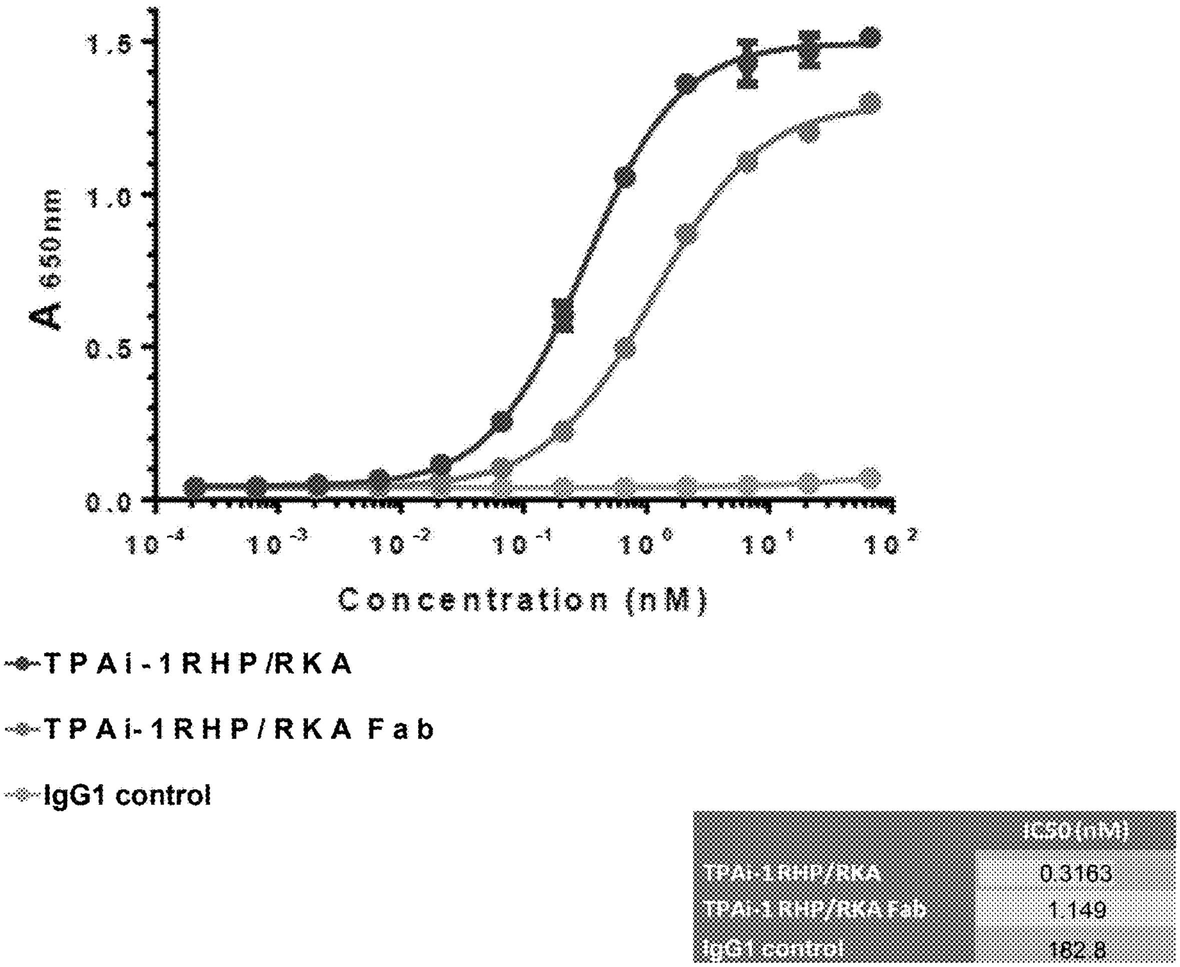
| | IC50 (nM) |
|---|---|
| TPAi-1 RHP/RKA | 0.3163 |
| TPAi-1 RHP/RKA Fab | 1.149 |
| IgG1 control | 182.8 |

FIG. 23B Binding of purified TPAi-1 RHP/RKA
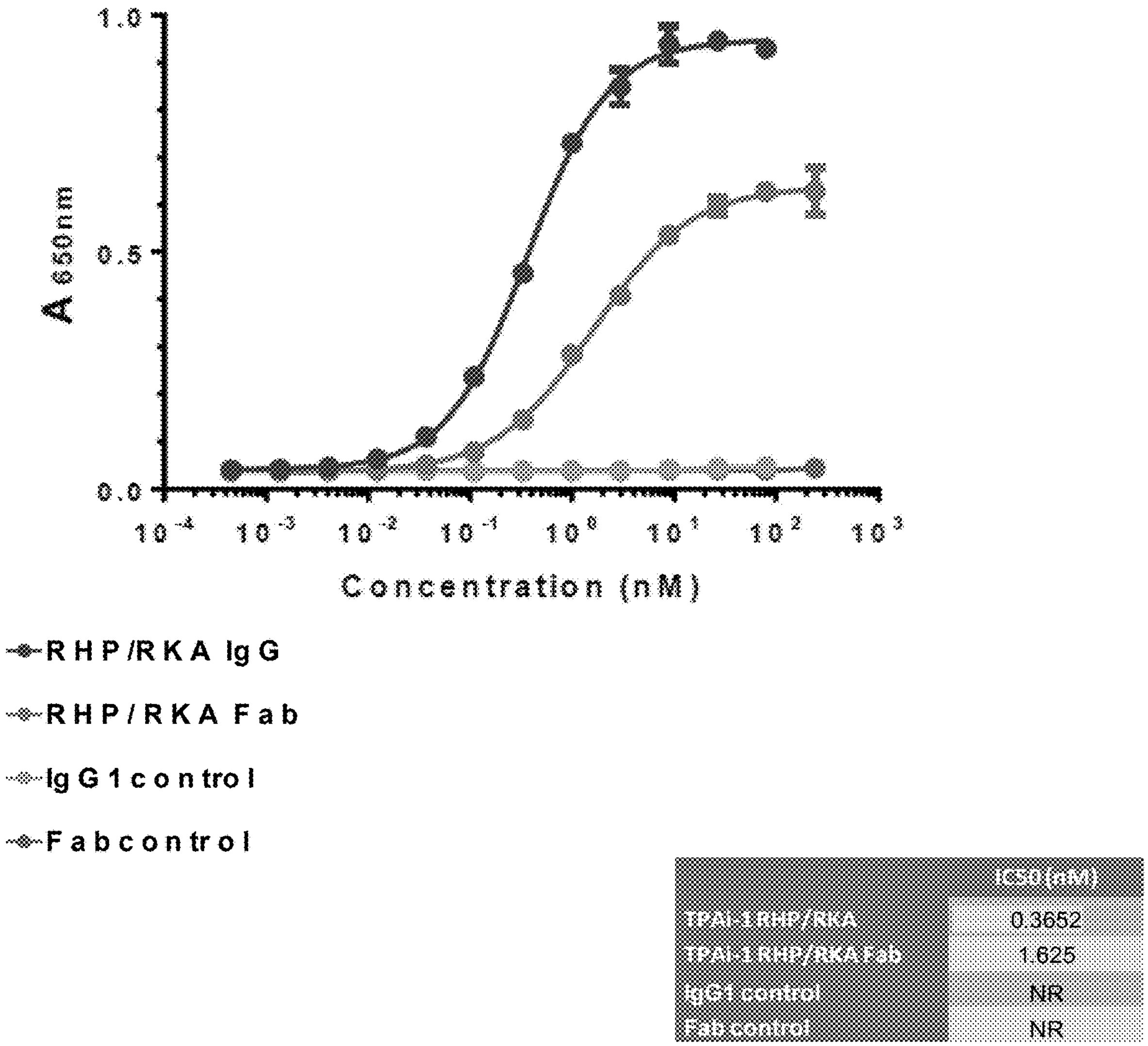
| | IC50 (nM) |
|---|---|
| TPAi-1 RHP/RKA | 0.3652 |
| TPAi-1 RHP/RKA Fab | 1.625 |
| IgG1 control | NR |
| Fab control | NR |

Figure 24: Thermal shift analysis of the purified TPAi-1 RHP/RKA Fab
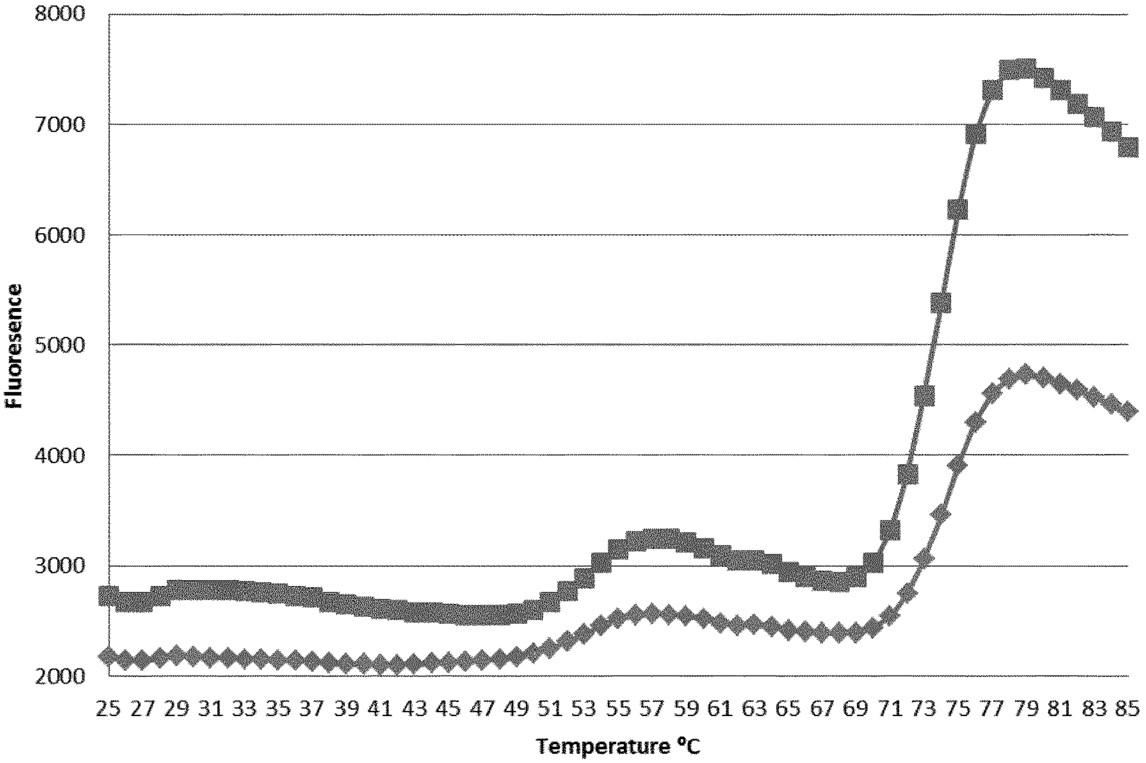
| Sample | Tm (°C) |
|---|---|
| TPAi-1 RHP/RKA Fab, 1 μM (blue) | 74 |
| TPAi-1 RHP/RKA Fab, 2 μM (red) | 74 |

Figure 25: TPAi-1 RHP/RKA Fab aggregation analysis

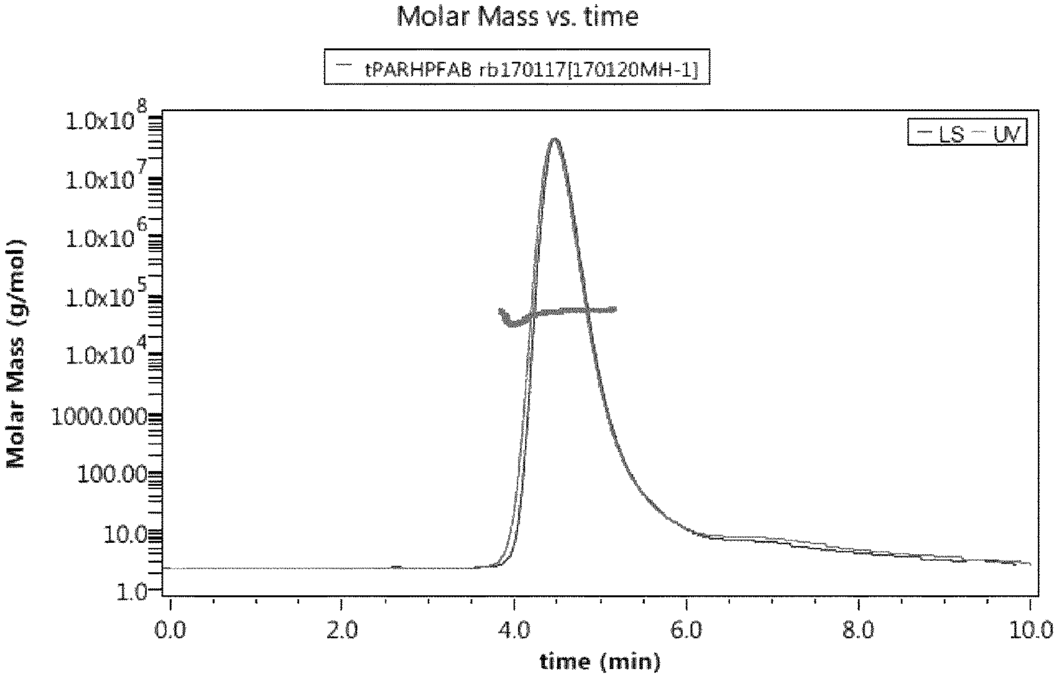

Light scattering data (blue line) and corresponding UV data (red line)

| Sample | Mw (kDa) | | Polydispersity (Mw/Mn) | | Monomeric mass fraction (%) |
|---|---|---|---|---|---|
| TPAi-1 RHP/RKA Fab | 49.5 | ± 0.6 | 1.00 | ± 0.02 | 100 |

QC criteria: Polydispersity < 1.05; Monomeric mass fraction > 95 % (or < 5 % aggregate).

The monomeric mass fraction is calculated using the light scattering (LS) signal and not the UV signal. It is expressed as a percentage of the total sample (that can be analysed) and corresponds to protein that is not aggregated. Please note, light scattering is intensity weighted and therefore aggregate species (if present) will always 'visually' appear to represent a larger fraction than they actually do.

Figure 26: Non-specific protein-protein interactions of TPAi-1 RHP/RKA Fab
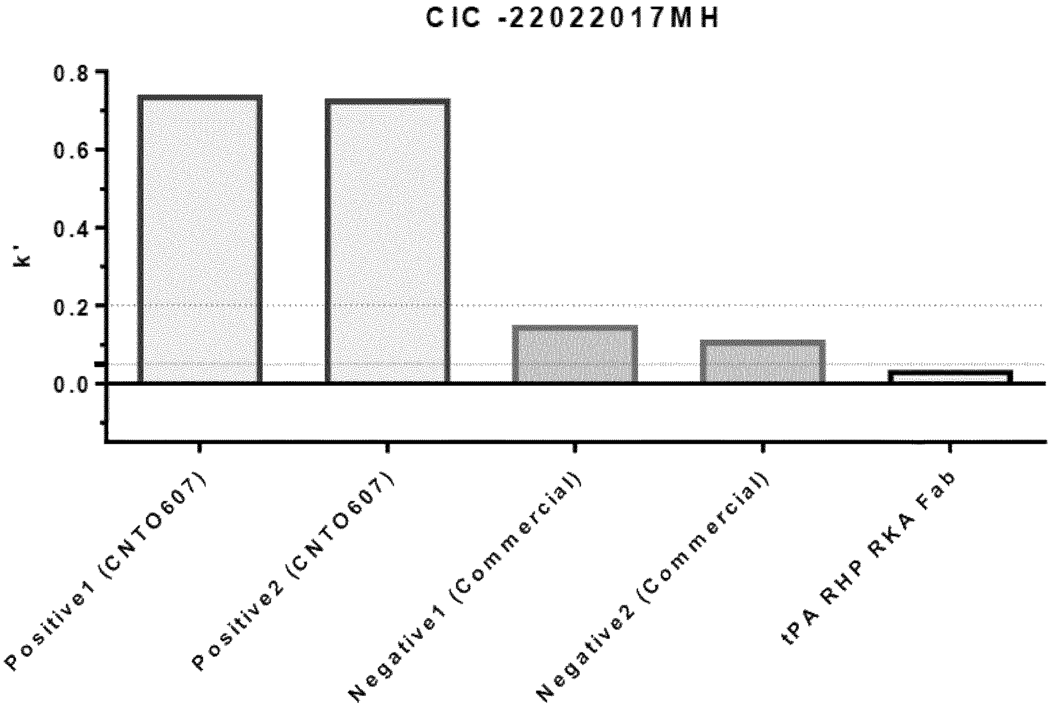
| Antibody | Retention Index k' |
|---|---|
| Positive 1 (CNTO607) | 0.74 |
| Positive 2 (CNTO607) | 0.73 |
| Negative 1 (Commercial) | 0.15 |
| Negative 2 (Commercial) | 0.11 |
| TPAi-1 RHP/RKA Fab | 0.04 |

Figure 27: Purified TPAi-1 RHP/RKA Fab assessed for solubility
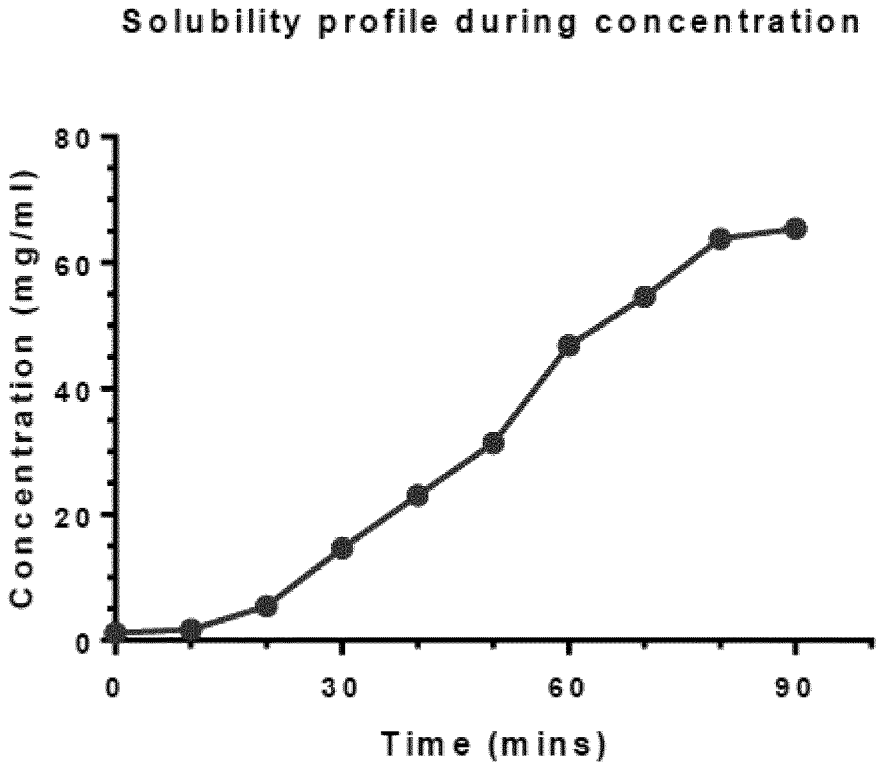
| TPAi-1 RHP/RKA Fab | |
|---|---|
| Time (min) | Concentration(mg/ml) |
| 0 | 1.20 |
| 10 | 1.72 |
| 20 | 5.43 |
| 30 | 14.64 |
| 40 | 23.04 |
| 50 | 31.37 |
| 60 | 46.85 |
| 70 | 54.60 |
| 80 | 63.86 |
| 90 | 65.45 |

Figure 28: Freeze/Thaw stress analysis of TPAi-1 RHP/RKA Fab

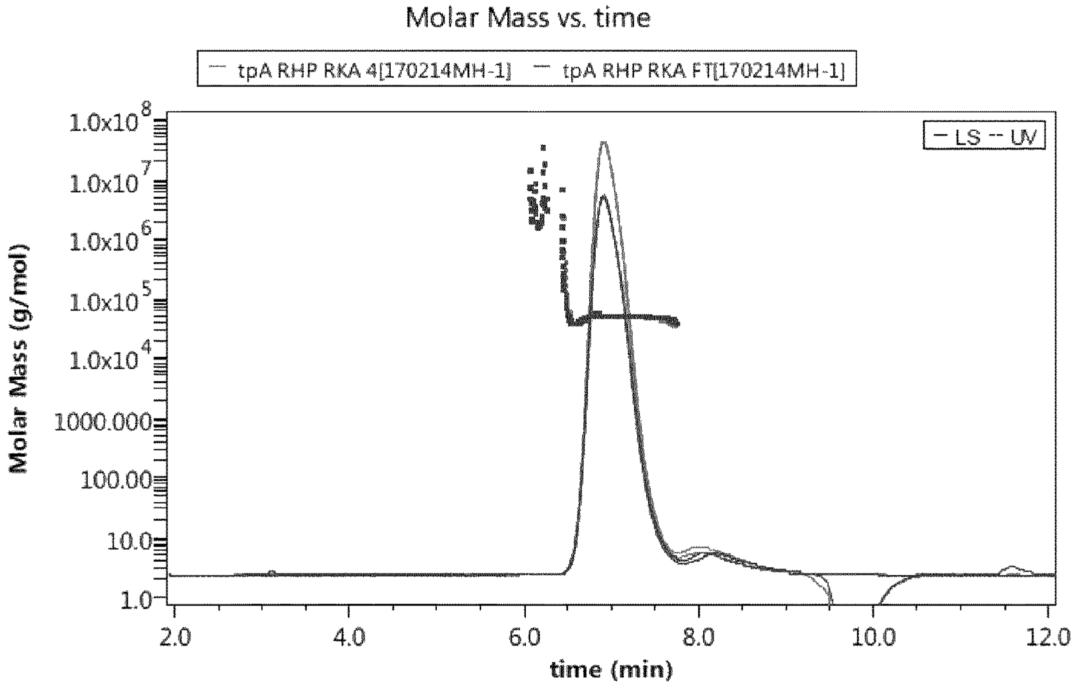

Light scattering data (solid line) and corresponding UV data (dotted line)

| Sample | Mw (kDa) | | Polydispersity (Mw/Mn) | | Monomeric mass fraction (%) |
|---|---|---|---|---|---|
| TPAi-1 RHP/RKA Fab Freeze/Thaw Control (red) | 48.71 | ± 0.36 | 1.01 | ± 0.01 | 100 |
| TPAi-1 RHP/RKA Fab Freeze/Thaw (blue) | 49.00 | ± 0.39 | 1.00 | ± 0.01 | 100 |

QC criteria: Polydispersity < 1.05; Monomeric mass fraction > 95 % (or < 5 % aggregate).

The monomeric mass fraction is calculated using the light scattering (LS) signal and not the UV signal. It is expressed as a percentage of the total sample (that can be analysed) and corresponds to protein that is not aggregated. Please note, light scattering is intensity weighted and therefore aggregate species (if present) will always 'visually' appear to represent a larger fraction than they actually do.

Figure 29: TPAi-1 RHP/RKA Fab heat induced stress analysis

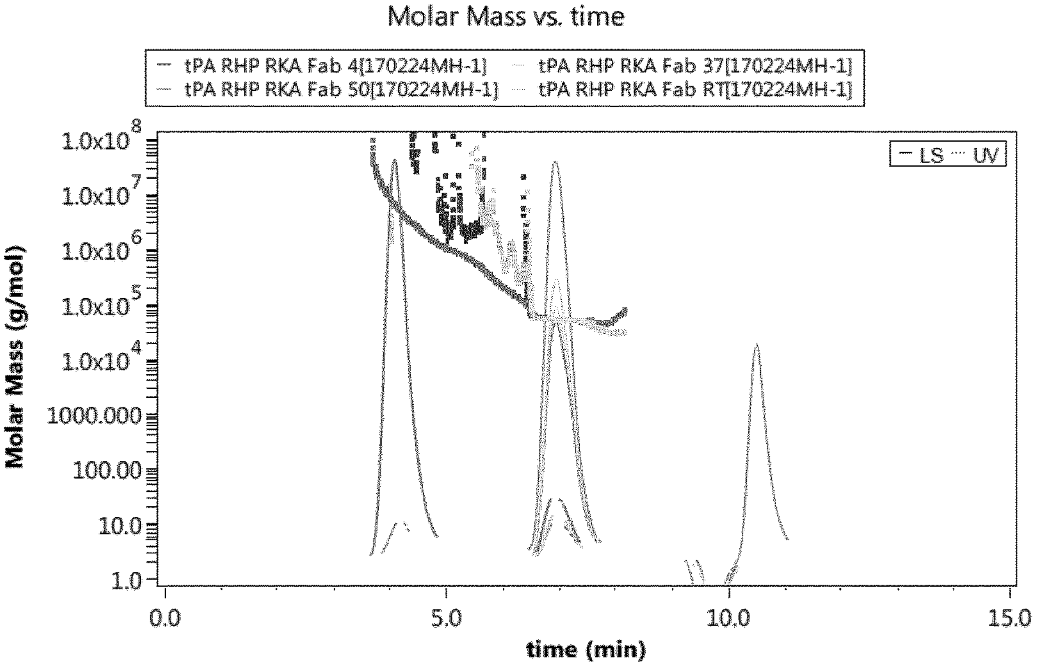

Light scattering data (solid line) and corresponding UV data (dotted line)

| Sample | Mw (kDa) | | Polydispersity (Mw/Mn) | | Monomeric mass fraction (%) |
|---|---|---|---|---|---|
| TPAi-1 RHP/RKA Fab 4°C (blue) | 49.44 | ± 0.68 | 1.00 | ± 0.02 | 99.9 |
| TPAi-1 RHP/RKA Fab room temp (cyan) | 49.82 | ± 0.95 | 1.01 | ± 0.02 | 100 |
| TPAi-1 RHP/RKA Fab 37°C (green) | 49.69 | ± 0.96 | 1.00 | ± 0.03 | 99.9 |
| TPAi-1 RHP/RKA Fab 50°C (red) | 50.61 | ± 0.68 | 1.00 | ± 0.02 | 91.8 |

QC criteria: Polydispersity < 1.05; Monomeric mass fraction > 95 % (or < 5 % aggregate).

The monomeric mass fraction is calculated using the light scattering (LS) signal and not the UV signal. It is expressed as a percentage of the total sample (that can be analysed) and corresponds to protein that is not aggregated. Please note, light scattering is intensity weighted and therefore aggregate species (if present) will always 'visually' appear to represent a larger fraction than they actually do.

Figure 30: TPAi-1 RHP/RKA Fab serum stability assessment
Plate 1
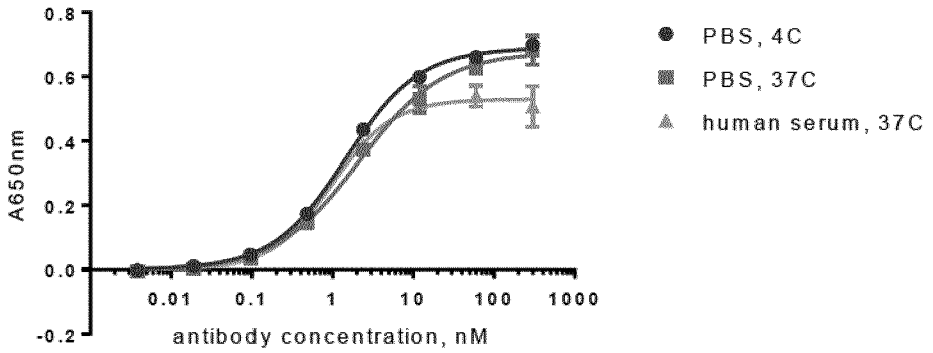
Plate 2
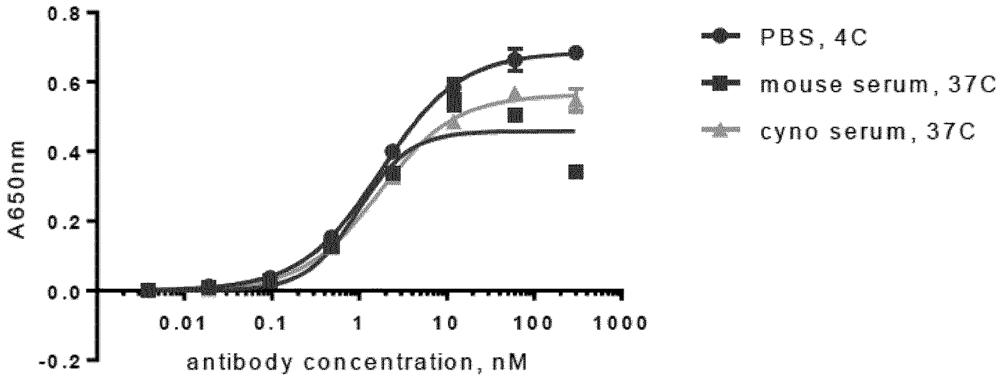
| | RHP/RKA Fab sample | $EC_{50}$ (nM) |
|---|---|---|
| **Plate 1** | PBS, 4°C | 1.452 |
| | PBS, 37°C | 2.157 |
| | human serum, 37°C | 0.978 |
| Plate 2 | PBS, 4°C | 1.751 |
| | mouse serum, 37°C | 0.966 |
| | cynomolgus serum,37°C | 1.685 |

Preparation of TPAi-1 RHP/RKA F(ab')2
FIG. 31A Pepsin digestion of TPAi-1 RHP/RKA analysed by SDS-
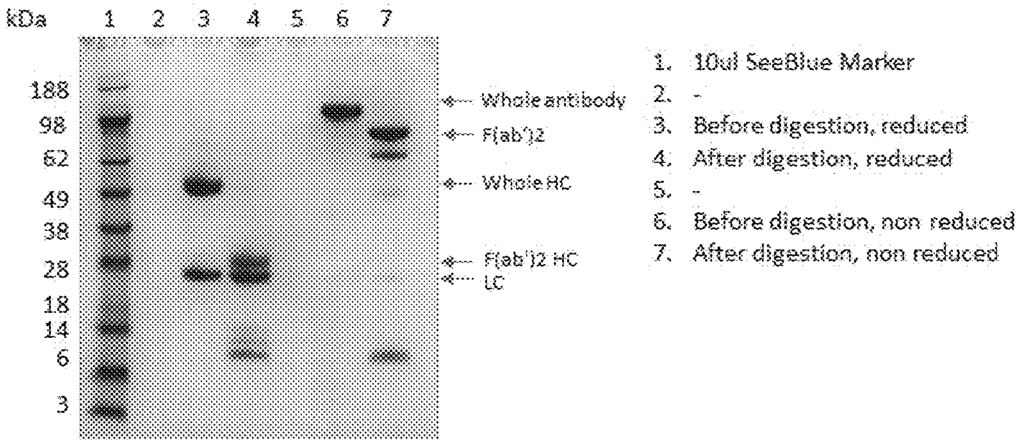
FIG. 31B Gel filtration purification of F(ab')2
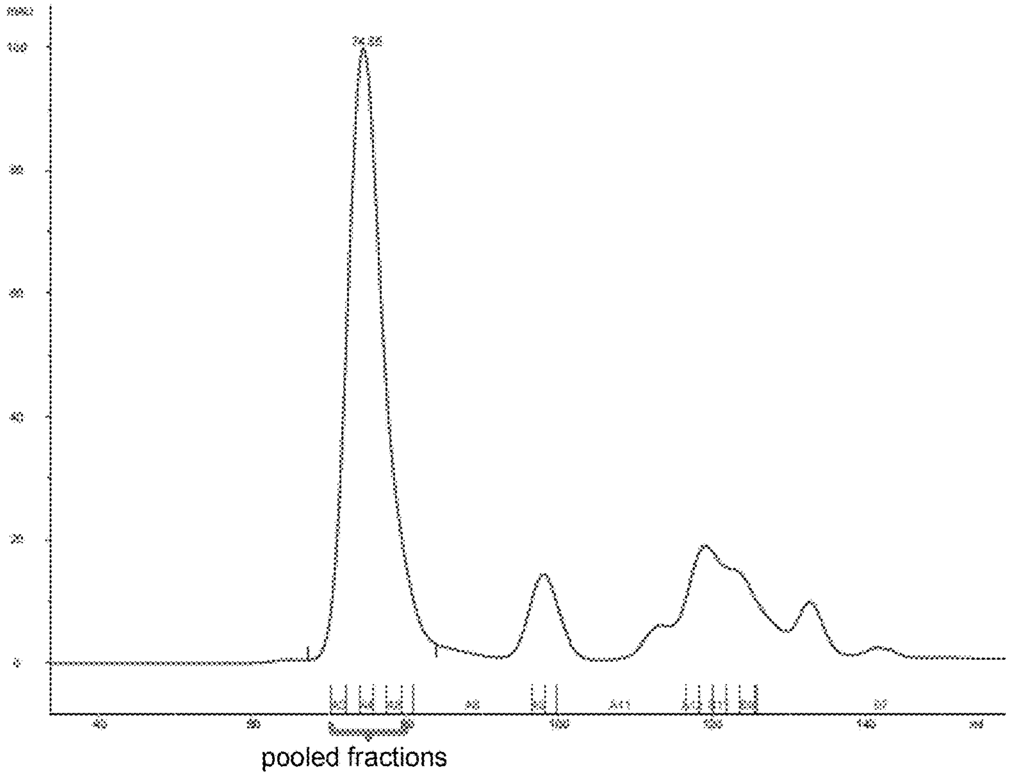

FIG. 31C Purification of TPAi-1 RHP/RKA analysed by SDS-PAGE
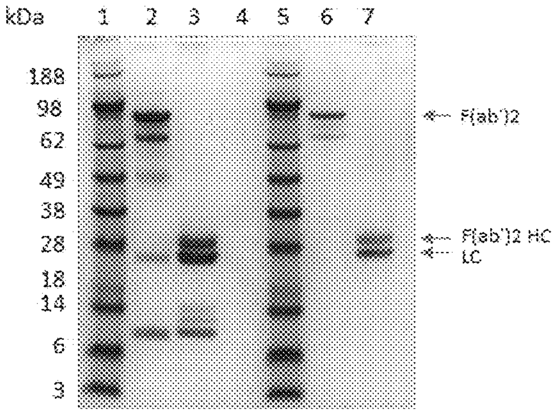
1. 10ul SeeBlue Marker
2. After digestion, non reduced, non purified
3. After digestion, reduced, non purified
4. -
5. 10ul SeeBlue Marker
6. 1µg tPA RHP RKA-Fab2-mh10052017 non reduced
7. 1µg tPA RHP RKA-Fab2-mh10052017 reduced Figure 32: TPAi-1 RHP/RKA F(ab')2 aggregation analysis

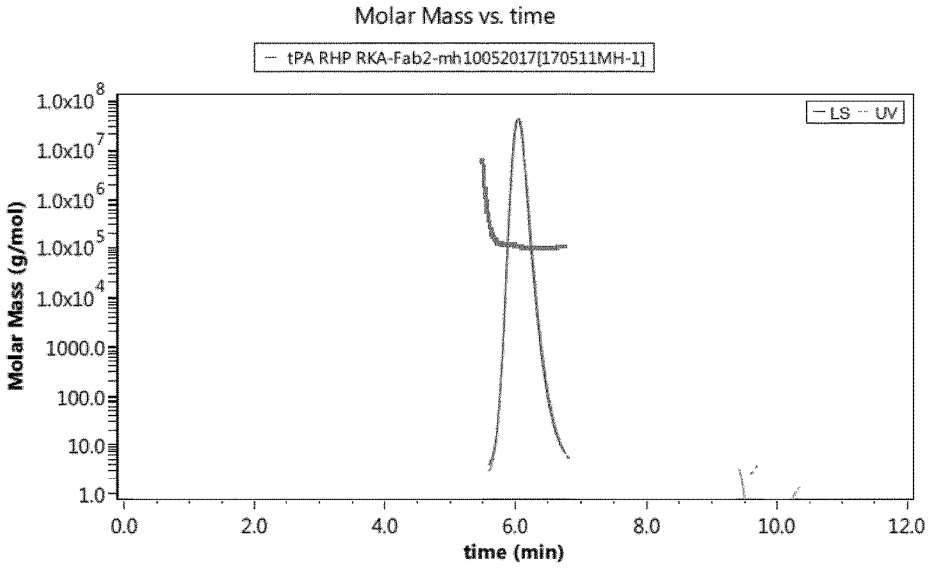

Light scattering data (blue line) and corresponding UV data (red line)

| Sample | Mw (kDa) | | Polydispersity (Mw/Mn) | | Monomeric mass fraction (%) |
|---|---|---|---|---|---|
| TPAi-1 RHP/RKA $(Fab')_2$ | 102.58 | ± 0.95 | 1.01 | ± 0.01 | 100 |

QC criteria: Polydispersity < 1.05; Monomeric mass fraction > 95 % (or < 5 % aggregate).

The monomeric mass fraction is calculated using the light scattering (LS) signal and not the UV signal. It is expressed as a percentage of the total sample (that can be analysed) and corresponds to protein that is not aggregated. Please note, light scattering is intensity weighted and therefore aggregate species (if present) will always 'visually' appear to represent a larger fraction than they actually do.

Figure 33: Binding of TPAi-1 RHP/RKA F(ab')2 to human tPA
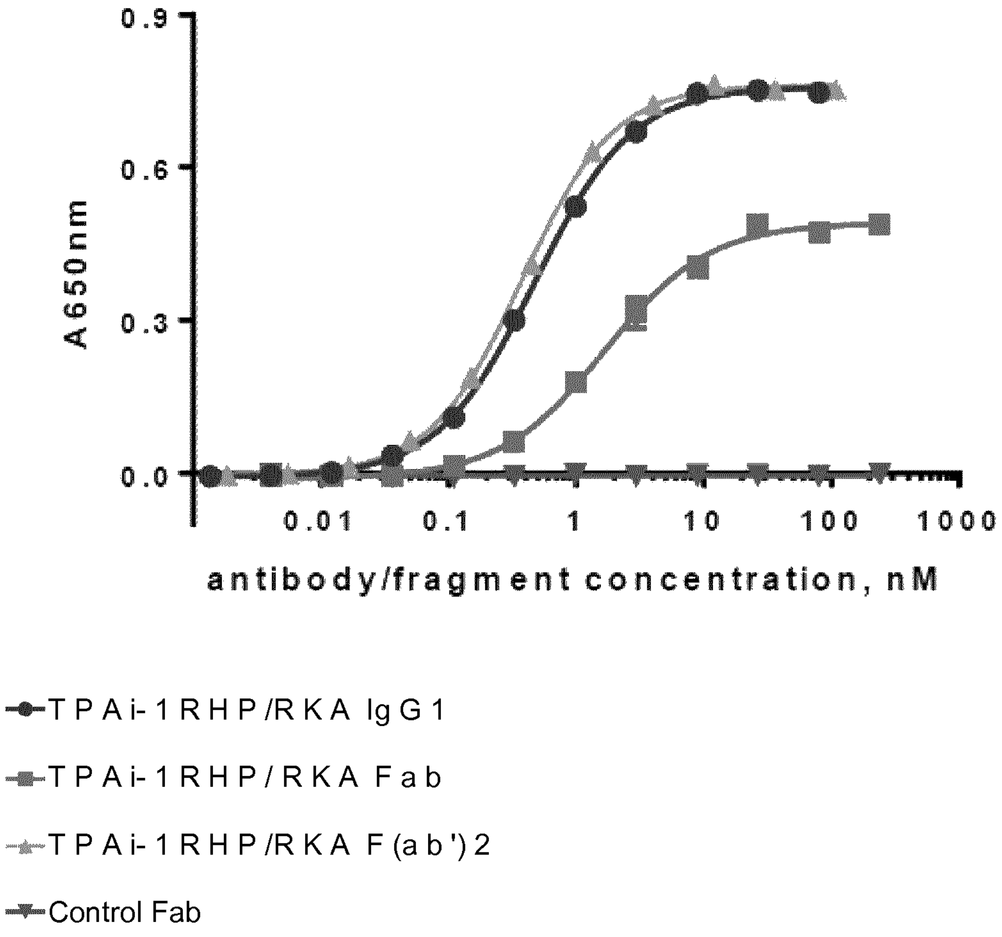
| | IC50 (nM) |
|---|---|
| TPAi-1 RHP/RKA IgG1 | 0.475 |
| TPAi-1 RHP/RKA Fab | 1.675 |
| TPAi-1 RHP/RKA F(ab')$_2$ | 0.379 |
| Fab control | NR |

Figure 34: Binding and Activity of Chimeric TPAi-1 and Humanised TPAi-1 (RHP/RKA) In comparison to the murine TPAi-1
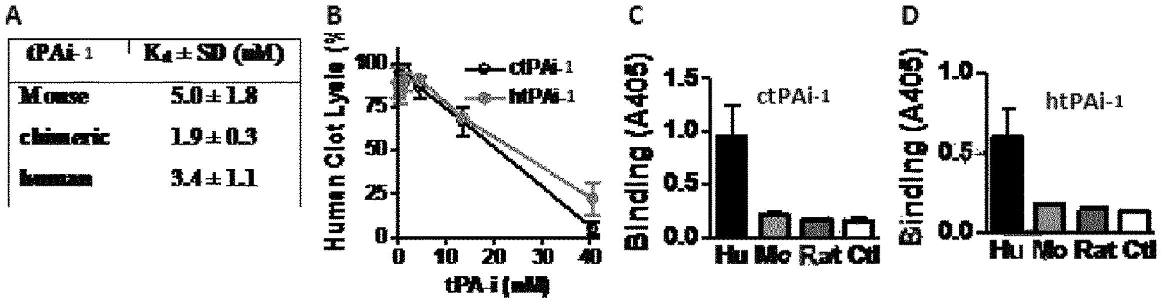
Figure 35: Dose Response Study of the mouse TPAi-1, the humanised TPAi-1 (RHP/RKA) and TPAi-1 (RHP/RKA) Fab in the In Vitro Human Plasma Clot Lysis Inhibition Assay
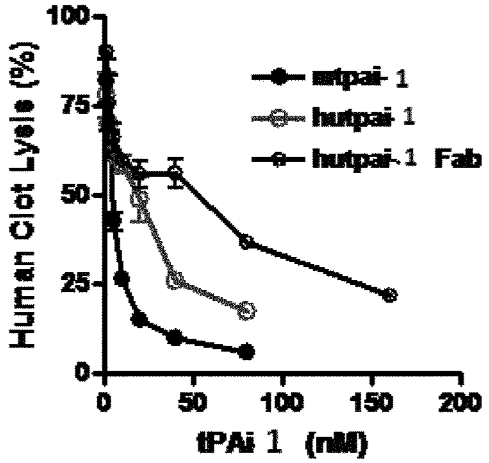
Figure 36: Tail Bleeding (Haemoglobin Loss) as a measure of peripheral or surgical bleeding
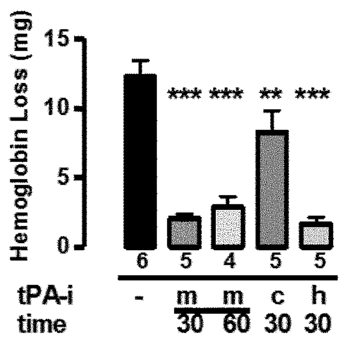

Figure 37: Percentage of Cerebral Hemisphere exhibiting Brain Haemorrhage.
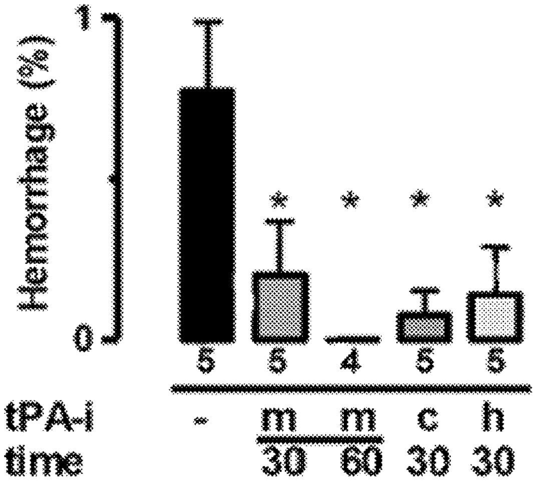
Figure 38: Percentage of the Cerebral Hemisphere exhibiting Infarction
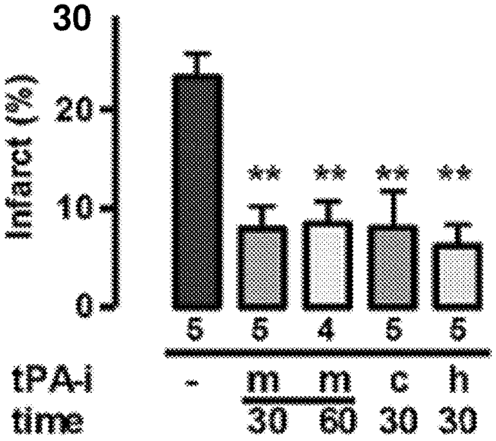

Figure 39: Binding of chimeric TPAi-1, humanised TPAi-1 (RHP/RKA) and TPAi-1 (RHP/RKA) Fab to TPA mutant Tenecteplase
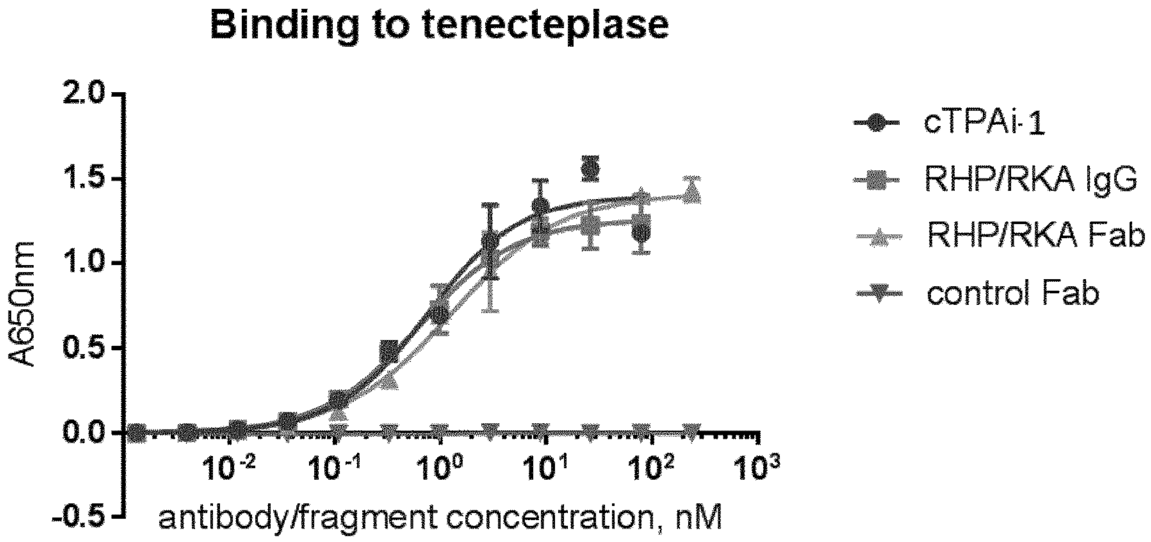

TISSUE PLASMINOGEN ACTIVATOR ANTIBODIES AND METHOD OF USE THEREOF

CROSS-REFERENCE TO RELATED APPLICATIONS

This patent application is the U.S. national stage of International Patent Application No. PCT/EP2019/081225, filed on Nov. 13, 2019, which claims the benefit of Great Britain Patent Application No. 1818477.0, filed Nov. 13, 2018, the disclosures of which are incorporated herein by reference in their entireties for all purposes.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 77,828 byte ASCII (Text) file named "753985_ReplacementSequenceListing.txt", created on Jul. 15, 2025.

BACKGROUND OF THE INVENTION

Field of Invention

The present invention provides tissue plasminogen activator antibody molecules and their uses. More particularly, the presently-disclosed invention provides humanised antibody molecules which specifically bind tissue plasminogen activator (TPA) and their use in treating TPA induced haemorrhage; in particular treating systemic haemorrhage such as brain haemorrhage after treatment of ischemic stroke or myocardial infarction, or systemic bleeding after TPA treatment of pulmonary embolism, ischemic stroke or myocardial infarction, or in patients wherein endogenous TPA is elevated, including, but not limited to, as a result of prolonged coronary artery bypass surgeries, liver transplantation, severe or poly-trauma, heatstroke, or near drowning.

Background Information

Tissue plasminogen activator (TPA or tPA) is the only effective medical treatment for ischemic stroke and it also reduces mortality for patients with acute myocardial infarction. (Donnan G A, Davis S M, Parsons M W, Ma H, Dewey H M, Howells D W. How to make better use of thrombolytic therapy in acute ischemic stroke. *Nat Rev Neural.* 2011; 7:400-409). However, TPA treatment significantly increases the risk of serious or fatal bleeding. Intracranial bleeding after TPA therapy can be devastating and roughly 1% of patients treated with TPA for stroke will experience severely disabling or fatal haemorrhage. (Saver J L. Haemorrhage after thrombolytic therapy for stroke: the clinically relevant number needed to harm. Stroke. 2007; 38:2279-2283.) In a recent study of 511 ischemic stroke patients treated with TPA, up to 20% developed acute deterioration of their mental status necessitating emergent CT scans, revealing a 17% incidence of symptomatic intracranial haemorrhage (sICH), resulting in 87.5% mortality as compared to 22.4% mortality in patients without sICH. (James B, Chang A D, McTaggart R A, et al. Predictors of symptomatic intracranial haemorrhage in patients with an ischaemic stroke with neurological deterioration after intravenous thrombolysis. J Neurol Neurosurg Psychiatry 2018; 89:866-869.) Similar rates of ICH (approximately 6%) are seen with tenecteplase as with Alteplase (Ronning O M, Logallo N, Thommessen B, et al. Tenecteplase versus alteplase between 3 and 4.5 hours in low national institutes of health stroke scale. Stroke 2019; 50(2):498-500), and in a meta-analysis tenecteplase was slightly better in regard to alteplase for the occurrence of any ICH 9.6% versus 11.7% (Xu N, Chen Z, Zhao C, et al. Different doses of tenecteplase vs alteplase in thrombolysis therapy or acute ischemic stroke: evidence from randomized controlled trials. Drug Des Devel Ther 2018; 12:2071-2084). Similarly, 0.9-1.0% of patients given TPA for myocardial infarction develop intracranial haemorrhage and more than 50% of patients die. (Gurwitz J H, Gore J M, Goldberg R J, et al. Risk for intracranial haemorrhage after tissue plasminogen activator treatment for acute myocardial infarction. Participants in the National Registry of Myocardial Infarction 2. *Ann Intern Med.* 1998; 129:597-604.) Although bleeding complications are often seen in older adults, children are also at significant risk of bleeding from TPA. (Gupta A A, Leaker M, Andrew M, et al. Safety and outcomes of thrombolysis with tissue plasminogen activator for treatment of intravascular thrombosis in children. *J Pediatr.* 2001; 139:682-688.) Fear of bleeding complications has diminished the therapeutic administration of TPA to patients who might otherwise benefit. (Saver J L. Hemorrhage after thrombolytic therapy for stroke: the clinically relevant number needed to harm. *Stroke.* 2007; 38:2279-2283.) A recent review of thrombolytic therapy in patients with pulmonary emboli (PE) presented "real world" rates of major bleeding and ICH at >21% and 3.3%, respectively. Further, they concluded that such therapy should only be used in PE patients with unstable cardiovascular status because of these bleeding rates. (Eberle H, Lyn R, Knight T, et al. Clinical update on thrombolytic use in pulmonary embolism: A focus on intermediate-risk patients. Am J Health-Syst Pharm 2018; 75:1275-85). Thus, lack of a specific antidote to TPA or tenecteplase limits access of these agents to the vast majority of PE patients Once TPA-induced haemorrhage occurs there is no specific TPA inhibitor or antidote available to treat the bleeding. In an effort to restore coagulation, patients are frequently given cryoprecipitate, fresh frozen plasma, and platelets without conclusive evidence of efficacy. (Morgenstern L B, Hemphill J C, 3rd, Anderson C, et al. Guidelines for the management of spontaneous intracerebral haemorrhage: a guideline for healthcare professionals from the American Heart Association/American Stroke Association. *Stroke.* 2010 41:2108-2129.) Antifibrinolytic agents such as, tranexamic acid, ε-aminocaproic acid, aprotinin and novel plasmin inhibitors have also been used, but to a limited extent. Unfortunately, these agents not only inhibit the plasminogen (Pg) activation system, but also interfere with other molecular pathways. For example, aprotinin affects plasmin activity as well as the kallikrein system and, has been associated with severe allergies. (Munoz J I, Birkmeyer N J, Birkmeyer J D, O'Connor G T, Dacey L J. Is epsilon-aminocaproic acid as effective as aprotinin in reducing bleeding with cardiac surgery a meta-analysis. *Circulation.* 1999; 99:81-89.)

The mechanisms responsible for TPA bleeding are still relatively poorly understood. By comparison to streptokinase, activation of Pg by TPA is markedly amplified by fibrin and this distinguishing property of TPA was predicted to increase fibrinolysis without increasing bleeding complications. However, excessive plasmin generation by TPA may degrade clotting factors in the circulation that affect coagulation and may enhance bleeding in vivo. TPA is a multi-domain molecule that functions through both catalytic and non-catalytic interactions. There is experimental evidence that non-catalytic actions of TPA (e.g., those not causing plasminogen activation) cause breakdown of the blood brain barrier and are responsible for some of TPA's neurotoxic effects. As such, it is unclear whether TPA-induced brain haemorrhage requires the catalytic activity of TPA. TPA therapy is beneficial in ischemic stroke and myocardial infarction, but in some patients the therapy is complicated by serious or fatal bleeding in the brain and at other sites. Fear of TPA-induced bleeding has limited the therapeutic use of TPA. In humans, TPA-induced haemorrhage and adverse outcomes are more frequent after prolonged ischemia. Similarly, in experimental stroke, after prolonged ischemia, TPA reproducibly causes brain haemorrhage, breakdown of the blood brain barrier and enhanced neuronal cell death.

In non-thrombotic models of stroke there is evidence that TPA may exert toxic effects through mechanisms, such as PDGF-CC cleavage, etc. that do not require plasminogen activation or affect fibrinolytic activity. (Su E J, Fredriksson L, Geyer M, et al. Activation of PDGF-CC by tissue plasminogen activator impairs blood-brain barrier integrity during ischemic stroke. *Nat Med.* 2008; 14:731-737.) Under pathological conditions such as myocardial ischemia and stroke, the fibrinolytic activity of therapeutic TPA is enhanced by increased levels of circulating fibrin fragments (e.g., D-dimer), which may enhance the bleeding process. (Barber M, Langhorne P, Rumley A, Lowe G D, Stott D J. D-dimer predicts early clinical progression in ischemic stroke: confirmation using routine clinical assays. *Stroke.* 2006; 37: 1113-1115.)

It is described in international patent application PCT/US2014/012555, published as WO2014/116706A1, that tissue plasminogen activator activates plasminogen through a fibrin-dependent mechanism that contributes to brain haemorrhage after TPA treatment for ischemic stroke.

SUMMARY OF THE INVENTION

This summary describes several embodiments of the presently-disclosed subject matter, and, in many cases, lists variations and permutations of these embodiments. This summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this summary or not. To avoid excessive repetition, this summary does not list or suggest all possible combinations of such features.

The present invention addresses these and other related needs by providing, inter alia, antibody molecules that are capable of inhibiting TPA-induced fibrinolysis. Tissue plasminogen activator activates plasminogen through a fibrin-dependent mechanism that contributes to systemic haemorrhage, in particular brain haemorrhage, or systemic bleeding after tissue plasminogen activator treatment, more specifically after TPA treatment for ischemic stroke. The antibody molecules of the present invention block this action thereby reducing TPA induced haemorrhage, in particular systemic haemorrhage, more particularly brain haemorrhage, or systemic bleeding after tissue plasminogen activator treatment, more specifically after TPA treatment for ischemic stroke.

The present invention provides an antibody molecule that binds specifically to a human TPA or a TPA mutant. The antibody molecule has sub-nanomolar affinity to inhibit fibrin-dependent plasminogen activation with an IC50<5 nM, and the amino acid sequence of said TPA mutant is at least 65% identical to SEQ ID NO: 1 or SEQ ID NO: 2. The antibody comprises a heavy chain variable domain with a CDR1 selected from the group consisting of SEQ ID NOs: 3 and 4, a CDR2 selected from the group consisting of SEQ ID NO: 5 and 6, and a CDR3 selected from the group consisting of SEQ ID NO: 7 and 8, and a light chain variable domain with a CDR1 selected from the group consisting of SEQ ID NO: 9 and 10, a CDR2 selected from the group consisting of SEQ ID NO: 11 and 12, and a CDR3 of SEQ ID NO: 13.

Typically, the antibody molecule selectively inhibits fibrin-augmented plasminogen activation. Typically, the antibody molecule inhibits degradation of human fibrin clots without affecting TPA amidolytic activity or non-fibrin-dependent activation.

Typically, the antibody molecule is a purified or isolated antibody molecule.

The antibody molecule may be a polyclonal antibody, a monoclonal antibody, a human antibody, a humanized antibody, a chimeric antibody, fragment of an antibody or monoclonal antibody, in particular a Fab, Fab', or F(ab')2 fragment, a single chain antibody, in particular a single chain variable fragment (scFv), a domain antibody, a nanobody, a diabody, or a DARPin.

More specifically, the antibody molecule may be a humanized antibody or a fragment of a humanised antibody, in particular a Fab, Fab', or F(ab')2 fragment, a single chain antibody, in particular a single chain variable fragment (scFv), a Small Modular Immunopharmaceutical (SMIP), a domain antibody, a nanobody, a diabody, or a Designed Ankyrin Repeat Protein (DARPin).

In one aspect, the present invention provides a pharmaceutical composition comprising an antibody molecule of the present invention and a pharmaceutically acceptable carrier.

To be used in therapy, the antibody molecule is included into pharmaceutical compositions appropriate to facilitate administration to animals or humans. Suitable formulations of the antibody molecule may be prepared by mixing the antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed. They include buffer systems such as phosphate, citrate, acetate and other inorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, man nose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. Also organic solvents may be contained in the antibody formulation such as ethanol or isopropanol. The excipients may also have a release-modifying or absorption-modifying function.

In one aspect, the pharmaceutical composition comprises the antibody molecule of the present invention in an aqueous, buffered solution, or a lyophilisate made from such a solution.

A suitable mode of application is parenteral, by infusion or injection (intravenous, intramuscular, subcutaneous, intraperitoneal, intradermal), but other modes of application such as by inhalation, transdermal, intranasal, buccal, oral, may also be applicable.

In a further aspect, the present invention provides an antibody molecule of the present invention for use as a medicament.

In a further aspect, the present invention provides an antibody molecule of the invention for use in the treatment or prevention of TPA induced haemorrhage.

In one embodiment, the present invention provides an antibody molecule of the invention for use in the treatment or prevention of systemic haemorrhage, in particular brain haemorrhage or systemic bleeding after tissue plasminogen activator treatment, more specifically after TPA treatment for ischemic stroke.

In a further aspect, the present invention provides a method of treatment or prevention of TPA induced haemorrhage, comprising administering an effective amount of an antibody molecule of the invention to a subject in need thereof.

In one embodiment, the present invention provides a method of treatment or prevention of systemic haemorrhage, in particular brain haemorrhage or systemic bleeding after tissue plasminogen activator treatment, more specifically after TPA treatment for ischemic stroke, comprising administering an effective amount of an antibody molecule of the invention to a subject in need thereof.

In a further aspect, the present invention provides a kit comprising an antibody molecule of the present invention, or a pharmaceutical composition thereof.

In one aspect, the present invention provides a method of manufacturing an antibody molecule of the present invention, comprising:

(a) providing a host cell comprising one or more nucleic acids encoding said antibody molecule in functional association with an expression control sequence,
(b) cultivating said host cell, and
(c) recovering the antibody molecule from the cell culture.

In a further aspect, the present invention provides a method for identifying molecules that can inhibit TPA-induced fibrinolysis of human clots. The method includes the steps of: providing an antibody molecule of the present invention that specifically binds to TPA and inhibits TPA-induced fibrinolysis of human clots, affixing the antibody molecule to a surface, providing TPA and introducing an agent to the TPA that blocks the non-specific binding regions of TPA, introducing a candidate molecule to the TPA, introducing the TPA to the antibody molecule, determining if the candidate molecule has bound to the epitope of the TPA where the antibody molecule had bound to the TPA, and identifying any candidate molecule binding to the epitope as a molecule that can inhibit TPA-induced fibrinolysis of human clots.

Advantages of the presently-disclosed subject matter will become evident to those of ordinary skill in the art after a study of the description, Figures, and non-limiting Examples in this document.

BRIEF DESCRIPTION OF THE DRAWINGS

FIG. 1: PCR primers for amplifying mouse VK

FIG. 2: PCR primers for amplifying mouse VH

FIG. 3: General PCR and Sequencing primers

FIG. 4: Protein and DNA sequence of TPAi-1 Kappa Light Chain Variable Region FIG. 5: Protein and DNA sequence of TPAi-1 Heavy Chain Variable Region FIG. 6: TPAi-1 Kappa Light Chain Germ Line Analysis FIG. 7: TPAi-1 Heavy Chain Germ Line Analysis FIG. 8: pHuG1 LIC vector FIG. 9: pHuK LIC vector FIG. 10: pHuG1_Fab LIC vector FIG. 11: TPAi-1 Kappa Light Chain Variable Region (GenScript Optimised)

FIG. 12: TPAi-1 Heavy Chain Variable Region (GenScript Optimised)

FIG. 13: Binding of chimeric and murine TPAi-1 Antibody to tPA Antigen

FIG. 14: Cloning and mutagenesis primers

FIG. 15: Binding of humanised TPAi-1 to human tPA

FIG. 15A: Binding of humanised TPAi-1 to human tPA

FIG. 16: Thermal shift analysis of the purified humanised candidate antibodies FIG. 17: Humanised antibody candidates aggregation analysis by DLS FIG. 18: Non-specific protein-protein interactions (Cross-interaction chromatography)

FIG. 19: Purified humanised antibody candidates assessed for solubility

FIG. 20: Freeze/Thaw stress analysis of humanised candidate antibodies

FIG. 21: Freeze/Thaw stress analysis of humanised candidate antibodies

FIG. 22: Humanised antibody candidates serum stability assessment

FIG. 23: Binding of TPAi-1 RHP/RKA Fab to human tPA

FIG. 24: Thermal shift analysis of the purified TPAi-23 RHP/RKA Fab

FIG. 25: TPAi-1 RHP/RKA Fab aggregation analysis

FIG. 26: Non-specific protein-protein interactions of TPAi-1 RHP/RKA Fab

FIG. 27: Purified TPAi-1 RHP/RKA Fab assessed for solubility

FIG. 28: Freeze/Thaw stress analysis of TPAi-1 RHP/RKA Fab

FIG. 29: TPAi-1 RHP/RKA Fab heat induced stress analysis

FIG. 30: TPAi-1 RHP/RKA Fab serum stability assessment

FIG. 31: Preparation of TPAi-1 RHP/RKA F(ab')2

FIG. 32: TPAi-1 RHP/RKA F(ab')2 aggregation analysis

FIG. 33: Binding of TPAi-1 RHP/RKA F(ab')2 to human tPA

FIG. 34: Binding and Activity of Chimeric TPAi-1 and Humanised TPAi-1 (RHP/RKA) In comparison to the murine TPAi-1.

FIG. 35: Dose Response Study of the mouse TPAi-1, the humanised TPAi-1 (RHP/RKA) and TPAi-1 (RHP/RKA) Fab in the In Vitro Human Plasma Clot Lysis Inhibition Assay FIG. 36: Tail Bleeding (Haemoglobin Loss) as a measure of peripheral or surgical bleeding FIG. 37: Percentage of Cerebral Hemisphere exhibiting Brain Haemorrhage FIG. 38: Percentage of the Cerebral Hemisphere exhibiting Infarction FIG. 39: Binding of chimeric TPAi-1, humanised TPAi-1 (RHP/RKA) and TPAi-1 (RHP/RKA) Fab to TPA mutant Tenecteplase

DETAILED DESCRIPTION OF THE INVENTION

Some of the polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein.

The present invention provides an antibody molecule that binds specifically to a human TPA or a TPA mutant to inhibit degradation of human fibrin clots, wherein the antibody has sub-nanomolar affinity to inhibit fibrin-dependent plasminogen activation with an IC50<5 nM, and wherein the amino acid sequence of said TPA mutant has at least 65% identity to SEQ ID NO: 1 or SEQ ID NO: 2; wherein the antibody comprises a heavy chain variable domain with a CDR1 selected from the group consisting of SEQ ID NOs: 3 and 4, a CDR2 selected from the group consisting of SEQ ID NO: 5 and 6, and a CDR3 selected from the group consisting of SEQ ID NO: 7 and 8, and a light chain variable domain with a CDR1 selected from the group consisting of SEQ ID NO: 9 and 10, a CDR2 selected from the group consisting of SEQ ID NO: 11 and 12, and a CDR3 of SEQ ID NO: 13.

This invention relates to the provision and use of antibody molecules as specific inhibitors of fibrin-dependent Pg activation in TPA-induced haemorrhage, in particular systemic haemorrhage such as brain haemorrhage, systemic bleeding after tissue plasminogen activator treatment. More specifically, certain antibody molecules function as inhibitors and act synergistically to reduce plasminogen activation and fibrinolysis with greater potency than plasminogen activator inhibitor-I (PAI-I). In a model of thromboembolic stroke, these inhibitors significantly reduced brain haemorrhage and surgical bleeding after TPA administration.

The present invention provides an antibody molecule that binds specifically to a human TPA or a TPA mutant to inhibit degradation of human fibrin clots, wherein the antibody has sub-nanomolar affinity to inhibit fibrin-dependent plasminogen activation with an IC50<5 nM, and wherein the amino acid sequence of said TPA mutant has at least 65% identity to SEQ ID NO: 1 or SEQ ID NO: 2. In some embodiments, the antibody molecule does not affect TPA amidolytic activity or non-fibrin-dependent activation. The amino acid sequence of the TPA mutant is at least 65% identical to SEQ ID NO: 1 or SEQ ID NO: 2. The TPA mutant may thus also have homologies with these sequences greater than 65%, e.g., 70%, 75%, 80%, 85%, 90%, 95% and so on. A non-limiting example of a TPA mutant is reteplase, which is a TPA deletion mutant which has 67.7% of the residues found in full length TPA. An alternative non-limiting example of a TPA mutant is tenecteplase, which is a TPA substitution mutant which is a 527 amino acid glycoprotein developed by introducing the following modifications to the complementary DNA (cDNA) for natural human tPA: a substitution of threonine 103 with asparagine, and a substitution of asparagine 117 with glutamine, both within the kringle 1 domain, and a tetra-alanine substitution at amino acids 296-299 in the protease domain. In some embodiments, the amino acid sequence of the human TPA is SEQ ID NO: 1 or SEQ ID NO: 2.

It is an object of the present invention to produce an antibody molecule specific for the TPA with sub-nanomolar dissociation constant (for a review on the definitions and measurements of antibody-antigen affinity, see Neri et al. (1996). Trends in Biotechnol. 14, 465-470).

The present invention provides an antibody molecule that binds specifically to a human TPA or a TPA mutant to inhibit degradation of human fibrin clots, wherein the antibody has sub-nanomolar affinity to inhibit fibrin-dependent plasminogen activation with an IC50<5 nM, and wherein the amino acid sequence of said TPA mutant has at least 65% identity to SEQ ID NO: 1 or SEQ ID NO: 2; wherein the antibody comprises a heavy chain variable domain with a CDR1 selected from the group consisting of SEQ ID NOs: 3 and 4, a CDR2 selected from the group consisting of SEQ ID NO: 5 and 6, and a CDR3 selected from the group consisting of SEQ ID NO: 7 and 8, and a light chain variable domain with a CDR1 selected from the group consisting of SEQ ID NO: 9 and 10, a CDR2 selected from the group consisting of SEQ ID NO: 11 and 12, and a CDR3 of SEQ ID NO: 13.

In one embodiment, the antibody molecule of the present invention comprises a heavy chain variable domain with a CDR1 of SEQ ID NO: 3, a CDR2 of SEQ ID NO: 5, and a CDR3 of SEQ ID NO: 7, and a light chain variable domain with a CDR1 of SEQ ID NO: 9, a CDR2 of SEQ ID NO: 11, and a CDR3 of SEQ ID NO: 13.

In a further embodiment, the antibody molecule of the present invention comprises a heavy chain variable domain selected from the group consisting of SEQ ID NOs: 14 to 28 and a light chain variable domain selected from the group consisting of SEQ ID NOs: 29 and 30.

In a further embodiment, the antibody molecule of the present invention comprises a heavy chain variable domain selected from the group consisting of SEQ ID NOs: 14 to 28, and a light chain variable domain of SEQ ID NO: 29.

In one embodiment, the antibody molecule of the present invention comprises a heavy chain variable domain of SEQ ID NO: 14, and a light chain variable domain of SEQ ID No: 29, or a heavy chain variable domain of SEQ ID NO: 15, and a light chain variable domain of SEQ ID No: 29, or a heavy chain variable domain of SEQ ID NO: 14, and a light chain variable domain of SEQ ID No: 30, or a heavy chain variable domain of SEQ ID NO: 15, and a light chain variable domain of SEQ ID No: 30.

In one embodiment, the antibody molecule of the present invention has a heavy chain comprising SEQ ID NO: 40 or SEQ ID NO: 41, and a light chain comprising SEQ ID NO: 42.

The term "mutant" as used herein includes a peptide with a sequence substantially similar to the sequence of TPA. It is known in the art that a substantially similar amino acid sequence to a reference peptide may yield a mutant peptide with no substantial change in physiological, chemical, or functional properties compared to the reference peptide. In such a case, the reference and mutant peptides would be considered "substantially identical" polypeptides. Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as BLAST-P, BLAST-N, or FASTA-N, or any other appropriate software that is known in the art. The substantially identical sequences of the present invention may be at least 65% identical. In another example, the substantially identical sequences may be at least 65, 70, 75, 80, 85, 90, 95, or 100% identical at the amino acid level to sequences described herein.

Antibodies (also known as immunoglobulins, abbreviated Ig) are gamma globulin proteins that can be found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies can bind, by non-covalent interaction, to other molecules or structures known as antigens. This binding is specific in the sense that an antibody will only bind to a specific structure with high affinity. The unique part of the antigen recognized by an antibody is called an epitope, or antigenic determinant. The part of the antibody binding to the epitope is sometimes called paratope and resides in the so called variable domain, or variable region (Fv) of the antibody. The variable domain comprises three so-called complementary-determining region (CDR's) spaced apart by framework regions (FR's).

Within the context of this invention, reference to CDRs is based on the definition of Chothia (Chothia and Lesk, J. Mol. Biol. 1987, 196: 901-917), together with Kabat (E. A. Kabat, T. T. Wu, H. Bilofsky, M. Reid-Miller and H. Perry, Sequence of Proteins of Immunological Interest, National Institutes of Health, Bethesda (1983)).

Antibodies have been developed to be useful in medicine and technology. Thus, in the context of the present invention the terms "antibody molecule" or "antibody" (used synonymously herein) do not only include antibodies as they may be found in nature, comprising e.g. two light chains and two heavy chains, or just two heavy chains as in camelid species, but furthermore encompasses all molecules comprising at least one paratope with binding specificity to an antigen and structural similarity to a variable domain of an immunoglobulin.

The term "antibody" (Ab) as used herein includes monoclonal antibodies, polyclonal antibodies, multispecific antibodies and antibody fragments, as long as they exhibit the desired biological activity. The term "polyclonal antibody" as used herein refers to a collection of antibody molecules with different amino acid sequences and may be obtained from the blood of vertebrates after immunization with the antigen by processes well-known in the art. The term "monoclonal antibody" as used herein refers to an antibody obtained from a population of substantially homogeneous antibodies, i.e., the individual antibodies that make up the population are identical except for possible naturally occurring mutations. Monoclonal antibodies are highly specific, being directed against a single antigenic site. For example, the monoclonal antibodies useful in the present invention may be prepared by the hybridoma methodology from a hybrid cell line (called hybridoma) representing a clone of a fusion of a specific antibody-producing B cell with a myeloma (B cell cancer) cell described by Kohler et al., Nature, 256:495 (1975), or may be made using recombinant DNA methods in bacterial, eukaryotic animal or plant cells (see, e.g., U.S. Pat. No. 4,816,567). Additionally, the "monoclonal antibodies" may also be isolated from phage antibody libraries using the techniques described in Clackson et al., Nature, 352:624-628 (1991) and Marks et al., J. Mol. Biol., 222:581-597 (1991), for example.

For application in man, it is often desirable to reduce immunogenicity of antibodies originally derived from other species, such as mouse. This can be done by construction of chimeric antibodies, or by a process called "humanization". In this context, a "chimeric antibody" is understood to be an antibody comprising a sequence part (e.g. a variable domain) derived from one species (e.g. mouse) fused to a sequence part (e.g. the constant domains) derived from a different species (e.g. human). A "humanized antibody" is an antibody comprising a variable domain originally derived from a non-human species, wherein certain amino acids have been mutated to resemble the overall sequence of that variable domain more closely to a sequence of a human variable domain. Methods of chimerisation and humanization of antibodies are known in the art (Billetta R, Lobuglio A F. "Chimeric antibodies". Int Rev Immunol. 1993; 10(2-3):165-76; Riechmann L, Clark M, Waldmann H, Winter G (1988). "Reshaping human antibodies for therapy" *Nature:* 332:323).

The creation and development of monoclonal antibodies/monoclonal antibody fragments (mAbs/Fabs) drug candidate molecules is however complex. Despite the fact that many techniques used in the production of mAbs/Fabs have been standardized, each Mab/Fab is unique, due to its specific structure derived from its origin of binding to a specific antigen target. In addition, they "are far more complex to produce and characterize than small molecules as they are 200-1000× larger, structurally more complex, and highly sensitive to their manufacturing conditions." (Kizhedath A, Wilkinson S and Glassey J. Applicability of predictive toxicology methods for monoclonal antibody therapeutics: status Quo and scope. Arch Toxicol 2017; 91:1595-1612.). Another layer of complexity is added when one considers the unique changes required to each candidate molecule to optimize its pharmacodynamic and pharmacokinetic properties, while reducing its potential toxicokinetic properties, such as immunogenicity, off-target or immuno-stimulating (cytokine storm) effects.

Furthermore, technologies have been developed for creating antibodies based on sequences derived from the human genome, for example by phage display or using transgenic animals (WO 90/05144; D. Marks, H. R. Hoogenboom, T. P. Bonnert, J. Mccafferty, A. O. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1 (2):189-203; Lonberg N, Huszar D. "Human antibodies from transgenic mice". Int Rev Immunol. 1995; 13(1):65-93; Bruggemann M, Taussig M J. "Production of human antibody repertoires in transgenic mice". Curr Opin Biotechnol. 1997 August; 8(4):455-8.). Such antibodies are "human antibodies" in the context of the present invention.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)).

The term "antibody" (Ab) as used herein also includes antibody fragments. An "antibody fragment" is a portion of an intact antibody, preferably the antigen binding or variable region of the intact antibody. Examples of antibody fragments include but are not limited to: Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Such fragments may be obtained by fragmentation of immunoglobulins e.g. by proteolytic digestion, or by recombinant expression of such fragments. For example, immunoglobulin digestion can be accomplished by means of routine techniques, e.g. using papain or pepsin (WO 94/29348), or endoproteinase Lys-C (Kleemann, et al, Anal. Chem. 80, 2001-2009, 2008). Papain or Lys-C digestion of antibodies typically produces two identical antigen binding fragments, so-called Fab fragments, each with a single antigen binding site, and a residual Fc fragment. Pepsin treatment yields an F(ab')2. Methods of producing Fab molecules by recombinant expression in host cells are outlined in more detail below.

A number of technologies have been developed for placing variable domains of immunoglobulins, or molecules derived from such variable domains, in a different structural context. Those should be also considered as "antibody molecules" in accordance with the present invention. In general, these antibody molecules are smaller in size compared to immunoglobulins, and may comprise a single amino acid chain or be comprised of several amino acid chains. For example, a single-chain variable fragment (scFv) is a fusion of the variable regions of the heavy and light chains of immunoglobulins, linked together with a short linker, usually serine (S) or glycine (G) (WO 88/01649; WO 91/17271; Huston et al; International Reviews of Immunology, Volume 10, 1993, 195-217). "Single domain antibodies" or "nanobodies" include an antigen-binding site in a single Ig-like domain (WO 94/04678; WO 03/050531, Ward et al., Nature. 1989 Oct. 12; 341 (6242):544-6; Revets et al., Expert Opin Biol Ther. 5(1):111-24, 2005). One or more single domain antibodies with binding specificity for the same or a different antigen may be linked together. Diabodies are bivalent antibody molecules consisting of two amino acid chains comprising two variable domains (WO 94/13804, Holliger et al., Proc Natl Acad Sci USA. 1993 Jul. 15; 90(14):6444-8). Other examples for antibody-like molecules are immunoglobulin super family antibodies (IgSF; Srinivasan and Roeske, Current Protein Pept. Sci. 2005, 6(2): 185-96). Alternatively, Small Modular Immunopharmaceuticals (SMIP) comprises a Fv domain linked to single-chain hinge and effector domains devoid of the constant domain CH1 (WO 02/056910).

Thus, an antibody molecule according to the present invention may be a polyclonal antibody, a monoclonal antibody, a human antibody, a humanized antibody, a chimeric antibody, a fragment of an antibody, in particular a Fab, Fab', or F(ab')2 fragment, a single chain antibody, in particular a single chain variable fragment (scFv), a Small Modular Immunopharmaceutical (SMIP), a domain antibody, a nanobody, a diabody, or a Designed Ankyrin Repeat Protein (DARPin).

In one embodiment, the antibody molecule of the present invention is a humanized antibody or a fragment of a humanised antibody, in particular a Fab, Fab', or F(ab')2 fragment, a single chain antibody, in particular a single chain variable fragment (scFv), a Small Modular Immunopharmaceutical (SMIP), a domain antibody, a nanobody, a diabody, or a Designed Ankyrin Repeat Protein (DARPin).

In a further embodiment, the antibody molecule of the present invention is a humanized antibody or a fragment of a humanised antibody, in particular a Fab, Fab', or F(ab')2 fragment.

The variable domains disclosed above may each be fused to an immunoglobulin constant domain, preferably of human origin. Thus, the heavy chain variable domain may be fused to a CH1 domain (a so-called Fd fragment), and the light chain variable domain may be fused to a CL domain.

In one embodiment, the antibody molecule of the present invention is a Fab molecule, in particular a humanised Fab molecule, having a Fd fragment comprising SEQ ID NO: 31 or SEQ ID NO: 32, and a light chain comprising SEQ ID NO: 33.

Fab molecules can be generated from full-length antibody molecules by enzymatic cleavage, in which the whole antibody is cleaved by an enzyme such as papain, pepsin, or ficin. The advantage of this approach is that platform processes for robust and efficient fermentation and purification are applicable which are amenable for up-scaling and high yields at the desired product quality. For purification, affinity chromatography using a recombinant Protein A resin can be used to separate the Fab fragment from the Fc (fragment that crystallizes) and residual intact antibody. Using protein A affinity chromatography typically results in high purities.

Alternatively, nucleic acids encoding Fab constructs may be used to express such heavy and light chains in host cells, like *E. coli, Pichia pastoris*, or mammalian cell lines (e.g., CHO, HEK293, or NSO). Processes are known in the art which allow proper folding, association, and disulfide bonding of these chains into functional Fab molecules comprising a Fd fragment and a light chain (Burtet et al., J. Biochem. 2007, 142(6), 665-669; Ning et al., Biochem. Mol. Biol. 2005, 38: 204-299; Quintero-Hernandez et al., Mol. Immunol. 2007, 44: 1307-1315; Willems et al. J. Chromatogr. B. Analyt. Technol. Biomed. Life Sci. 2003; 786:161-176.).

In one embodiment, the antibody molecule of the present invention is a scFv molecule.

The variable domains disclosed herein may be fused to each other with a suitable linker peptide, e.g. selected from the group consisting of SEQ ID Nos: 33, 34, 35, or 36. The construct may comprise these elements in the order, from N terminus to C terminus, (heavy chain variable domain)-(linker peptide)-(light chain variable domain), or (light chain variable domain)-(linker peptide)-(heavy chain variable domain).

In a further embodiment, the antibody molecule of the present invention is a scFv wherein the heavy chain variable domain and the light chain variable domain are linked to each other through a linker peptide selected from the group consisting of SEQ ID NO: 34, SEQ ID NO: 35, SEQ ID NO: 36, and SEQ ID NO: 37.

In a further embodiment, the antibody molecule of the present invention comprises SEQ ID NO: 38, or SEQ ID NO:39.

Processes are known in the art which allow recombinant expression of nucleic acids encoding scFv constructs in host cells (like *E. coli, Pichia pastoris*, or mammalian cell lines, e.g. CHO or NSO), yielding functional scFv molecules (see e.g. Rippmann et al., Applied and Environmental Microbiology 1998, 64(12): 4862-4869; Yamawaki et al., J. Biosci. Bioeng. 2007, 104(5): 403-407; Sonoda et al., Protein Expr. Purif. 2010, 70(2): 248-253).

The antibody molecule of the present invention may be fused (as a fusion protein) or otherwise linked (by covalent or non-covalent bonds) to other molecular entities having a desired impact on the properties of the antibody molecule.

For example, it may be desirable to improve pharmacokinetic properties of antibody molecules, or stability e.g. in body fluids such as blood, in particular in the case of single chain antibodies or domain antibodies. A number of technologies have been developed in this regard, in particular to prolong half-life of such antibody molecules in the circulation, such as pegylation (WO 98/25971; WO 98/48837; WO 2004081026), fusing or otherwise covalently attaching the antibody molecule to another antibody molecule having affinity to a serum protein like albumin (WO 2004041865; WO 2004003019), or expression of the antibody molecule as fusion protein with all or part of a serum protein like albumin or transferrin (WO 01/79258).

In a further aspect of the invention, the antibody molecule is capable of neutralizing the activity of the fibrinolytic agent. That is, upon binding to the antibody molecule, the TPA is no longer able to exert its fibrinolytic activity through plasminogen activation, or exerts this activity at a significantly decreased magnitude. Preferably, the fibrinolytic activity is decreased at least 2-fold, 5-fold, 10-fold, or 100-fold upon antibody binding, as determined in an activity assay (Longstaff C, Whitton C M. A proposed reference method for plasminogen activators that enables calculation of enzyme activities in SI units. J Thromb Haemost. 2004; 2: 1416-1421) which is appropriate, and particularly a clotting assay that is sensitive to fibrin degratory factors, such as the measurement of D-D-Dimer (Gebhardt J, Kepa S, Hofer S, Koder S, et al. Fibrinolysis in patients with mild-to-moderate bleeding tendency or unknown cause. Ann Hematol 2017; 96:489-495).

For manufacturing the antibody molecules of the invention, the skilled artisan may choose from a variety of methods well known in the art (Norderhaug et al., J Immunol Methods 1997, 204 (1): 77-87; Kipriyanow and Le Gall, Molecular Biotechnology 26: 39-60, 2004; Shukla et al., 2007, J. Chromatography B, 848(1): 28-39).

Human TPA and mutants are well-known in the art, as outlined above. In this context, TPA includes TPA and mutants.

TPA-induced brain and systemic bleeding in vivo is blocked by potent synergistic inhibitors of TPA's fibrin-dependent plasminogen activation. This implies that haemorrhage is related to TPA's fibrin-targeted mechanism of plasminogen activation and that targeted inhibitors of this process may serve as specific antidotes for TPA associated haemorrhage. TPA therapy is beneficial in ischemic stroke and myocardial infarction, but in some patients it is complicated by serious or fatal bleeding in the brain and at other sites. Fear of TPA-induced bleeding has limited the therapeutic use of TPA. In humans, TPA-induced haemorrhage and adverse outcomes are more frequent after prolonged ischemia. Similarly, in experimental stroke, after prolonged ischemia, TPA reproducibly causes brain haemorrhage, breakdown of the blood brain barrier and enhanced neuronal cell death. In non-thrombotic models of stroke there is evidence that TPA may exert toxic effects through mechanisms, such as PDGF-CC cleavage, etc. that do not require plasminogen activation or affect fibrinolytic activity (Su E J, Fredriksson L, Geyer M, et al. Activation of PDGF-CC by tissue plasminogen activator impairs blood-brain barrier integrity during ischemic stroke. Nat Med. 2008; 14:731-737). Under pathological conditions like myocardial ischemia and stroke, the fibrinolytic activity of therapeutic TPA is enhanced by increased levels of circulating fibrin fragments (e.g., D-dimer), which may enhance the bleeding process. (Barber M, Langhorne P, Rumley A, Lowe G D, Stott D J. D-dimer predicts early clinical progression in ischemic stroke: confirmation using routine clinical assays. *Stroke.* 2006; 37:1113-1115.)

In addition to therapeutic use of TPA, elevated TPA levels have been associated with excessive systemic bleeding. TPA-induced bleeding has been suspected in patients' post-cardiopulmonary bypass. (Manji R A, Grocott H P, Leake J, et al. Seizures following cardiac surgery: the impact of tranexamic acid and other risk factors. Can J Anaesth. 2012; 59:6-13.) In a similar fashion, in disease conditions such as liver failure and transplantation, high levels of circulating TPA have been linked to bleeding. (Leiper K, Croll A, Booth N A, Moore N R, Sinclair T, Bennett B. Tissue plasminogen activator, plasminogen activator inhibitors, and activator-inhibitor complex in liver disease. J Clin Pathol. 1994; 47:214-217). Fibrinolytic inhibitors (e.g., tranexamic acid, ε-aminocaproic acid, aprotinin, etc.) reduce the risk of transfusion after surgery (Bayes-Genis A, Mateo J, Santalo M, et al. D-Dimer is an early diagnostic marker of coronary ischemia in patients with chest pain. Am Heart J. 2000; 140:379-384). However, these agents have broad inhibitory effects on other pathways and associated toxicities. For example, tranexamic acid increases seizures risk after cardiac surgery. (Manji R A, Grocott H P, Leake J, et al. Seizures following cardiac surgery: the impact of tranexamic acid and other risk factors. *Can J Anaesth.* 20 I2; 59:6-13). Broad inhibition of fibrinolysis may carry a risk of subsequent thrombotic episodes such stroke, thromboembolism. (Fergusson D A, Hebert P C, Mazer C D, et al. A comparison of aprotinin and lysine analogues in high-risk cardiac surgery. *N Engl J Med.* 2008; 358:2319-2331). This concern was magnified by the unexpected finding that aprotinin use increased mortality following cardiac surgery (ibid).

Severe trauma or trauma producing poly-organ damage produces a hyperfibrinolytic state that is mediated by elevated endogenous TPA levels (Cardenas J C, Matijevic N, Baer L A, Holcomb J B, Cotton B A, Wade C E. Elevated tissue plasminogen activator and reduced plasminogen activator inhibitor promote hyperfibrinolysis in trauma patients. Shock 2014; 41(6):514-21). Thus, inhibition of elevated endogenous TPA by an antibody agent could normalize fibrinolysis and prevent the coagulopathy seen in these conditions. Tranexamic acid has been studied in severely injured trauma patients with hyperfibrinolysis caused by elevated endogenous TPA, producing increased 6 hour survival but not affecting long term survival (Khan M, Jehan F, Bulger E M, et al. Severely injured trauma patients with admission hyperfibrinoloysis: Is there a role of tranexamic acid? Findings from the PROPPR trial. J Trauma Acute Care Surg 2018; 85(5):851-857).

The use of anti-fibrinolytic agents for treating TPA-induced haemorrhage is still very limited, possibly because these agents are known to interfere with other biochemical pathways. PAI-I or PAI-I mutants have been shown to suppress TPA-induced bleeding after injury. However, in addition to inhibiting TPA, PAI-I inhibits uPA, and several other proteases. Through its non-proteinase interactions with vitronectin, heparin, members of the low-density lipoprotein-receptor family and other molecules, PAI-I has 'pleiotropic' effects on numerous other biological processes and has been implicated in the pathophysiology of several disease processes. Thus PAI-I has roles in angiogenesis, apoptosis, cell migration and cancer that involve both inhibitory and non-inhibitory functions.

In one aspect, the present invention provides a pharmaceutical composition comprising an antibody molecule of the present invention and a pharmaceutically acceptable carrier.

In a further aspect, the present invention provides an antibody molecule of the present invention for use as a medicament.

In a further aspect, the present invention provides an antibody molecule of the invention for use in the treatment or prevention of TPA induced haemorrhage.

As described above, elevated levels of TPA may be as a result of exogenous or endogenous processes i.e. specific administration of TPA or as a result of elevated levels of TPA being generated in vivo, for example following cardiopulmonary bypass. In this context, 'TPA induced haemorrhage' includes haemorrhage induced by elevated levels of TPA resulting from exogenous or endogenous processes.

The antibody molecule inhibits fibrinolysis induced by TPA. In some embodiments, the antibody molecule inhibits the initiation of fibrinolysis. In some embodiments, the antibody molecule inhibits fibrinolysis in progress.

In one embodiment, the present invention provides an antibody molecule of the invention for use in the treatment or prevention of systemic haemorrhage, in particular brain haemorrhage and systemic bleeding after tissue plasminogen activator treatment, more specifically after TPA treatment for ischemic stroke.

In an alternative embodiment, the present invention provides an antibody molecule of the invention for use in the treatment or prevention of systemic haemorrhage in subjects wherein endogenous TPA is elevated, including, but not limited to, as a result of prolonged coronary artery bypass surgeries, liver transplantation, severe or poly-trauma, heatstroke, and near drowning.

In a further aspect, the present invention provides a method of treatment or prevention of TPA induced haemorrhage, comprising administering an effective amount of an antibody molecule of the invention to a subject in need thereof.

In one embodiment, the present invention provides a method of treatment or prevention of systemic haemorrhage, in particular brain haemorrhage and systemic bleeding after tissue plasminogen activator treatment, more specifically after TPA treatment for ischemic stroke, comprising administering an effective amount of an antibody molecule of the invention to a subject in need thereof.

In an alternative embodiment, the present invention provides a method of treatment or prevention of systemic haemorrhage in subjects wherein endogenous TPA is elevated, including, but not limited to, as a result of prolonged coronary artery bypass surgeries, liver transplantation, severe or poly-trauma, heatstroke, or near drowning, comprising administering an effective amount of an antibody molecule of the invention to a subject in need thereof.

In a further aspect, the present invention provides a kit comprising an antibody molecule of the present invention, or a pharmaceutical composition thereof.

In one embodiment the kit comprises:

(a) an antibody of the present invention or a pharmaceutical composition thereof;
(b) a container; and
(c) a label.

In one embodiment the kit comprises an antibody of the present invention or a pharmaceutical composition thereof and human tissue plasminogen activator (TPA) or a TPA mutant wherein the amino acid sequence of said TPA mutant has at least 65% identity to SEQ ID NO: 1 or SEQ ID NO: 2.

In a further embodiment, the human tissue plasminogen activator (TPA) or TPA mutant is selected from alteplase (Activase®, Actilyse®; rtPA), reteplase (Retavase®, Rapilysin®) and tenecteplase (TNKase®; TNK-tPA).

In a further embodiment, the kit comprises:

(a) an antibody of the present invention or a pharmaceutical composition thereof;
(b) a pharmaceutical composition comprising human tissue plasminogen activator (TPA) or TPA mutant selected from alteplase (Activase®, Actilyse®; rtPA), reteplase (Retavase®, Rapilysin®) and tenecteplase (TNKase®; TNK-tPA);
(c) a container; and
(d) a label.

In a further embodiment, the kit comprises:

(a) a first pharmaceutical composition comprising human tissue plasminogen activator (TPA) or TPA mutant selected from alteplase (Activase®, Actilyse®; rtPA), reteplase (Retavase®, Rapilysin®) and tenecteplase (TNKase®; TNK-tPA);
(b) a second pharmaceutical composition comprising antibody of the present invention;
(c) instructions for separate administration of the first and second pharmaceutical compositions to a subject, wherein the first and second pharmaceutical compositions are contained in separate containers and the second pharmaceutical composition is administered to a subject requiring treatment or prevention of systemic haemorrhage after TPA treatment.

In this context, a 'subject requiring treatment' is one displaying symptoms of severe haemorrhage and a 'subject requiring prevention' is one displaying no symptoms of severe haemorrhage, but judged as high risk by a treating physician.

In one aspect, the present invention provides a method of manufacturing an antibody molecule of the present invention, comprising:

(a) providing a host cell comprising one or more nucleic acids encoding said antibody molecule in functional association with an expression control sequence,
(b) cultivating said host cell, and
(c) recovering the antibody molecule from the cell culture.

A "purified or isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

"Prevention" of a condition or disorder refers to delaying or preventing the onset of a condition or disorder or reducing its severity, as assessed by the appearance or extent of one or more symptoms of said condition or disorder.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, a subject is "in need of" a treatment if such subject would benefit biologically, medically or in quality of life from such treatment.

As used herein, a subject wherein 'endogenous TPA is elevated' refers to a subject wherein the plasma concentration of endogenous TPA is increased with respect to baseline levels. The World Health Organization (WHO/BS/07.2068, 2007) quotes normal plasma levels of tPA as <10 ng/mL with most values reported at ~4 ng/mL. 5-10-fold elevations have been reported in subjects with hyperfibrinolysis (Chapman et al., Overwhelming tPA Release, not PAI-1 Degradation, is Responsible for Hyperfibrinolysis in Severely Injured Trauma Patients, *J Trauma Acute Care Surg.* 2016 January; 80(1): 16-25; Duque et al., Pathophysiological Response to Trauma-Induced Coagulopathy: A Comprehensive Review, 2019 Anesthesia & Analgesia: Oct. 15, 2019—Volume Publish Ahead of Print—Issue—p doi: 10.1213/ANE.0000000000004478).

The compositions of the invention may include an "effective amount" or "therapeutically effective amount" or a "prophylactically effective amount" of an antibody or antigen-binding portion of the invention. These terms are used interchangeably. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the subject, and the ability of the antibody or antibody portion to elicit a desired response in the subject. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

In a further aspect, the present invention provides a method for identifying molecules that can inhibit TPA-induced fibrinolysis of human clots. The method includes the steps of: providing an antibody molecule of the present invention that specifically binds to TPA and inhibits TPA-induced fibrinolysis of human clots, affixing the antibody molecule to a surface, providing TPA and introducing an agent to the TPA that blocks the non-specific binding regions of TPA, introducing a candidate molecule to the TPA, introducing the TPA to the antibody molecule, determining if the candidate molecule has bound to the epitope of the TPA where the antibody molecule had bound to the TPA, and identifying any candidate molecule binding to the epitope as a molecule that can inhibit TPA-induced fibrinolysis of human clots. In one example of the embodiment, an antibody molecule of the invention is immobilized in the wells of a microtiter plate. Non-specific protein binding sites are blocked. A mixture of TPA and the potential new inhibitor molecule, pre-incubated together are added to the wells containing immobilized antibody molecule. After an hour, wells are washed and polyclonal anti-TPA antibody coupled to peroxidase is added. After an hour, wells are washed and the peroxidase substrate TMB is added and the A370 is monitored. Wells with reduced A370 contain molecules that compete with the antibody molecule of the invention for TPA binding and are thus prime candidates as specific TPA inhibitors. That will be confirmed in detailed studies of human clot lysis initiated by TPA.

The following examples are intended to illustrate the invention and are not to be construed as being limitations thereon.

Abbreviations used are those conventional in the art. If not defined, the terms have their generally accepted meanings.

Abbreviations and acronyms used herein include the following:

Expi293 Human Embryonic Kidney (HEK293 High density/serum free) cells
bp base pairs
° C. Centigrade
MEM Minimal Essential Medium
DLS Dynamic light scattering
DNA Deoxyribonucleic acid
ELISA Enzyme linked immuno-adsorbent assay
EC50 Concentration of antibody providing half-maximal response
ECD extracellular domain
g grams
HRP Horseradish peroxidase
IgG Immunoglobulin-G
LIC Ligase independent cloning
min minute
MALS Multi-angle light scattering
nm nanometre
OD optical density
PBS Phosphate Buffered Saline
PCR Polymerase chain reaction
RT Room Temperature
s second
SEC Size exclusion chromatography
TMB 3,3',5,5'-tetramethylbenzidine
UV Ultra Violet
VCI vernier, canonical and interface residues
VH Immunoglobulin heavy chain variable region
VK Immunoglobulin kappa light chain variable region Nucleotides:

| | |
|---|---|
| A | Adenine |
| C | Cytosine |
| G | Guanine |
| T | Thymine |
| K | G or T (IUPAC convention) |
| M | A or C (IUPAC convention) |
| R | A or G (IUPAC convention) |
| S | C or G (IUPAC convention) |
| V | A or C or G (IUPAC convention) |
| W | A or T (IUPAC convention) |
| Y | C or T (IUPAC convention) |

Amino Acids:

| | | | |
|---|---|---|---|
| Ala (A) | Alanine | Met (M) | Methionine |
| Cys (C) | Cysteine | Asn (N) | Asparagine |
| Asp (D) | Aspartic acid | Pro (P) | Proline |
| Glu (E) | Glutamic acid | Gln (Q) | Glutamine |
| Phe (F) | Phenylalanine | Arg (R) | Arginine |
| Gly (G) | Glycine | Ser (S) | Serine |
| His (H) | Histidine | Thr (T) | Threonine |
| Ile (I) | Isoleucine | Val (V) | Valine |
| Lys (K) | Lysine | Trp (W) | Tryptophan |
| Leu (L) | Leucine | Tyr (Y) | Tyrosine |

Materials

Culture Reagents
Article UK Supplier Catalog Number
- ExpiCHO Expression Medium Invitrogen A29100-01
- Expi293 expression media Invitrogen A1435102
- Penicillin & Streptomycin Invitrogen 15140-148
- Opti-MEM® I Invitrogen 11058021
- SOC Invitrogen 15544-034
- Trypan Blue BioRad 145-0013
- ExpiFectamine CHO kit 1 L Invitrogen A29129
- Expifectamine 293 kit 1 L Invitrogen A14524
- Penicillin & Streptomycin Invitrogen 15140-148
- Opti-MEM® 1 Invitrogen 11058021
- SOC Invitrogen 15544-034
- Trypan Blue BioRad 145-0013
- ExpiFectamine CHO kit 1 L Invitrogen A29129
- Expifectamine 293 kit 1 L Invitrogen A14524

Immunology and Molecular Biology Reagents
Article UK Supplier Catalog Number
- 1st strand synthesis kit GE Life Sciences 27-9261-01
- Agarose (UltraPure™) Invitrogen 15510-027
- Albumin bovine (BSA) Sigma A3294
- Bam HI NEB R0136S
- BfuA1 NEB R0701S
- dNTPS solution set NEB N04465
- e-gel 2% agarose G521802
- e-gel 2% agarose double comb Invitrogen G6018-02
- Goat anti-human IgG (Fc fragment specific) antibody Stratech Scientific 109-005-098
- Goat anti-human Fcγ specific) Peroxidase Conjugate Jackson 109-035-098
- Goat anti-human kappa chain horseradish peroxidase conjugate Sigma A7164
- Goat anti-mouse F(ab')2-peroxidase conjugate Jackson 115-036-006
- HBS-EP+ Buffer 10× GE Healthcare BR100669
- Human Antibody Capture Kit GE Healthcare BR-1008-39
- Human IgG1/kappa antibody. Sigma I5154
- Kanamycin Invitrogen 11815024
- K-Blue HRP substrate SkyBio 308176
- Mouse Antibody Capture Kit GE Healthcare BR-1008-38
- Oligonucleotides Sigma n.a.
- PBS Tablets Sigma P4417
- Phusion Flash High-Fidelity PCR Master Mix Fisher Scientific F-5485
- PureYield Plasmid Maxi kit Promega A2393
- Q5 Site-Directed Mutagenesis Kit NEB E0554S
- QIAGEN Gel Extraction kit Qiagen 28704
- QIAprep Spin Miniprep Kit Qiagen 27106
- QIAquick PCR Purification Kit (250) 28106
- Quick-Load® 100 bp DNA Ladder NEB N04675
- Quick-Load® 1 kb DNA Ladder NEB N04685
- QuikChange Lightning Site-Directed Mutagenesis Kit, 10 Rxn. Agilent 210518
- Red Stop Solution (For K Blue) SkyBio Ltd 301475
- RNeasy Mini Kit Qiagen 74106
- Sensor Chip CM5 GE Healthcare BR100399
- Subcloning Efficiency™ TOP10™ Chemically Competent *E. coli* Invitrogen 404003
- SYBR Safe DNA gel stain Invitrogen S33102
- SYPRO Orange
- T4 DNA Polymerase NEB M0203S
- Tween® 20 Sigma P9416-100 ML 1.0 Sequence Determination of Antibody 1.1 Monoclonal Antibody Generation C57BL/6J mice (Jackson Laboratory, Bar Harbor, ME) were immunized with recombinant human TPA (Genentech) followed by fusion of splenocytes isolated from the immunized mouse with myeloma cells using the conventional hybridoma techniques (Nelson P N, Reynolds G M, Waldron E E, Ward E, Giannopoulos K, Murray P G. Monoclonal antibodies. Mol Pathol. 2000; 53: 111-117). Microplate ELISA assays were performed to screen positive clones as described below. Positive clones were further subcloned by limited dilution to create stable monoclonal antibody (mAb). All cell cultures were maintained in DMEM medium, supplemented with 5% fetal bovine serum, 2 mmol/L L-glutamine, and 1% penicillin-streptomycin (Invitrogen) in a humidified 5% $CO_2$/95% air incubator at 37° C. Mouse mAb was purified from culture medium with goat anti-mouse IgG agarose (Invitrogen) and further characterized with mouse antibody isotyping kit (Zymed Laboratory).

1.1.1 ELISA Assay for Detecting TPA mAb Binding

To screen positive TPA binding clones, microplates were coated with 1-211 g/ml TPA in phosphate buffered saline (PBS, Invitrogen) for one hour at room temperature, followed by blocking with 1% bovine serum albumin (BSA, Invitrogen) in PBS for one hour. After that, mouse serum, hybridoma cell culture supernatant, or 2-5 μg/ml purified anti-TPA mAb in PBS solution was loaded and incubated for one hour. The bound mAb was detected by horse radish peroxidase (HRP) conjugated goat antimouse IgG (Santa Cruz Biotechnology, Inc,) with TMB substrate (3,3',5,5'-tetramethylbenzidine (TMB) substrate, Pierce Plus activated HRP conjugation kit (Fisher Scientific)). In some runs, 3 μg/ml human PAI-1 was incubated in TPA coated BSA blocked wells before the addition of anti-TPA mAb to examine the binding between mAb and TPA-PAI-1 complex; complex formation was confirmed by detection of bound PAI-1 with mouse anti-human PAI-1 mAb. TPA and anti-TPA mAb binding constants were estimated by saturation binding experiment with ELISA assay. Briefly, 7.5 μg/ml purified anti-TPA mAb in PBS were coated on microplate for one hour at room temperature, followed by blocking with 1% BSA in PBS. Varying concentrations of human TPA (0-4 μg/ml) were then loaded in human serum prequenched with 20 μM PPACK (d-Phe-Pro-Arg chloromethylketone (PPACK) (Calbiochem)), and 200 kallikrein inhibitor units aprotinin. Bound TPA was detected with HRP-conjugated mouse anti-human TPA polyclonal antibody, followed by TMB substrate. The reaction was monitored at A370 nm within the dynamic range of the microplate reader. Binding constants were calculated using Graphpad Prism Software (La Jolla, CA). To test if anti-TPA mAb compete with each other for binding with TPA, 211 g/ml TPA was coated on microplates. After blocking with I % BSA in PBS, varying concentration of HRP-labeled anti-TPA mAb were added. After washing, the bound mAb were detected with TMB substrate. In some wells, varying concentrations of purified anti-TPA mAb was added to a fixed amount of HRP-labeled anti-TPA mAb to compete the binding for coated TPA. The percent inhibition of binding was calculated based on the difference between bound HRP labeled mAb in the absence and presence of purified anti-TPA mAb.

1.2. RNA Preparation from Hybridoma Cells

Mouse hybridoma cells generated according to 1.1 and identified as TPAi-1, were pelleted and washed with PBS. The pellet was processed using the Qiagen RNeasy Kit to isolate RNA following the manufacturer's protocol (Section 1.2.1).

1.2.1 RNeasy Mini Protocol for Isolation of Total RNA (Qiagen)

1. Disrupt cells by addition of Buffer RLT. For pelleted cells, loosen the cell pellet thoroughly by flicking the tube. Add Buffer RLT (600 μl), and proceed to step 2. Note: Incomplete loosening of the cell pellet may lead to inefficient lysis and reduced yields.

2. Homogenize cells passing the lysate at least 5 times through an 18-20-gauge needle fitted to an RNase-free syringe.

3. Add 1 volume of 70% ethanol to the homogenized lysate, and mix thoroughly by pipetting. Do not centrifuge. The volume of lysate may be less than 350 μl or 600 μl due to loss during homogenization.

4. Transfer up to 700 μl of the sample, including any precipitate that may have formed, to an RNeasy spin column placed in a 2 ml collection tube. Close the lid gently, and centrifuge for 15 s at ≥8000×g. Discard the flow-through. Reuse the centrifuge tube in step 5.

5. Add 700 μl Buffer RW1 to the RNeasy column. Close the lid gently, and centrifuge for 15 s at ≥8000×g to wash the column membrane. Discard the flow-through. Reuse the centrifuge tube in step 6.

6. Add 500 μl Buffer RPE to the RNeasy column. Close the lid gently, and centrifuge for 15 s at ≥8000×g to wash the column membrane. Discard the flow-through. Reuse the centrifuge tube in step 7.

7. Add another 500 μl Buffer RPE to the RNeasy column. Close the lid gently, and centrifuge for 2 min at ≥8000×g to dry the RNeasy spin column membrane.

8. Place the RNeasy spin column in a new 2 ml collection tube and discard the old collection tube with the flow-through. Close the lid gently and centrifuge at full speed for 1 min.

9. To elute, transfer the RNeasy column to a new 1.5 ml collection tube. Add 30 μl of RNase-free water directly onto the RNeasy spin column membrane. Close the tube gently. Let it stand for 1 min, and then centrifuge for 1 min at ≥8000×g.

1.3. 1st Strand cDNA Synthesis

RNA (~3 μg) was reverse-transcribed to produce cDNA using the GE Life Sciences 1st strand cDNA synthesis kit following the manufacturer's protocol (1.3.1). This was repeated twice to generate 3 independent cDNA products (rounds 1, 2 and 3) in order to detect and avoid cDNA mutations induced by the Reverse Transcriptase.

1.3.1 Protocol for 1st-Strand cDNA Synthesis (GE Life Sciences)

1. Place the RNA sample in a microcentrifuge tube and add RNase-free water to bring the RNA to the appropriate volume (20 μL-12× dilution, see Table A).

2. Heat the RNA solution to 65° C. for 10 minutes, then chill on ice. Gently pipette the Bulk First-Strand cDNA Reaction Mix to obtain a uniform suspension. (Upon storage, the BSA may precipitate in the Mix; this precipitate will dissolve during incubation).

3. Add Bulk First-Strand cDNA Reaction Mix (11 μL) to a sterile 1.5 or 0.5 ml microcentrifuge tube. To this tube add 1 μL of DTT Solution, 1 μL (0.2 μg, 1:25 dilution) of NotI-d(T)18 primer and the heat-denatured RNA. Pipette up and down several times to mix.

4. Incubate at 37° C. for 1 hour and heat inactivate transcriptase for 5 min at 94° C.

TABLE A

| Volumes of Components in First-Strand Reaction | | | | |
|---|---|---|---|---|
| Bulk 1st Strand Reaction Mix | Primer | DTT | RNA | Final Volume First-Strand Reaction |
| 11 μL | 1 μL | 1 μL | 20 μL | 33 μL |

cDNA Purification: A simple protocol designed to remove contaminating First-Strand cDNA primer that could interfere with subsequent PCR reactions.

1. Add 99 μl of Buffer QG (from Qiagen Gel Extraction Kit, Cat. No: 28704) and 33 μl IPA. Mix and add to a QiaQuick Gel Extraction Column. Spin and discard the flow-through.

2. Wash the column once with 500 μl Buffer QG. Discard the flow-through.

3. Wash the column once with 750 μl Buffer PE. Discard the flow-through.

4. Spin the column to remove any residual alcohol and allow the column to dry.

5. Elute the cDNA with 50 μl distilled water pre-heated to 65° C.

1.4. cDNA Sequence Determination

The cDNA was amplified by PCR in 3 separate reactions as described in 1.4.1. Immunoglobulin cDNA was PCR-amplified with kappa light chain primers plus MKC (FIG. 1) or heavy chain primers plus MHCmix (FIG. 2) using the Phusion High-Fidelity PCR Master Mix.

The result of each PCR reaction was a single amplification product that was purified using the QIAquick PCR purification kit (1.4.2) and sequenced (by GATC Biotech) in both directions using the M13-Forward and M13-Reverse primers (FIG. 3) to obtain three independent sets of sequence information for each immunoglobulin chain.

1.4.1 PCR-Cloning of Mouse Variable Regions

Sterile water: Treat de-ionised, distilled water with DEPC (Sigma, D-5758) (final conc 0.1%) overnight at RT. Autoclave for 20 minutes at 115° C. and 15 p.s.i.

PCR-cloning primers (see FIGS. 1 and 2): Prepare separate 10 μM stock solutions of MHV 1-12, MKV 1-11, MHC and MKC primers in sterile water.

5×TBE buffer: (0.45M Tris-borate, pH8.3 10 mM EDTA.)

10×TAE buffer: (0.4M Tris-acetate, pH8.0, 10 mM EDTA.)

1. Label 11 GeneAmp™ PCR reaction tubes MKV1-11 and 12 labelled MHV1-12. For each reaction add as follows:

| Kappa chain | Heavy chain |
|---|---|
| 9 μl sterile water | 9 μl sterile water |
| 12.5 μl Phusion Master Mix | 12.5 μl Phusion Master Mix |
| 1.25 μl 10 μM MKCv2 primer | 1.25 μl 10 μM of one MHCv2 primer e.g. MHCG1v2 |
| 1 μl 1st strand reaction cDNA template | 1 μl 1st strand reaction cDNA template |

2. To each add 1.25 μl of the appropriate MKV-v2 or MHV-v2 primer. Load the reaction tubes into a DNA thermal cycler and cycle:

| | Phusion | Phusion Flash | |
|---|---|---|---|
| 98° C. | 5 min | 10 sec | |
| 98° C. | 20 sec | 1 sec | ×30 cycles |
| 60° C. | 20 sec | 5 sec | |
| 72° C. | 20 sec | 6-7 sec | |
| 72° C. | 5 min | 1 min | |
| 4° C. | Hold | Hold | |

3. Electrophorese a 5 μl sample from each PCR-reaction on a 2% (w/v) agarose/1× TBE (or 1×TAE) gel, containing 1×SYBR Safe DNA stain, to determine which of the leader primers produces a PCR-product. Positive PCR-clones will be about 420-500 bp in size.

4. For the positive clones, PCR purify the remaining sample using the QIAGEN PCR Purification Kit, eluting into 30-50 μl Buffer EB. This should be sent to an outside contractor (e.g. GATC) for PCR-fragment sequencing using the M13 Forward and M13 Reverse primers.

5. Repeat those PCR-reactions that appear to amplify full-length variable domain gene, using the other two 1st strand reaction preps. It is vital to have three, independent clones of each variable domain gene to eliminate PCR-errors and RT errors.

1.4.2 QIAquick PCR Purification Microcentrifuge and Vacuum Protocol (QIAGEN)

1. All centrifugation steps are at 17,900×g (13,000 rpm) in a conventional table top microcentrifuge.

2. Add 5 volumes of Buffer PBI to 1 volume of the PCR reaction and mix. If the colour of the mixture is orange or violet, add 10 μl of 3 M sodium acetate, pH 5.0, and mix. The colour of the mixture will turn yellow.

3. Place a QIAquick column in ▲ a provided 2 ml collection tube or into ● a vacuum manifold.

4. To bind DNA, apply the sample to the QIAquick column and ▲ centrifuge for 30-60 s or ● apply vacuum to the manifold until all samples have passed through the column. ▲ Discard flow-through and place the QIAquick column back into the same tube.

5. To wash, add 0.75 ml Buffer PE to the QIAquick column and ▲ centrifuge for 30-60 s or ● apply vacuum. ▲ Discard flow-through and place the QIAquick column back in the same tube.

6. Centrifuge the column in a 2 ml collection tube (provided) for 1 min.

7. Place each QIAquick column in a clean 1.5 ml micro-centrifuge tube.

8. To elute DNA, add 40-50 μl Buffer EB (10 mM Tris·Cl, pH 8.5) to the centre of the QIAquick membrane and centrifuge the column for 1 min.

1.5. VK and VH DNA Sequence

The consensus sequence of hybridoma TPAi-1 VK, and the consensus DNA sequence of TPAi-1 VH, are shown in FIG. 4 and FIG. 5.

2.0 Generation of a Chimeric Version of the TPAi-1 Antibody 2.1. VK and VH DNA Sequence Germ Line Analysis of the TPAi-1 sequences show that the Kappa Light Chain is a Murine VK1, with two somatic mutations, both of which are in Framework 1 (FIG. 6). The Heavy Chain is a Murine VH1. This shows a low identity with the germline, having a rather high number of somatic mutations and has an unexpectedly short CDR-1, not represented in the published murine antibody germlines. (FIG. 7).

2.2. Construction of the Chimeric Expression Vectors

Construction of chimeric expression vectors entails cloning the amplified variable regions into IgG/kappa vectors (pHuG1 and pHuK—FIGS. 8 and 9), using ligase-independent cloning (LIC). The vectors (pCMV modified) are digested with BfuA1 (BspM1) and then compatible overhangs are generated with T4 DNA polymerase 3'-5' exonuclease activity (+dATP).

The genes for TPAi-1 VH and VK were codon optimized for human sequences and synthesized by GenScript. The antibody sequences (FIGS. 11 and 12) were amplified by PCR from the GenScript constructs with primers containing the 3' end of the leader sequence (most of the sequence is present in the vector)—forward primer—or the beginning of the constant region (IgG1 or kappa)—reverse primer —, followed by the beginning of the variable region (in each direction) (FIG. 3). The complementary overhangs were generated in the PCR products by T4 DNA polymerase (+dTTP) treatment (2.2.1). Vector and inserts were incubated at RT and used for the transformation of chemically-competent TOP10 bacteria and plated on Kanamycin plates.

Several clones were isolated and colonies screened by PCR using primers HCMVi and HuG1 LIC Rev for VH or HuK LIC Rev for VK (FIG. 3). The clones generating the correct-sized PCR products were selected, miniprep plasmid DNA isolated using the QIAGEN kit (2.2.2) and sequenced using the same primers.

2.2.1 Generation of mAb Expression Vectors by LIC

Insert Preparation

1. Use sequence to generate LIC primers.

2. LIC clone variable domains into LIC expression vectors (vector maps shown in FIGS. 8, 9 and 10) directly from 1st Strand cDNA or synthesized DNA.

3. Set up PCR reactions:

| Reagent | Volume (for 20 μl final reaction volume) |
|---|---|
| $H_2O$ | add to 50 μl |
| 2x Phusion PCR Master Mix | 25 μl |
| Primer Rev | 2.5 μl, Cf = 0.5 μM |
| Primer For | 2.5 μl, Cf = 0.5 μM |
| DNA | 1 μl |

Note:
Polymerase that generates blunt ended PCR products must be used in this step. Other Polymerases which produce T overhangs are not suitable.

4. Cycle:

| | 3-step protocol | | |
|---|---|---|---|
| Cycle step | Time | Temp. | Cycles |
| Initial denaturation | 98° C. | 10 s | 1 |
| Denaturation Temp. | 98° C. | 1 s | 30 |
| Annealing | 55° C. | 5 s | |
| Extension | 72° C. | 15 s/1 kb | |
| Final extension | 72° C. | 1 min | 1 |
| | 4° C. | hold | |

5. Run 5 μL of PCR products on a gel to ensure correct sized product—should be around 350 bp.

6. PCR purify products using Qiagen PCR purification kit to remove nucleotides and primers. Elute into 40 μL 10 mM Tris-HCl, pH8.5 (Buffer EB).

7. T4 DNA Polymerase treat inserts:

| | |
|---|---|
| PCR product | 40 μL |
| 10xNEB 2 | 4.5 μL |
| dTTP (100 mM) NEB | 1.25 μL |
| T4 DNA Polymerase NEB | 1 μL |

8. Incubate at RT for 30 min and then inactivate enzyme at 70° C. for 20 min.

Vector Preparation

9. Digest the LIC vectors with BfuAI by incubating at 50° C. for 3 hours or overnight:

| | |
|---|---|
| 10x NEB buffer 3 | 10 μL |
| 100x BSA | 1 μL |
| BfuA1 | 5 μL |
| LIC vector | 5 μg |
| $dH_20$ | to 100 μL |

10. Following BfuAI digestion add: 2 μL of Bam HI and incubate at 37° C. for 2 hours.

11. T4 DNA polymerase treat the vector as follows:

| | |
|---|---|
| 10x NEB buffer | 2 6 μL |
| 100 mM dATP | 1.5 μL |
| T4 DNA Pol | 1 μL |
| BfuA1 digested vector | 50 μL |

12. Incubate at RT for 30 min and then inactivate the enzyme at 70° C. for 20 min.

Cloning

13. Mix 2 μL of insert with 1 μL vector for 5 min RT. Add 1 μL 25 mM EDTA, mix gently and leave for 5 min at RT. Always perform vector alone transformation.

14. Use the ligation mix to transform 50 μL of chemically competent Invitrogen TOP 10 bacteria following the manufacturer's instructions (2.2.1.1) and spread on 90 mm diameter LB agar plates containing Kanamycin (50 μg/ml). Incubate overnight at 37° C.

Pick Colonies from Transformation

15. PCR confirm using Phusion PCR Master Mix:

| Reagent | Volume (for 20 μl final reaction volume) |
|---|---|
| 2x Phusion PCR Master Mix | 10 μL |
| HCMVi primer | 1 μL |
| HuG1/HuK LIC primer | 1 μL |
| $dH_20$ | to 20 μL |
| DNA | Dip of colony (grow day culture of same colony) |

| | 3-step protocol | | |
|---|---|---|---|
| Cycle step | Time | Temp. | Cycles |
| Initial denaturation | 98° C. | 30 s | 1 |
| Denaturation Temp. | 98° C. | 30 s | 25-30 |
| Annealing | 65° C. | 10 s | |
| Extension | 72° C. | 10 s | |
| Final extension | 72° C. | 5 min | 1 |
| | 4° C. | hold | |

16. Run each PCR-reaction on a 2% agarose e-gel cassette and run for 15 min to determine the size of any PCR-product bands on the gel.

17. Grow Kanamycin starter cultures overnight to mini-prep constructs and sequence the DNA (using the same primers) from at least two separate positive clones of the variable genes to identify any possible errors due to the PCR-reaction itself.

2.2.1.1 Transformation of TOP10™ *E. coli* (Invitrogen Protocol)

1. Centrifuge the vial(s) containing the ligation reaction(s) briefly and place on ice.

2. Thaw, on ice, one 50 μL vial of One Shot cells for each ligation/transformation.

3. Pipet 1 to 5 μL of each ligation reaction directly into the vial of competent cells and mix by tapping gently.

Do not mix by pipetting up and down. The remaining ligation mixture(s) can be stored at −20° C.

4. Incubate the vial(s) on ice for 30 minutes.

5. Incubate for exactly 30 seconds in the 42° C. water bath then place on ice.

6. Add 250 μL of pre-warmed S.O.C medium to each vial.

7. Shake the vial(s) at 37° C. for exactly 1 hour at 225 rpm in a shaking incubator.

8. Spread 200 μL from each transformation vial on separate, labelled LB agar plates containing 500 μg/ml kanamycin.

9. Invert the plate(s) and incubate at 37° C. overnight.

2.2.2 Plasmid DNA Miniprep Isolation Using QIAprep® (Qiagen Protocol)

1. Resuspend pelleted bacterial cells in 250 μL Buffer P1 and transfer to a microcentrifuge tube. Ensure that RNase A has been added to Buffer P1.

2. Add 250 μL Buffer P2 and invert the tube gently 4-6 times to mix.

3. Add 350 μL Buffer N3 and invert the tube immediately but gently 4-6 times. The solution should become cloudy.

4. Centrifuge for 10 min at 13,000 rpm (17,900×g) in a table-top microcentrifuge. A compact white pellet will form.

5. Apply the supernatant from step 4 to the QIAprep Spin Column by pipetting.

6. Centrifuge for 30-60 s. Discard the flow-through.

7. Wash column by adding 0.5 mL of Buffer PB and centrifuging for 30-60 s.

8. Wash column by adding 0.75 mL Buffer PE and centrifuging for 30-60 s.

9. Discard the flow-through and centrifuge for an additional 1 min.

10. Place the QIAprep column in a clean 1.5 ml microcentrifuge tube. To elute DNA, add 50 μL Buffer EB (10 mM TrisHCl, pH 8.5) to the center of the QIAprep Spin Column, let stand for 1 min, and centrifuge for 1 min.

2.3. Generation of the Chimeric Antibodies

ExpiCHO suspension cells growing in ExpiCHO expression medium and antibiotics were co-transfected with TPAi-1 VH.pHuG1 and TPAi-1 VK.pHuK (1 μg DNA each) using ExpiFectamine-CHO Reagent (2.3.1). The cells were grown in 1 ml growth medium for 7 days. Up to 220 μg/ml of chimeric TPAi-1 antibody was measured in the conditioned medium by Octet with Protein G biosensors (2.3.2).

2.3.1 ExpiCHO Transfection in 24-Well Plates 1 ml Transfection

Materials

ExpiFectamine CHO kit 1 L (ThermoFisher Scientific cat. no. A29129)
- ExpiFectamine CHO Reagent
- ExpiCHO Enhancer
- ExpiCHO Feed OptiPRO SFM (ThermoFisher Scientific cat. no. 12309-050)

ExpiCHO Expression Medium (cat. no. A29100-01)

Protocol:

1. Subculture and expand ExpiCHO cells until the cells reach a density of approximately 4-6×106 viable cells/mL.

Day −1: Split Cells

2. On the day prior to transfection (Day −1), split the expiCHO culture to a final density of 3-4×106 viable cells/mL and allow the cells to grow overnight.

Day 0: Transfection

3. Dilute cells to 6×106 viable cells/mL.

4. Aliquot 0.9 mL of cells into each well of the 24-well plate to be used for transfection.

5. Prepare ExpiFectamine/DNA complexes:

a. Dilute plasmid DNA by adding 1 μL DNA to a final volume of 50 μL OptiPro for each well to be transfected (1 ug of plasmid DNA per mL of culture volume to be transfected).

b. Dilute 4 μL ExpiFectamine CHO reagent in 46 μL OptiPro medium for each well to be transfected (no incubation time required).

c. Add the diluted ExpiFectamine CHO to the diluted DNA and mix by gentle pipetting 3-4 times (incubation 1 to 5 min).

6. Add 100 μL of the complexation mixture to each well containing culture in the 24-well plate.

7. Cover the plates with a gas-permeable lid.

8. Incubate the 24-well plate in a 37° C. incubator with 8% CO2 on an orbital shaker (recommended shake speed 225 rpm for shakers with a 19 mm orbital throw).

Day 1: Add 6 ul ExpiCHO Enhancer and 190 ul ExpiCHO Feed 18-22 hours post-transfection.

Harvest: For Standard Protocol: Protein expression is typically complete and supernatant ready to be harvested by Day 7-8 post transfection.

2.3.2 Quantification of Human Antibodies by Octet Using Protein G Biosensors

Materials 384-well tilted-bottom plate (18-5080-Pack, ForteBio)

96-well, PP, F-bottom, black plate (655209, Greiner)

Protein G sensors (Pack), 18-5083

Appropriate diluent, ideally, same as buffer or supernatants that your samples are in (Expi293 or ExpiCHO media when neat supernatant tested)

Human IgG Standards:

MRCT Human IgG1 Isotype Control

1. Turn on Octet instrument (at least 40 mins prior to starting assay)

2. Prepare 100 μl (sufficient for 2×40 μl) samples:

a. Isotype standards at or 500, 250, 125, 62.5, 31.25, 15.6, 7.81, 0 μg/ml using a diluent which matches your sample (e.g. clean media or PBS if your samples are purified)

b. Test (unknown) samples

3. Open software and select murine IgG quantitation (8CH_96 W). Modify protocol so plate 1, is a 384-well plate. Set-up plate layout, including additional wells for replicates, diluent (reference) and controls (e.g. conditioned/expression control)

4. Pre-soak (≥10 mins) biosensors in 200 μl diluent buffer

5. Aliquot 40 μl per sample into a 384-well tilted-bottom (product code: 18-5080) plate in replicates. Seal plate and spin (1000 rpm for 2 mins) in bench-top centrifuge 6. Remove plate seal and insert plate. Check/set software run parameters:

a. Save file destination b. Set temperature to 25° C. (if room is air-conditioned otherwise use 30° C.)

c. 10 minute (600 s) wait before start and shake

7. Begin experiment.

8. To process data, open evaluation software. Select wells to use in standard calculation and fit to a dose response-5PL fit.

Biosensors Storage

At the end of the run, biosensors will be back in original positions.

To store sensors for re-use:

remove sensors carefully from the tray soak in 15% Sucrose for ~10 min (you may use the same 96-well black plate but different column).

Allow to air dry and keep the in storage tray.

2.4 tPA Binding Activity of Chimeric Antibodies

Binding of the chimeric TPAi-1 antibody to recombinant human tPA (rh-tPA: abcam ab92637), recombinant mouse tPA (rm-tPA: abcam ab92715) and recombinant rat tPA (rr-tPA: abcam ab92596) was measured by ELISA and compared to the original mouse antibody 2.4.1). The chimeric and mouse TPAi-1 antibodies bound rh-tPA with comparable EC50 values (FIG. 12). Neither TPAi-1 antibodies bound to rm-tPA or rr-tPA.

2.4.1 tPA Binding ELISA

1. Coat each well of a 94-well MaxiSorp plate (Nunc) with 100 μL aliquots of 0.2 μg/mL of human tPA (AbCam ab92637), murine tPA (AbCam ab92715) or rat tPA (AbCam ab92596) in PBS and incubate overnight at 4° C.

2. Wash 3× with PBS-T (0.1% Tween20).

3. Block the experimental plate and a fresh plate (dilution plate) with 250 μL of PBS/0.2% BSA/0.05% Tween20 per well and incubate for 1 hour at RT. Wash 3× with PBS-T (0.1% Tween20).

4. Using the dilution plate, add 200 uL of antibody (diluted in PBS/0.2% BSA/0.05% Tween20 if necessary) to wells in column 1; 120 μL of buffer (PBS/0.2% BSA/0.05% Tween20) in the other wells.

5. Transfer 56 μL from column 1 to the neighbouring wells in column 2. Continue to column 12 with a series of half-log ($10^{0.5}$, 3.162×) dilutions of the experimental samples. Transfer 100 μL per well from the dilution plate to the experimental plate.

6. Incubate for 1 hour at RT. Wash wells 3× with PBS-T.

| | | | |
|---|---|---|---|
| 7. Dilute the appropriate conjugate in PBS/0.2% BSA/0.05% Tween20:goat anti-human IgG (Fc specific) peroxidase | Sigma A0170 | 6000-fold dilution | for detecting whole human IgG |
| goat anti-mouse IgG (Fc specific) peroxidase | Sigma A2554 | 10 000-fold dilution | for detecting mouse IgG |
| goat anti-human kappa-peroxidase | Sigma A7164 | 5000-fold dilution | for detecting in assays including human Fab |

Add 100 μL to each well. Incubate 1 hour at RT and repeat washing step.

8. Add 150 μL of substrate (Enhanced K-Blue) per well and incubate for 10 minutes at RT.

9. Stop the reaction by adding 50 μl of RED STOP solution to each well.

10. Read the optical density at 650 nm.

3.0. Design of TPAi-1 Humanised Antibody Variants 3.1. Human VH and VK cDNA Databases The protein sequences of human and mouse immunoglobulins from the International Immunogenetics Database 2009 (Lefranc, 2015) and the Kabat Database Release 5 of Sequences of Proteins of Immunological Interest (last update 17 Nov. 1999)(Kabat et al. 1991) were used to compile a database of human immunoglobulin sequences in Kabat alignment.

3.2. Molecular Model of TPAi-1

A homology model of mouse TPAi-1 antibody variable regions was calculated using the Discovery Studio 4.1 program run in automatic mode. Sequence templates for the Light Chain and Heavy Chain variable regions were determined by Blast analysis of the Accelrys antibody pdb structures database. These templates were used to potential models.

3.3. Human Framework Selection

Humanisation requires the identification of suitable human V regions. The sequence analysis program, Gibbs, was used to interrogate the human VH and VK databases with TPAi-1 VH and VK protein sequences using various selection criteria. Using the program Discovery Studio (Accelrys), FW residues within 4 Å of the CDR residues (KABAT and IMGT definitions) in the structures of mouse TPAi-1 antibody were identified.

Human heavy chain donor candidates and human kappa light chain donor candidates were identified using various selection criteria.

3.4. Design of TPAi-1 Human Heavy Chain

The initial design of the humanised version of TPAi-1 was the grafting of CDR 1, 2 and 3 from TPAi-1 VH into the acceptor FW of a potential heavy chain donor candidate Potential sequences were assembled in silico.

3.5. Design of TPAi-1 Human Kappa Light Chain

CDR 1, 2 and 3 from TPAi-1 VK were grafted into the acceptor FW of potential human kappa light chain donor candidates to generate the potential version of humanised TPAi-1.

3.6. Remodelling of TPAi-1

The humanised TPAi-1 candidates were remodeled, including mutations, using various selection criteria.

4.0. Generation and Properties of a Humanised Version of TPAi-1

4.1. Generation of TPAi-1 Humanised Antibodies

The genes for humanised TPAi-1 candidates were synthesized by GenScript and codon optimized for human sequences. Using software algorithms proprietary to GenScript, the sequences were optimized by silent mutagenesis to use codons preferentially utilized by human cells and synthesized. Heavy chain and kappa light chain constructs were PCR amplified with specific primers to the expression vector+insert (as described previously for the chimeric versions) and inserted into pHuG1 and pHuK (FIGS. 8 and 9) in ligase independent cloning reactions (2.2.1) and used to transform TOP10 bacteria (2.2.1.1). Subsequent humanised variants were obtained by PCR mutagenesis (4.1.1) using the primers in FIG. 14. Clones were sequenced and expression plasmid DNA was prepared using the QIAGEN Plasmid Miniprep Kit or Qiagen Plasmid Maxiprep kit (4.1.2 and 4.1.3). Expression plasmid preparations encoding (humanised or chimeric) VH and VK were used to transfect ExpiCHO cells 2.3.1), cultured for 5-7 days in serum free media, whereupon the conditioned medium containing secreted antibody was harvested.

4.1.1 QuikChange Lightning Site-Directed Mutagenesis Kit (Stratagene)

1. Prepare the reaction(s) as indicated below:

5 μL of 10× reaction buffer 0.12 μL (25 ng) of heavy chain or kappa light chain template 1.3 μL (125 ng) of oligonucleotide mutation primer For 1.3 μL (125 ng) of oligonucleotide mutation primer Rev 1 μL of dNTP mix 1.5 μL of QuikSolution reagent ddH2O to a final volume of 50 μL 1 μL of QuikChange Lightning Enzyme 2. Cycle each reaction using the cycling parameters outlined in the following table:

| | 3-step protocol | | |
|---|---|---|---|
| Cycle step | Time | Temp. | Cycles |
| Initial denaturation | 98° C. | 2 min | 1 |
| Denaturation Temp. | 95° C. | 20 s | 18 |
| Annealing | 65° C. | 10 s | |
| Extension | 68° C. | 3 min | |
| Final extension | 68° C. | 5 min | 1 |
| | 4° C. | hold | |

3. Add 2 μL of the Dpn I restriction enzyme

4. Gently and thoroughly mix each reaction, microcentrifuge briefly, then immediately incubate at 37° C. for 5 minutes to digest the parental dsDNA 5. Transform 2 μL of the Dpn I-treated DNA from each reaction into separate 45-μL (+2 μL β-ME) aliquots of XL10-Gold ultracompetent cells (see Transformation of TOP10™ *E. coli*).

6. Screen colonies using the Phusion method, prepare miniprep DNA and sequence to check for the correct mutation.

4.1.2 Plasmid DNA Miniprep Isolation Using QIAprep® (Qiagen Protocol)

1. Resuspend pelleted bacterial cells in 250 μL Buffer P1 and transfer to a microcentrifuge tube. Ensure that RNase A has been added to Buffer P1.

2. Add 250 μL Buffer P2 and invert the tube gently 4-6 times to mix.

3. Add 350 μL Buffer N3 and invert the tube immediately but gently 4-6 times. The solution should become cloudy.

4. Centrifuge for 10 min at 13,000 rpm (~17,900×g) in a table-top microcentrifuge. A compact white pellet will form.

5. Apply the supernatant from step 4 to the QIAprep Spin Column by pipetting.

6. Centrifuge for 30-60 s. Discard the flow-through.

7. Wash column by adding 0.5 mL of Buffer PB and centrifuging for 30-60 s.

8. Wash column by adding 0.75 mL Buffer PE and centrifuging for 30-60 s.

9. Discard the flow-through and centrifuge for an additional 1 min.

10. Place the QIAprep column in a clean 1.5 ml microcentrifuge tube. To elute DNA, add 50 μL Buffer EB (10 mM TrisHCl, pH 8.5) to the center of the QIAprep Spin Column, let stand for 1 min, and centrifuge for 1 min.

4.1.3 Qiagen Protocol for Plasmid DNA Maxi Prep

1. Pick a single colony from a freshly streaked selective plate and inoculate a starter culture of 2-5 ml LB medium containing the appropriate selective antibiotic. Incubate for ~8 h at 37° C. with vigorous shaking (~300 rpm). Use a tube or flask with a volume of at least 4 times the volume of the culture.

2. Dilute the starter culture 1/500 to 1/1000 into selective LB medium. For high-copy plasmids inoculate 25 ml or 100 ml medium. For low-copy plasmids, inoculate 100 ml or 500 ml medium. Grow at 37° C. for 12-16 h with vigorous shaking. Use a flask or vessel with a volume of at least 4 times the volume of the culture. The culture should reach a cell density of approximately 3-4×109 cells per ml, which typically corresponds to a pellet wet weight of approximately 3 g/L medium.

3. Harvest the bacterial cells by centrifugation at 6000×g for 15 min at 4° C. 6000×g corresponds to 6000 rpm in Sorvall® GSA or GS3 or Beckman™ JA-10 rotors. Remove all traces of supernatant by inverting the open centrifuge tube until all medium has been drained.

4. Resuspend the bacterial pellet in 4 ml or 10 ml Buffer P1. For efficient lysis it is important to use a vessel that is large enough to allow complete mixing of the lysis buffers. Ensure that RNase A has been added to Buffer P1. The bacteria should be resuspended completely by vortexing or pipetting up and down until no cell clumps remain.

5. Add 4 ml or 10 ml Buffer P2, mix gently but thoroughly by inverting 4-6 times, and incubate at room temperature for 5 min. Do not vortex, as this will result in shearing of genomic DNA. The lysate should appear viscous. Do not allow the lysis reaction to proceed for more than 5 min.

6. Add 4 ml or 10 ml of chilled Buffer P3, mix immediately but gently by inverting 4-6 times, and incubate on ice for 15 min or 20 min. Precipitation is enhanced by using chilled Buffer P3 and incubating on ice. After addition of Buffer P3, a fluffy white material forms and the lysate becomes less viscous. The precipitated material contains genomic DNA, proteins, cell debris, and SDS. The lysate should be mixed thoroughly to ensure even potassium dodecyl sulfate precipitation. If the mixture still appears viscous and brownish, more mixing is required to completely neutralize the solution.

7. Centrifuge at 20,000×g for 30 min at 4° C. Remove supernatant containing plasmid DNA promptly. Before loading the centrifuge, the sample should be mixed again. Centrifugation should be performed in non-glass tubes (e.g., polypropylene). A centrifugal force of 20,000×g corresponds to 12,000 rpm in a Beckman JA-17 rotor or 13,000 rpm in a Sorvall SS-34 rotor. After centrifugation the supernatant should be clear 8. Centrifuge the supernatant again at 20,000×g for 15 min at 4° C. Remove supernatant containing plasmid DNA promptly. This second centrifugation step should be carried out to avoid applying suspended or particulate material to the QIAGEN-tip. Suspended material (causing the sample to appear turbid) can clog the QIAGEN-tip and reduce or eliminate gravity flow.

9. Equilibrate a QIAGEN-tip 100 or QIAGEN-tip 500 by applying 4 ml or 10 ml Buffer QBT, and allow the column to empty by gravity flow. Flow of buffer will begin automatically by reduction in surface tension due to the presence of detergent in the equilibration buffer. Allow the QIAGEN-tip to drain completely. QIAGEN-tips can be left unattended, since the flow of buffer will stop when the meniscus reaches the upper frit in the column.

10. Apply the supernatant from step 8 to the QIAGEN-tip and allow it to enter the resin by gravity flow. The supernatant should be loaded onto the QIAGEN-tip promptly. If it is left too long and becomes cloudy due to further precipitation of protein, it must be centrifuged again or filtered before loading to prevent clogging of the QIAGEN-tip.

11. Wash the QIAGEN-tip with 2×10 ml or 2×30 ml Buffer QC. Allow Buffer QC to move through the QIAGEN-tip by gravity flow. The first wash is sufficient to remove all contaminants in the majority of plasmid DNA preparations. The second wash is especially necessary when large culture volumes or bacterial strains producing large amounts of carbohydrates are used.

12. Elute DNA with 5 ml or 15 ml Buffer QF. Collect the eluate in a 10 ml or 30 ml tube. Use of polycarbonate centrifuge tubes is not recommended as polycarbonate is not resistant to the alcohol used in subsequent steps.

13. Precipitate DNA by adding 3.5 ml or 10.5 ml (0.7 volumes) room-temperature isopropanol to the eluted DNA. Mix and centrifuge immediately at 15,000×g for 30 min at 4° C. Carefully decant the supernatant. All solutions should be at room temperature in order to minimize salt precipitation, although centrifugation is carried out at 4° C. to prevent overheating of the sample. A centrifugal force of 15,000×g corresponds to 9500 rpm in a Beckman JS-13 rotor and 11,000 rpm in a Sorvall SS-34 rotor. Alternatively, disposable conical bottom centrifuge tubes can be used for centrifugation at 5000×g for 60 min at 4° C. Isopropanol pellets have a glassy appearance and may be more difficult to see than the fluffy, salt-containing pellets that result from ethanol precipitation. Marking the outside of the tube before centrifugation allows the pellet to be more easily located. Isopropanol pellets are also more loosely attached to the side of the tube, and care should be taken when removing the supernatant.

14. Wash DNA pellet with 2 ml or 5 ml of room-temperature 70% ethanol, and centrifuge at 15,000×g for 10 min. Carefully decant the supernatant without disturbing the pellet.

15. Air-dry the pellet for 5-10 min, and redissolve the DNA in a suitable volume of buffer (e.g., TE buffer, pH 8.0, or 10 mM Tris·Cl, pH 8.5). Redissolve the DNA pellet by rinsing the walls to recover all the DNA, especially if glass tubes have been used. Pipetting the DNA up and down to promote resuspension may cause shearing and should be avoided. Overdrying the pellet will make the DNA difficult to redissolve. DNA dissolves best under slightly alkaline conditions; it does not easily dissolve in acidic buffers.

4.2. Antibody Expression

The concentrations of IgG1κ antibodies in ExpiCHO cell conditioned media were measured by Octet using Protein G biosensors (2.3.2).

Examples of humanised TPAi-1 antibodies are shown in Table 1.

TABLE 1

Humanised TPAi-1 antibodies

| mAb Identifier | Sequence of variable heavy chain | Sequence of variable light chain |
|---|---|---|
| TPAi-1 RHE/RKA | SEQ ID No. 14 | SEQ ID No. 29 |
| TPAi-1 RHP/RKA | SEQ ID No. 15 | SEQ ID No. 29 |
| TPAi-1 RHB/RKA | SEQ ID No. 16 | SEQ ID No. 29 |
| TPAi-1 RHJ/RKA | SEQ ID No. 17 | SEQ ID No. 29 |
| TPAi-1 RHK/RKA | SEQ ID No. 18 | SEQ ID No. 29 |
| TPAi-1 RHL/RKA | SEQ ID No. 19 | SEQ ID No. 29 |
| TPAi-1 RHM/RKA | SEQ ID No. 20 | SEQ ID No. 29 |
| TPAi-1 RHN/RKA | SEQ ID No. 21 | SEQ ID No. 29 |
| TPAi-1 RHO/RKA | SEQ ID No. 22 | SEQ ID No. 29 |
| TPAi-1 RHQ/RKA | SEQ ID No. 23 | SEQ ID No. 29 |

TABLE 1-continued

| Humanised TPAi-1 antibodies | | |
|---|---|---|
| mAb Identifier | Sequence of variable heavy chain | Sequence of variable light chain |
| TPAi-1 RHR/RKA | SEQ ID No. 24 | SEQ ID No. 29 |
| TPAi-1 RHS/RKA | SEQ ID No. 25 | SEQ ID No. 29 |
| TPAi-1 RHT/RKA | SEQ ID No. 26 | SEQ ID No. 29 |
| TPAi-1 RHU/RKA | SEQ ID No. 27 | SEQ ID No. 29 |
| TPAi-1 RHV/RKA | SEQ ID No. 28 | SEQ ID No. 29 |

4.3. Antigen Binding by the Humanised TPAi-1 Antibodies

Binding activity to the tPA antigen was measured by Binding ELISA (2.4.1). The data shown in FIGS. 15 and 15A show the binding potency of humanised versions of TPAi-1 in Table 1.

4.4. Determination of Humanised Candidate Antibodies Tm (Melting Temperature)

In order to determine the melting temperature antibodies TPAi-1 RHE/RKA and TPAi-1 RHP/RKA, these antibodies were tested in a thermal shift assay. Samples were incubated with a fluorescent dye (Sypro Orange) for 71 cycles with 1° C. increase per cycle in a qPCR thermal cycler. Tm values for the two humanised antibodies are indicated in FIG. 16. Both antibodies have a Tm of at least 70° C., indicating that they pass thermal stability requirements.

4.5. Aggregation Analysis of Humanised Candidate Antibodies

Aggregation assessment of the TPAi-1 RHE/RKA and TPAi-1 RHP/RKA antibodies was carried out by dynamic light scattering (DLS). The antibodies were found to have hydrodynamic radii and polydispersity consistent with monomer (FIG. 17). The data suggest there are no aggregation concerns in the antibody samples analysed.

4.6. Non-Specific Protein-Protein Interactions (CIC)

Cross-Interaction Chromatography using bulk purified human polyclonal IgG is a technique for monitoring non-specific protein-protein interactions, and can be used to discriminate between soluble and insoluble antibodies.

An elevated Retention Index (k') indicates a self-interaction propensity and a low solubility. Both candidate antibodies show a Retention Index below 0.05, indicating a low propensity for non-specific interactions and good solubility (FIG. 18).

4.7. Solubility of Humanised Candidate Antibodies

The purified candidate antibodies were concentrated using solvent absorption concentrators (MWCO 7500 kDa) and the concentration measured at timed intervals. Both samples were concentrated to more than 40 mg/ml without apparent precipitation (FIG. 19).

4.8. Freeze/Thaw Stress Analysis of Candidate Antibodies

Samples of the purified RHE/RKA and RHP/RKA antibodies were subjected to 10 cycles of 15 minutes at −80° C. followed by thawing for 15 minutes at Room Temperature. Control samples were kept at 4° C. throughout. The samples were then analysed by SEC-MALS for aggregation (FIG. 20). The data suggest that freeze/thaw causes no aggregation in the antibodies tested.

4.9. Heat-Induced Stress Analysis of Candidate Antibodies

Samples of the purified RHE/RKA and RHP/RKA antibodies were heat exposed at a) Room Temperature, b) 37° C. and C) 50° C. or kept at 4° C. for 30 days. Samples were then analysed by SEC-MALS for aggregation (FIG. 21). None of the incubations resulted in any aggregation. Overall the data suggest there are no aggregation concerns in any of the humanised TPAi-1 antibody samples analysed.

4.10 Serum Stability Assessment of Candidate Antibodies

Purified samples of humanised antibodies TPAi-1 RHE/RKA and RHP/RKA were incubated in mouse, human and cynomolgus serum (4.10.1). The binding abilities of the antibodies after 29 days incubation were measured by binding ELISA to human tPA. For each antibody, one ELISA plate compared the binding of the 4° C. control sample to samples incubated at 37° C. in PBS and human serum. A second ELISA plate compared the binding of the 4° C. control sample to samples incubated at 37° C. in mouse and cynomolgus serum. The graphs of FIG. 22, as well as the EC50 values obtained from the curves, show that, for both RHE/RKA and RHP/RKA, the binding abilities of the samples of antibodies incubated in the various sera were comparable with those of the 4° C. control sample and the sample incubated at 37° C. in PBS. Therefore the TPAi-1 RHE/RKA and RHP/RKA antibodies retained their binding capabilities on incubation in mouse, human and cynomolgus serum for 29 days.

4.10.1 Antibody Serum Stability Assessment

Samples: 600 μl at 0.4 mg/mL of polished antibody in PBS (240 μg)

Test conditions: Mouse serum (SCD-808), Human serum (S-123) and Cyno serum (S-118) from Seralab 1. Aliquot 150 μl serum and PBS control in a round bottom 96-well plate and add 50 μl 0.4 mg/mL antibody solution in PBS (final concentration of 100 μg/mL) in triplicate to each serum type in a tissue culture cabinet (BSL-2). Keep some at 4° C. to use later as a control.

Serum Incubation Plate Layout

| | | | |
|---|---|---|---|
| PBS | Mouse serum | Human serum | Cyno serum |
| PBS | Mouse serum | Human serum | Cyno serum |
| PBS | Mouse serum | Human serum | Cyno serum |

2. Seal the plate with an ELISA plate seal and incubate at 37° C.

3. Take 30 μl samples at day 6, 13, 20 and 29 under sterile conditions (BSL-2) to avoid contamination. Freeze at −20° C. until analysis.

4. Analyse the longer incubation first (if no loss of binding is seen, there is no need to test the other time points).

5. Dilute samples appropriately and assay for antigen binding by generating ELISA binding curves for each sample (5-fold dilution series) (section 8.13) using non-incubated antibody as control.

5.0 Generation and Properties of a Humanised TPAi-1 Fab 5.1. Generation of TPAi-1 RHP/RKA Fab The DNA for the heavy chain variable region of TPAi-1 RHP/RKA was amplified from the IgG1 expression construct TPAi-1_RHP.pHuG1 using primers containing the 3' end of the leader sequence (most of the sequence is present in the vector)—forward primer—or the beginning of the constant region (IgG1)—reverse primer—, followed by the beginning of the variable region (in each direction), FIG. 3. The complementary overhangs were generated in the PCR products by T4 DNA polymerase+dTTP treatment (2.2.1). pHuG1_Fab LIC vector and insert were incubated at RT and used in the transformation of chemically-competent TOP10 bacteria and plated on Kanamycin plates. Several clones were isolated and colonies screened by PCR using primers HCMVi and E1_alpha_rev (FIG. 3). The clones generating the correct sized PCR products were selected, miniprep plasmid DNA isolated using the QIAGEN kit and sequenced using the same primers and HuG1 LIC Rev. TPAi-1_RHP.pHuG1_Fab and TPAi-1_RKA.pHuK expression plasmid preparations were used to transfect Expi293 cells (2.3.1). These were cultured for 5-7 days in serum free media, whereupon the conditioned medium containing secreted antibody was harvested.

5.2. TPAi-1 RHP/RKA Fab Expression

The concentration of TPAi-1 RHP/RKA Fab in the Expi293 cell conditioned medium was measured at 102 μg/ml by Octet, using Streptavadin biosensors coated with an anti-human kappa chain reagent (5.2.1). Larger-scale transfection and culture yielded 72 mg purified Fab from 1 L conditioned medium.

4.10.1 Quantification of Human Fab by Octet Using Anti-Kappa Light Chain-Coated Sensors Streptavadin (SA) biosensors (18-5020) were coated with CaptureSelect™ Biotin Anti-LC-Kappa (Hu) Conjugate (13 kDa Llama antibody fragment; 7103272100, ThermoScientific) by carrying out a 15 min loading step with the reagent diluted to 5 μg/mL in HBS-P+ buffer. The coated biosensors were subjected to 3 regeneration cycles of 10 mM glycine pH2.0 (15 s)/HBS-P+ buffer (15 s), soaked in 15% sucrose solution for 10 min and allowed to airdry.

These sensors were used to quantify the concentration of Fab in supernatant samples by following the procedure of section 2.3.2 but using the template file 'FAb Quantification (Capture Select Anti-Kappa LC)'. Purified control human Fab was used as the standard.

5.3. Antigen Binding by TPAi-1 RHP/RKA Fab

Binding activity of the TPAi-1 RHP/RKA Fab to the human tPA antigen was compared to that of the purified TPAi-1 RHP/RKA antibody in a binding ELISA. The initial experiment used RHP/RKA Fab in the form of Expi293 cell conditioned medium and showed dose-dependent binding of the Fab to human tPA (FIG. 23). The EC50 of the interaction (1.149 nM) is greater than the EC50 of the whole RHP/RKA antibody, as would be expected when comparing a monovalent Fab to a bivalent antibody. Following purification of TPAi-1 RHP/RKA Fab from a large scale culture, its binding to human tPA was reconfirmed by ELISA (FIG. 23). In this assay, plateauing of both binding curves was more apparent. The IgG binding curve plateaued at an A650 level approximately 1.4-fold higher than the plateau of the Fab curve, indicating that some but not all of the IgG was binding bivalently.

5.4. Determination of TPAi-1 RHP/RKA Fab Tm (Melting Temperature)

A thermal shift assay was used to determine the melting temperature of the TPAi-1 RHP/RKA Fab (24). The Tm for TPAi-1 RHP/RKA Fab is 74° C. and the Fab therefore passes thermal stability requirements.

5.5. Aggregation Analysis of TPAi-1 RHP/RKA Fab

TPAi-1 RHP/RKA Fab was injected at 0.4 mL/min into a size exclusion column in an HPLC system and analysed by multi-angle light scattering to determine the absolute molar mass and check for aggregation (see FIG. 25). The Fab showed no signs of aggregation with an average molecular weight of 49.5 kDa, which is the expected range for a Fab monomer in this analysis setup. All samples are monodispersed (Mw/Mn<1.05). The mass recovery is 100% (calculated mass over injected mass), which indicates good protein recovery and that the sample does not seem to stick to the column or contain insoluble aggregates, which would be retained by the guard column. Overall, the data suggest there are no aggregation concerns in the RHP/RKA Fab sample.

5.6. Non-Specific Protein-Protein Interactions of TPAi-1 RHP/RKA Fab (GIG)

Cross-Interaction Chromatography using bulk purified human polyclonal IgG is a technique for monitoring non-specific protein-protein interactions, and can be used to discriminate between soluble and insoluble antibodies. An elevated Retention Index (k') indicates a self-interaction propensity and a low solubility. TPAi-1 RHP/RKA Fab shows a Retention Index below 0.05, indicating a low propensity for non-specific interactions and good solubility (FIG. 26).

5.7. Solubility of TPAi-1 RHP/RKA Fab

The purified TPAi-1 RHP/RKA Fab was concentrated using a solvent absorption concentrator (MWCO 7500 kDa) and the concentration measured at timed intervals. The sample was concentrated to more than 65 mg/ml without apparent precipitation (FIG. 27).

5.8 Freeze/Thaw Stress Analysis of TPAi-1 RHP/RKA Fab

A sample of the purified RHP/RKA Fab was subjected to 10 cycles of 15 minutes at −80° C. followed by thawing for 15 minutes at Room Temperature. A control sample was kept at 4° C. throughout. The samples were then analysed by SEC-MALS for aggregation (FIG. 28). The data suggest that freeze/thaw causes no aggregation in the Fab.

5.9 Heat-Induced Stress Analysis of TPAi-1 RHP/RKA Fab

Samples of the purified RHP/RKA Fab were heat exposed at a) Room Temperature, b) 37° C. and C) 50° C. or kept at 4° C. for 30 days. Samples were then analysed by SEC-MALS for aggregation (FIG. 29). The room temperature and 37° C. incubations did not result in any aggregation but there was 8.2% aggregation in the 50° C. sample. According to the QC criteria, the 50° C. sample should ideally contain less than 5% aggregates and strictly contain less than 10% aggregates, compared to unstressed sample. The TPAi-1 RHP/RKA Fab does contain less than 10% aggregates after heat-induced stress but is less stable than the whole RHP/RKA IgG (see Section 4.9).

5.10 Serum Stability Assessment of TPAi-1 RHP/RKA Fab

Purified samples of TPAi-1 RHP/RKA Fab were incubated in mouse, human and cynomolgus serum (4.10.1). The binding abilities of the antibodies after 29 days incubation were measured by binding ELISA to human tPA (FIG. 30). The straight line sections of the binding curves of FIG. 30 show that the binding abilities of the samples of RHP/RKA Fab incubated in the various sera were comparable with those of the 4° C. control sample and the sample incubated at 37° C. in PBS. The presence of significant amounts of serum in the ELISA wells at the higher Fab concentrations, amounting to 11% serum at 300 nM Fab, appears to reduce binding of the Fab samples. This reduction in binding signal for the top part of the curves results in lower than expected EC50 values for the samples of Fab incubated with sera. However, this does not affect the conclusion that the TPAi-1 RHP/RKA Fab retains its binding capabilities on incubation in mouse, human and cynomolgus serum for 29 days.

6.0. Preparation and Properties of a Humanised TPAi-1 F(ab')2

Conversion of TPAi-1 RHP/RKA from a whole IgG to Fab format resulted in a loss of binding avidity for human tPA in the binding ELISA (Section 5.3; FIG. 23). In order to determine if the reduction in avidity is entirely due to the change from bivalent to monovalent binding or whether the loss of the Fc is also a factor, TPAi-1 RHP/RKA F(ab')2 was prepared and tested in the ELISA.

6.1 Preparation of TPAi-1 RHP/RKA F(Ab')2

5 mg TPAi-1 RHP/RKA IgG1κ antibody was digested with pepsin and the sample analysed by SDS-PAGE to confirm digestion and presence of molecules of the expected size for an F(ab')2 (non-reduced MW~110 kDa; FIG. 31.1). The F(ab')2 was then purified by gel filtration (FIG. 31.2), yielding 1.7 mg purified protein. The purity and integrity of the TPAi-1 RHP/RKA F(ab')2 preparation was checked by SDS-PAGE (FIG. 31.3).

6.2. Aggregation Analysis of TPAi-1 RHP/RKA F(Ab')2

TPAi-1 RHP/RKA F(ab')2 was injected at 0.4 mL/min into a size exclusion column in an HPLC system and analysed by multi-angle light scattering to determine the absolute molar mass and check for aggregation (FIG. 32). The F(ab')2 showed no signs of aggregation with an average molecular weight of 102.6 kDa. All samples are monodispersed (Mw/Mn<1.05). The mass recovery is 100% (calculated mass over injected mass), which indicates good protein recovery and that the sample does not stick to the column or contain insoluble aggregates, which would be retained by the guard column. Overall, the data suggest there are no aggregation concerns in the RHP/RKA F(ab')2 sample.

6.3. Antigen Binding by TPAi-1 RHP/RKA F(Ab')2

Binding activity of the purified TPAi-1 RHP/RKA F(ab')2 to the human tPA antigen was compared to that of the purified TPAi-1 RHP/RKA whole IgG1 antibody and RHP/RKA Fab in a binding ELISA. The binding curves of the RHP/RKA whole IgG1 and F(ab')2 are very similar, with EC50 values of 0.475 nM and 0.379 nM, respectively (FIG. 33). In contrast, the TPAi-1 RHP/RKA Fab binds with an EC50 value of 1.675 nM. The EC50 values for the IgG1 and Fab are in agreement with those seen in earlier experiments. There is a consistent 4-fold difference in avidity between these two formats.

The comparable binding of the whole IgG and F(ab')2 forms of TPAi-1 RHP/RKA shows that removal of the IgG1 Fc region does not affect avidity for human tPA. Thus the lower avidity exhibited by the TPAi-1 RHP/RKA Fab is entirely due to the change from bivalent to monovalent binding.

7.0 Assays of TPA Activity

The amidolytic activity of TPA was examined with 500 μM chromogenic substrate S2288. Pg activation by TPA was determined by monitoring the amidolytic activity of plasmin with 500 μM S2251. All experiments were performed at 37° C. in Tris-NaCl buffer (50 mM Tris-HCl, 100 mM NaCl, pH 7.4) as described previously (Sazonova I Y, McNamee R A, Houng A K, King S M, Hedstrom L, Reed G L. Reprogrammed streptokinases develop fibrin-targeting and dissolve blood clots with more potency than tissue plasminogen activator. J Thromb Haemost. 2009; 7: 1321-1328). Pg was pretreated with aprotinin-agarose beads for four hours at 4° C. to remove contaminating plasmin. In both assays, the absorbance at 405 nm (A405 nm) was continuously recorded. The amidolytic activity of TPA was determined from the initial slope of A405 nm with time. The activation rate of Pg by TPA to plasmin was calculated using the change in A405 nm per second squared over the initial period of reaction when net change of absorbance was less than 0.1, based on the method described by Longstaff et al. Longstaff C, Whitton C M. A proposed reference method for plasminogen activators that enables calculation of enzyme activities in SI units. J Thromb Haemost. 2004; 2: 1416-1421. In some runs, anti-TPA mAb or fibrin (Fn) fragment was incubated with TPA to examine their effect on TPA activity or Pg activation.

8.0 Fibrinolysis

Human clots were formed by mixing 20 μl human plasma (with trace amount of $^{125}$I-fibrinogen) with 5μl mixture of thrombin and calcium solution (final concentration: 1 Ul/ml thrombin and 10 mM $Ca^{2+}$ in test tube. The clot was incubated at 37° C. for one hour, followed by the addition of total 45 μl of varying amounts of human TPA with or without anti-TPA mAb. At sampling time, 10 μl supernatant was collected and the radioactivity of this sample was monitored using Cobra II gamma counter (Perkin-Elmer—Packard BioScience, Waltham, MA). After gamma counting, the samples were replaced in the test tube. The percent fibrinolysis was determined by the radioactivity in the supernatant divided by the initial clot radioactivity. The percent inhibition of fibrinolysis by mAbs was calculated by reference to the amount of fibrinolysis in the absence of mAbs.

Both chimeric TPAi-1 and humanized TPAi-1 (TPAi-1 RHP/RKA) significantly inhibited the dissolution of human clots induced by human TPA (FIG. 34).

TPAi-1 RHP/RKA Fab was also tested for its effects to inhibit plasma clot lysis in a dose response manner. Human plasma clots were formed by mixing together pooled fresh frozen (3.8% Sodium citrate) human plasma (50 μl), calcium and thrombin (10 μl), t-PA (10 μl, 1.5 nM) and purified mouse, chimeric, humanized mAb and the humanised Fab (0-140 nM). The dissolution or lysis of clots was monitored continuously at 37 deg. C. in a microtiter plate reader at A405 nm. The percentage of Lysis inhibition was determined by comparing (turbidity) the absorption reading at A405 nm at Baseline and at 1 hour. As seen in FIG. 35, approximately twice the amount TPAi-1 RHP/RKA Fab was required to produce equivalent inhibition as that produced by TPAi-1 RHP/RKA. This is consistent with the fact that the Fab is mono-valent whilst the mAb is bivalent.

9.0 Mouse Middle Cerebral Artery Thromboembolic Stroke and Bleeding

Animal studies that were performed in Dr. Reed's laboratory were approved by the UT-Memphis Institutional Animal Care and Use Committee. C57BL/6J adult mice (29 to 35 g, Jackson Lab, Bar Harbor ME) were anaesthetized with a mixture of 1.5-2% isoflurane and oxygen administered throughout the study. Rectal temperature was maintained at 3TC with a thermostat controlled heating pad. The left common carotid artery was isolated after a neck incision, and the external carotid, thyroid, and occipital arteries were ligated. Microvascular clips were temporarily placed on the common carotid and internal carotid arteries. A small arteriotomy was made on the external carotid artery for retrograde insertion of the PES catheter containing emboli $^{125}$I-fibrinogen (~5000 cpm/2 ul). The PES tubing containing the clots were inserted into the left external carotid artery, threaded into the internal cerebral artery up to origin of the middle cerebral artery (MCA). The thrombus was embolized at a speed of 0.45 ml/min in a volume of 100 ul saline. Continuous laser-Doppler monitoring was used to assess regional cerebral perfusion to ensure adequacy of embolization (perfusion decreased to <20% of pre-ischemic baseline). The right jugular vein was cannulated for drug administration. Mice received recombinant human TPA (rtPA) (10 mg/kg at 2.5 hr of ischemia) as a 20% bolus, 80% infusion over 30 minutes. Mice receiving mAb inhibitors were treated by stoichiometric dose of the murine, chimeric and humanized monoclonal antibodies given as an intravenous bolus 30 or 60 minutes after the TPA administration. Tail bleeding was assessed at 20 minutes after the TPA infusion and monitored for 30 minutes by measuring the time and amount of bleeding from tails pre-warmed for 5 mins in 3 mL of saline at 37° C. in a water bath as described. Hemoglobin (Hgb) loss from tail bleeding was measured using Drabkin's reagent kit according to manufacturer's data sheet (Sigma). Six hours after thromboembolism the animals were killed, the brain was isolated, cut into 2-mm coronal sections, and incubated in 2% triphenyltetrazolium chloride (Sigma, St. Louis, MO) solution for 30 mins at room temperature. The stained slices then were transferred into 4% formaldehyde for fixation. Images of four brain sections were captured with digital camera. The hemispheric size, area of gross hemorrhage and infarction area were digitally analyzed using Image Pro Plus 6.2 software and a modified Swanson's method (Swanson R A, Morton M T, Tsao-Wu G, Savalos R A, Davidson C, Sharp F R. A semi-automated method for measuring brain infarct volume. J Cereb Blood Flow Metab. 1990; 10:290-293). The amount of clot lysis was determined by comparing the residual thrombus radioactivity in the brain to that of the initial clot.

9.1 Limiting the Duration of r-tPA-Induced Plasminogen Activation Reduced Brain Injury and Bleeding The potent, specific effects of TPAi-1 allowed examination of whether the persistence of r-tPA-induced plasminogen activation is harmful during prolonged brain ischemia in a thromboembolic model with translational relevance to human stroke. Mice were randomly assigned to receive placebo, murine TPAi-1, chimeric TPAi-1 or humanized TPAi-1 (TPAi-1 RHP/RKA) thirty or sixty minutes following r-tPA bolus therapy, which was given 2.5 hours after middle cerebral artery thromboembolism. In these mice, bleeding following tail transection (under anesthesia) was monitored as an indicator of arterial and venous surgical hemorrhage related to persistent plasminogen activation. By comparison to mice receiving placebo, mice given murine TPAi-1 thirty or sixty minutes after r-tPA bolus, showed significant reductions in tail bleeding (FIG. 36). Treatment with chimeric TPAi-1 or humanized TPAi-1 (TPAi-1 RHP/RKA) also significantly reduced bleeding when compared to placebo (FIG. 36).

Treatment with r-tPA 2.5 hours after the onset of stroke was associated with significant brain hemorrhage (FIG. 37). However, in mice receiving murine TPAi-1 either thirty or sixty minutes after human TPA bolus therapy, there was a significant reduction in the size of hemorrhage (measured as percent of hemisphere) vs. mice treated with placebo. Similarly, mice treated with chimeric TPAi-1 or humanized TPAi-1 (TPAi-1 RHP/RKA) also showed significant decreases in brain hemorrhage when treated thirty minutes post-human TPA bolus (FIG. 37).

The murine TPAi-1 (m), as well as the chimeric (c) and the humanized Mab (h) (TPAi-1 RHP/RKA) decreased the amount of brain hemorrhage.

When compared to control mice, treatment with mTPAi-1 either 30 or 60 min. after initial r-tPA therapy significantly reduced brain infarction. There was also a significant reduction in brain infarction when mice are treated with either mtPAi-1 or htPAi-1 (TPAi-1 RHP/RKA) thirty minutes after initial tPA therapy. (FIG. 38).

10.0. Binding of Chimeric TPAi-1, Humanised TPAi-1 (RHP/RKA) and TPAi-1 (RHP/RKA) Fab to the TPA Mutant Tenecteplase The binding activity to the TPA mutant tenecteplase (TNK) was measured by Binding ELISA (2.4.1). The binding of the Fab (TPAi-1 RHP/PKA Fab) to Tenecteplase was compared to that of the chimeric mAb TPAi-1, and the humanised mAb TPAi-1 RHP/RKA and a control Fab (FIG. 4.3), finding that both bound with high affinity to TNK, albeit with a similar valency effect as seen with binding to recombinant human TPA (see 5.3 and FIG. 23). The EC50 binding concentrations were 0.762, 0.633, and 1.306 nM for the chimeric mAb TPAi-1, and the humanised mAb TPAi-1 RHP/RKA, and the Fab (TPAi-1 RHP/PKA Fab), respectively. No binding was detected for the control Fab.

All publications, patents and patent applications herein are incorporated by reference to the same extent as if each individual publication or patent application was specifically and individually indicated to be incorporated by reference. The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art. Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

```
SEQUENCE LISTINGS
                                                SEQ ID NO: 1
Met Asp Ala Met Lys Arg Gly Leu Cys Cys Val Leu Leu Leu Cys Gly

Ala Val Phe Val Ser Pro Ser Gln Glu Ile His Ala Arg Phe Arg Arg

Gly Ala Arg Ser Tyr Gln Val Ile Cys Arg Asp Glu Lys Thr Gln Met

Ile Tyr Gln Gln His Gln Ser Trp Leu Arg Pro Val Leu Arg Ser Asn

Arg Val Glu Tyr Cys Trp Cys Asn Ser Gly Arg Ala Gln Cys His Ser

Val Pro Val Lys Ser Cys Ser Glu Pro Arg Cys Phe Asn Gly Gly Thr

Cys Gln Gln Ala Leu Tyr Phe Ser Asp Phe Val Cys Gln Cys Pro Glu

Gly Phe Ala Gly Lys Cys Cys Glu Ile Asp Thr Arg Ala Thr Cys Tyr

Glu Asp Gln Gly Ile Ser Tyr Arg Gly Thr Trp Ser Thr Ala Glu Ser

Gly Ala Glu Cys Thr Asn Trp Asn Ser Ser Ala Leu Ala Gln Lys Pro

Tyr Ser Gly Arg Arg Pro Asp Ala Ile Arg Leu Gly Leu Gly Asn His
```

Asn Tyr Cys Arg Asn Pro Asp Arg Asp Ser Lys Pro Trp Cys Tyr Val

Phe Lys Ala Gly Lys Tyr Ser Ser Glu Phe Cys Ser Thr Pro Ala Cys

Ser Glu Gly Asn Ser Asp Cys Tyr Phe Gly Asn Gly Ser Ala Tyr Arg

Gly Thr His Ser Leu Thr Glu Ser Gly Ala Ser Cys Leu Pro Trp Asn

Ser Met Ile Leu Ile Gly Lys Val Tyr Thr Ala Gln Asn Pro Ser Ala

Gln Ala Leu Gly Leu Gly Lys His Asn Tyr Cys Arg Asn Pro Asp Gly

Asp Ala Lys Pro Trp Cys His Val Leu Lys Asn Arg Arg Leu Thr Trp

Glu Tyr Cys Asp Val Pro Ser Cys Ser Thr Cys Gly Leu Arg Gln Tyr

Ser Gln Pro Gln Phe Arg Ile Lys Gly Gly Leu Phe Ala Asp Ile Ala

Ser His Pro Trp Gln Ala Ala Ile Phe Ala Lys His Arg Arg Ser Pro

Gly Glu Arg Phe Leu Cys Gly Gly Ile Leu Ile Ser Ser Cys Trp Ile

Leu Ser Ala Ala His Cys Phe Gln Glu Arg Phe Pro Pro His His Leu

Thr Val Ile Leu Gly Arg Thr Tyr Arg Val Val Pro Gly Glu Glu Glu

Gln Lys Phe Glu Val Glu Lys Tyr Ile Val His Lys Glu Phe Asp Asp

Asp Thr Tyr Asp Asn Asp Ile Ala Leu Leu Gln Leu Lys Ser Asp Ser

Ser Arg Cys Ala Gln Glu Ser Ser Val Val Arg Thr Val Cys Leu Pro

Pro Ala Asp Leu Gln Leu Pro Asp Trp Thr Glu Cys Glu Leu Ser Gly

Tyr Gly Lys His Glu Ala Leu Ser Pro Phe Tyr Ser Glu Arg Leu Lys

Glu Ala His Val Arg Leu Tyr Pro Ser Ser Arg Cys Thr Ser Gln His

Leu Leu Asn Arg Thr Val Thr Asp Asn Met Leu Cys Ala Gly Asp Thr

Arg Ser Gly Gly Pro Gln Ala Asn Leu His Asp Ala Cys Gln Gly Asp

Ser Gly Gly Pro Leu Val Cys Leu Asn Asp Gly Arg Met Thr Leu Val

Gly Ile Ile Ser Trp Gly Leu Gly Cys Gly Gln Lys Asp Val Pro Gly

Val Tyr Thr Lys Val Thr Asn Tyr Leu Asp Trp Ile Arg Asp Asn Met

Arg Pro

SEQ ID NO: 2

Met Asp Ala Met Lys Arg Gly Leu Cys Cys Val Leu Leu Leu Cys Gly

Ala Val Phe Val Ser Pro Ser Gln Glu Ile His Ala Arg Phe Arg Arg

Gly Ala Arg Ser Tyr Gln Val Ile Cys Arg Asp Glu Lys Thr Gln Met

Ile Tyr Gln Gln His Gln Ser Trp Leu Arg Pro Val Leu Arg Ser Asn

Arg Val Glu Tyr Cys Trp Cys Asn Ser Gly Arg Ala Gln Cys His Ser

Val Pro Val Lys Ser Cys Ser Glu Pro Arg Cys Phe Asn Gly Gly Thr

Cys Gln Gln Ala Leu Tyr Phe Ser Asp Phe Val Cys Gln Cys Pro Glu

Gly Phe Ala Gly Lys Cys Cys Glu Ile Asp Thr Arg Ala Thr Cys Tyr

Glu Asp Gln Gly Ile Ser Tyr Arg Gly Thr Trp Ser Thr Ala Glu Ser

Gly Ala Glu Cys Thr Asn Trp Asn Ser Ser Ala Leu Ala Gln Lys Pro

Tyr Ser Gly Arg Arg Pro Asp Ala Ile Arg Leu Gly Leu Gly Asn His

Asn Tyr Cys Arg Asn Pro Asp Arg Asp Ser Lys Pro Trp Cys Tyr Val

Phe Lys Ala Gly Lys Tyr Ser Ser Glu Phe Cys Ser Thr Pro Ala Cys

Ser Glu Gly Asn Ser Asp Cys Tyr Phe Gly Asn Gly Ser Ala Tyr Arg

Gly Thr His Ser Leu Thr Glu Ser Gly Ala Ser Cys Leu Pro Trp Asn

-continued

Ser Met Ile Leu Ile Gly Lys Val Tyr Thr Ala Gln Asn Pro Ser Ala

Gln Ala Leu Gly Leu Gly Lys His Asn Tyr Cys Arg Asn Pro Asp Gly

Asp Ala Lys Pro Trp Cys His Val Leu Lys Asn Arg Arg Leu Thr Trp

Glu Tyr Cys Asp Val Pro Ser Cys Ser Thr Cys Gly Leu Arg Gln Tyr

Ser Gln Pro Gln Phe Arg Ile Lys Gly Gly Leu Phe Ala Asp Ile Ala

Ser His Pro Trp Gln Ala Ala Ile Phe Ala Lys His Arg Arg Ser Pro

Gly Glu Arg Phe Leu Cys Gly Gly Ile Leu Ile Ser Ser Cys Trp Ile

Leu Ser Ala Ala His Cys Phe Gln Glu Arg Phe Pro Pro His His Leu

Thr Val Ile Leu Gly Arg Thr Tyr Arg Val Val Pro Gly Glu Glu Glu

Gln Lys Phe Glu Val Glu Lys Tyr Ile Val His Lys Glu Phe Asp Asp

Asp Thr Tyr Asp Asn Asp Ile Ala Leu Leu Gln Leu Lys Ser Asp Ser

Ser Arg Cys Ala Gln Glu Ser Ser Val Val Arg Thr Val Cys Leu Pro

Pro Ala Asp Leu Gln Leu Pro Asp Trp Thr Glu Cys Glu Leu Ser Gly

Tyr Gly Lys His Glu Ala Leu Ser Pro Phe Tyr Ser Glu Arg Leu Lys

Glu Ala His Val Arg Leu Tyr Pro Ser Ser Arg Cys Thr Ser Gln His

Leu Leu Asn Arg Thr Val Thr Asp Asn Met Leu Cys Ala Gly Asp Thr

Arg Ser Gly Gly Pro Gln Ala Asn Leu His Asp Ala Cys Gln Gly Asp

Ser Gly Gly Pro Leu Val Cys Leu Asn Asp Gly Arg Met Thr Leu Val

Gly Ile Ile Ser Trp Gly Leu Gly Cys Gly Gln Lys Asp Val Pro Gly

Val Tyr Thr Lys Val Thr Asn Tyr Leu Asp Trp Ile Arg Asp Asn Met

Arg Pro

SEQ ID NO: 3

GNTSYW

SEQ ID NO: 4

WIT

SEQ ID NO: 5

RIDPGGGST

SEQ ID NO: 6

RIDPGGGSTYVNEIFKG

SEQ ID NO: 7

ASYYYAMAY

SEQ ID NO: 8

YYYAMAY

SEQ ID NO: 9

QSIVHSNGNTY

SEQ ID NO: 10

RSSQSIVHSNGNTYLE

SEQ ID NO: 11

KVS

SEQ ID NO: 12

KVSNRFS

SEQ ID NO: 13

FQGSHVPWT

SEQ ID NO: 14

QVQLVQSGAEVKKPGASVKVSCKASGNTSYWINWVRQATGQGLEWMGRIDPGGGSTG

YAQKFQGRVTMTRNTSISTAYMELSSLRSEDTAVYYCASYYYAMAYWGQGTLVTVSS

SEQ ID NO: 15

-continued

QVQLVQSGAEVKKPGASVKVSCKASGNTSYWINWVRQATGQGLEWMGRIDPGGGSTG

YAQKFQGRVTMTRDTSISTAYMELSSLRSEDTAVYYCASYYYAMAYWGQGTLVTVSS

SEQ ID NO: 16
QVQLVQSGAEVKKPGASVKVSCKASGNTSYWITWIRQATGQGLEWMGRIDPGGGSTYY

NQKFQGRVTLTVNTSISTAYMELSSLRSEDTAVYYCASYYYAMAYWGQGTLVTVSS

SEQ ID NO: 17
QVQLVQSGAEVKKPGASVKVSCKASGNTSYWITWVRQATGQGLEWMGRIDPGGGSTG

YAQKFQGRVTMTRNTSISTAYMELSSLRSEDTAVYYCASYYYAMAYWGQGTLVTVSS

SEQ ID NO: 18
QVQLVQSGAEVKKPGASVKVSCKASGNTSYWINWIRQATGQGLEWMGRIDPGGGSTG

YAQKFQGRVTMTRNTSISTAYMELSSLRSEDTAVYYCASYYYAMAYWGQGTLVTVSS

SEQ ID NO: 19
QVQLVQSGAEVKKPGASVKVSCKASGNTSYWINWVRQATGQGLEWMGRIDPGGGSTY

YAQKFQGRVTMTRNTSISTAYMELSSLRSEDTAVYYCASYYYAMAYWGQGTLVTVSS

SEQ ID NO: 20
QVQLVQSGAEVKKPGASVKVSCKASGNTSYWINWVRQATGQGLEWMGRIDPGGGSTG

YNQKFQGRVTMTRNTSISTAYMELSSLRSEDTAVYYCASYYYAMAYWGQGTLVTVSS

SEQ ID NO: 21
QVQLVQSGAEVKKPGASVKVSCKASGNTSYWINWVRQATGQGLEWMGRIDPGGGSTG

YAQKFQGRVTLTRNTSISTAYMELSSLRSEDTAVYYCASYYYAMAYWGQGTLVTVSS

SEQ ID NO: 22
QVQLVQSGAEVKKPGASVKVSCKASGNTSYWINWVRQATGQGLEWMGRIDPGGGSTG

YAQKFQGRVTMTVNTSISTAYMELSSLRSEDTAVYYCASYYYAMAYWGQGTLVTVSS

SEQ ID NO: 23
QVQLVQSGAEVKKPGASVKVSCKASGNTSYWITWVRQATGQGLEWMGRIDPGGGSTG

YAQKFQGRVTMTRDTSISTAYMELSSLRSEDTAVYYCASYYYAMAYWGQGTLVTVSS

SEQ ID NO: 24
QVQLVQSGAEVKKPGASVKVSCKASGNTSYWINWIRQATGQGLEWMGRIDPGGGSTG

YAQKFQGRVTMTRDTSISTAYMELSSLRSEDTAVYYCASYYYAMAYWGQGTLVTVSS

SEQ ID NO: 25
QVQLVQSGAEVKKPGASVKVSCKASGNTSYWINWVRQATGQGLEWMGRIDPGGGSTY

YAQKFQGRVTMTRDTSISTAYMELSSLRSEDTAVYYCASYYYAMAYWGQGTLVTVSS

SEQ ID NO: 26
QVQLVQSGAEVKKPGASVKVSCKASGNTSYWINWVRQATGQGLEWMGRIDPGGGSTG

YNQKFQGRVTMTRDTSISTAYMELSSLRSEDTAVYYCASYYYAMAYWGQGTLVTVSS

SEQ ID NO: 27
QVQLVQSGAEVKKPGASVKVSCKASGNTSYWINWVRQATGQGLEWMGRIDPGGGSTG

YAQKFQGRVTLTRDTSISTAYMELSSLRSEDTAVYYCASYYYAMAYWGQGTLVTVSS

SEQ ID NO: 28
QVQLVQSGAEVKKPGASVKVSCKASGNTSYWINWVRQATGQGLEWMGRIDPGGGSTG

YAQKFQGRVTMTVDTSISTAYMELSSLRSEDTAVYYCASYYYAMAYWGQGTLVTVSS

SEQ ID NO: 29
DVVMTQSPLSLPVTPGEPASISCRSSQSIVHSNGNTYLDWYLQKPGQSPQLLIYKVSNRA

SGVPDRFSGSGSGTDFTLKISRVEAEDVGVYYCFQGSHVPWTFGGGTKVEIK

SEQ ID NO: 30
DVVVTQSPLSLPVTPGEPASISCRSSQSIVHSNGNTYLEWYLQKPGQSPQLLIYKVSNRF

SGVPDRFSGSGSGTDFTLKISRVEAEDVGVYYCFQGSHVPWTFGGGTKVEIK

SEQ ID NO: 31
QVQLVQSGAEVKKPGASVKVSCKASGNTSYWINWVRQATGQGLEWMGRIDPGGGSTG

-continued

YAQKFQGRVTMTRNTSISTAYMELSSLRSEDTAVYYCASYYYAMAYWGQGTLVTVSSA
STKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSC

SEQ ID NO: 32
QVQLVQSGAEVKKPGASVKVSCKASGNTSYWINWVRQATGQGLEWMGRIDPGGGSTG
YAQKFQGRVTMTRDTSISTAYMELSSLRSEDTAVYYCASYYYAMAYWGQGTLVTVSSA
STKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSC

SEQ ID NO: 33
DVVMTQSPLSLPVTPGEPASISCRSSQSIVHSNGNTYLDWYLQKPGQSPQLLIYKVSNRA
SGVPDRFSGSGSGTDFTLKISRVEAEDVGVYYCFQGSHVPWTFGGGTKVEIKRTVAAPS
VFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC

SEQ ID NO: 34
GGGSGGGSGGGS

SEQ ID NO: 35
GGGSGGGSGGGSGGGS

SEQ ID NO: 36
GGSSRSSSSGGGGSGGGG

SEQ ID NO: 37
GSTSGSGKSSEGKG

SEQ ID NO: 38
DVVMTQSPLSLPVTPGEPASISCRSSQSIVHSNGNTYLDWYLQKPGQSPQLLIYKVSNRA
SGVPDRFSGSGSGTDFTLKISRVEAEDVGVYYCFQGSHVPWTFGGGTKVEIK
GGGSGGGSGGGSQVQLVQSGAEVKKPGASVKVSCKASGNTSYWINWVRQATGQGLE
WMGRIDPGGGSTGYAQKFQGRVTMTRDTSISTAYMELSSLRSEDTAVYYCASYYYAMA
YWGQGTLVTVSS

SEQ ID NO: 39
QVQLVQSGAEVKKPGASVKVSCKASGNTSYWINWVRQATGQGLEWMGRIDPGGGSTG
YAQKFQGRVTMTRDTSISTAYMELSSLRSEDTAVYYCASYYYAMAYWGQGTLVTVSSG
GGSGGGSGGGSDVVMTQSPLSLPVTPGEPASISCRSSQSIVHSNGNTYLDVVYLQKPGQ
SPQLLIYKVSNRASGVPDRFSGSGSGTDFTLKISRVEAEDVGVYYCFQGSHVPWTFGGG
TKVEIK

SEQ ID NO: 40
QVQLVQSGAEVKKPGASVKVSCKASGNTSYWINWVRQATGQGLEWMGRIDPGGGSTG
YAQKFQGRVTMTRNTSISTAYMELSSLRSEDTAVYYCASYYYAMAYWGQGTLVTVSSA
STKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKS
RWQQGNVFSCSVMHEALHNHYTQKSLSLSPGK

SEQ ID NO: 41
QVQLVQSGAEVKKPGASVKVSCKASGNTSYWINWVRQATGQGLEWMGRIDPGGGSTG
YAQKFQGRVTMTRDTSISTAYMELSSLRSEDTAVYYCASYYYAMAYWGQGTLVTVSSA

-continued

STKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFLYSKLTVDKS

RWQQGNVFSCSVMHEALHNHYTQKSLSLSPGK

SEQ ID NO: 42

DVVMTQSPLSLPVTPGEPASISCRSSQSIVHSNGNTYLDWYLQKPGQSPQLLIYK

VSNRASGVPDRFSGSGSGTDFTLKISRVEAEDVGVYYCFQGSHVPWTFGGGTKVEIKRT

VAAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

---

What is claimed is:

1. An antibody molecule that binds specifically to a human tissue plasminogen activator (TPA) or a TPA mutant to inhibit degradation of human fibrin clots, wherein the antibody has sub-nanomolar affinity to inhibit fibrin-dependent plasminogen activation with an IC50<5 nM, and wherein the amino acid sequence of said TPA mutant has at least 65% identity to SEQ ID NO: 1 or SEQ ID NO: 2; wherein the antibody comprises a heavy chain variable domain with a CDR1 of SEQ ID NO: 3 or 4, a CDR2 of SEQ ID NO: 5 or 6, and a CDR3 of SEQ ID NO: 7 or 8, and a light chain variable domain with a CDR1 of SEQ ID NO: 9 or 10, a CDR2 of SEQ ID NO: 11 or 12, and a CDR3 of SEQ ID NO: 13, wherein the antibody molecule is a humanized antibody or an antigen binding fragment of a humanized antibody.

2. The antibody molecule of claim 1 which comprises a heavy chain variable domain with a CDR1 of SEQ ID NO: 3, a CDR2 of SEQ ID NO: 5, and a CDR3 of SEQ ID NO: 7, and a light chain variable domain with a CDR1 of SEQ ID NO: 9, and a CDR2 of SEQ ID NO: 11.

3. The antibody molecule of claim 1 which comprises a heavy chain variable domain selected from SEQ ID NOs: 14 to 28 and a light chain variable domain of SEQ ID NO: 29 or 30.

4. The antibody molecule of claim 3 which comprises a heavy chain variable domain selected from SEQ ID NOs: 14 to 28, and a light chain variable domain of SEQ ID NO: 29.

5. The antibody molecule of claim 3 which comprises a heavy chain variable domain of SEQ ID NO: 14, and a light chain variable domain of SEQ ID No: 29, or a heavy chain variable domain of SEQ ID NO: 15, and a light chain variable domain of SEQ ID No: 29, or a heavy chain variable domain of SEQ ID NO: 14, and a light chain variable domain of SEQ ID No: 30, or a heavy chain variable domain of SEQ ID NO: 15, and a light chain variable domain of SEQ ID No: 30.

6. The antibody molecule of claim 1, wherein the humanized antibody or antigen binding fragment of a humanized antibody is a Fab, Fab', or F(ab')2 fragment or a single chain antibody (ScFv).

7. The antibody molecule of claim 6, wherein the humanized antibody or antigen binding fragment of a humanized antibody is a Fab, Fab', or F(ab')2 fragment.

8. The antibody molecule of claim 6 which is a scFv, wherein the heavy chain variable domain and the light chain variable domain are linked to each other through a linker peptide of SEQ ID NO: 34, SEQ ID NO: 35, SEQ ID NO: 36, or SEQ ID NO: 37.

9. The antibody molecule of claim 8 which comprises SEQ ID NO: 38, or SEQ ID NO:39.

10. The antibody molecule of claim 6 having a heavy chain comprising SEQ ID NO: 40 or SEQ ID NO: 41, and a light chain comprising SEQ ID NO: 42.

11. The antibody of claim 6 which is a Fab molecule having a Fd fragment comprising SEQ ID NO: 31 or SEQ ID NO: 32, and a light chain comprising SEQ ID NO: 33.

12. A pharmaceutical composition comprising an antibody molecule of claim 1 and a pharmaceutically acceptable carrier.

13. A method of treatment of TPA induced hemorrhage or systemic hemorrhage after TPA treatment, the method comprising administering an effective amount of an antibody molecule of claim 1 to a subject in need thereof.

14. A method of manufacturing an antibody molecule of claim 1, comprising:

(a) providing a host cell comprising one or more nucleic acids encoding said antibody molecule in functional association with an expression control sequence, (b) culturing said host cell, and (c) recovering the antibody molecule from the cell culture.

15. A kit comprising an antibody of claim 1, or a pharmaceutical composition thereof.

16. The kit according to claim 15, comprising a human tissue plasminogen activator (TPA) or a TPA mutant wherein the amino acid sequence of said TPA mutant has at least 65% identity to SEQ ID NO: 1 or SEQ ID NO: 2.

17. The kit according to claim 16, wherein the human tissue plasminogen activator (TPA) or TPA mutant is alteplase, reteplase or tenecteplase.

18. The kit according to claim 17 comprising:
(a) a pharmaceutical composition comprising human tissue plasminogen activator (TPA) or TPA mutant selected from alteplase, reteplase and tenecteplase;
(b) a container; and
(c) a label.

19. A kit according to claim 17 comprising:
(a) a first pharmaceutical composition comprising human tissue plasminogen activator (TPA) or TPA mutant selected from alteplase, reteplase and tenecteplase;
(b) a second pharmaceutical composition comprising the antibody; and
(c) instructions for separate administration of the first and second pharmaceutical compositions to a subject, wherein the first and second pharmaceutical compositions are contained in separate containers and the second pharmaceutical composition is administered to a subject requiring treatment or prevention of systemic haemorrhage after TPA treatment.

* * * * *

SEQUENCE LISTING

<160> NUMBER OF SEQ ID NOS: 42

<210> SEQ ID NO 1
<211> LENGTH: 562
<212> TYPE: PRT
<213> ORGANISM: Artificial Sequence
<220> FEATURE:
<223> OTHER INFORMATION: recombinant human TPA

<400> SEQUENCE: 1

Met Asp Ala Met Lys Arg Gly Leu Cys Cys Val Leu Leu Leu Cys Gly
1 5 10 15

Ala Val Phe Val Ser Pro Ser Gln Glu Ile His Ala Arg Phe Arg Arg
20 25 30

Gly Ala Arg Ser Tyr Gln Val Ile Cys Arg Asp Glu Lys Thr Gln Met
35 40 45

Ile Tyr Gln Gln His Gln Ser Trp Leu Arg Pro Val Leu Arg Ser Asn
50 55 60

Arg Val Glu Tyr Cys Trp Cys Asn Ser Gly Arg Ala Gln Cys His Ser
65 70 75 80

Val Pro Val Lys Ser Cys Ser Glu Pro Arg Cys Phe Asn Gly Gly Thr
85 90 95

Cys Gln Gln Ala Leu Tyr Phe Ser Asp Phe Val Cys Gln Cys Pro Glu
100 105 110

Gly Phe Ala Gly Lys Cys Cys Glu Ile Asp Thr Arg Ala Thr Cys Tyr
115 120 125

Glu Asp Gln Gly Ile Ser Tyr Arg Gly Thr Trp Ser Thr Ala Glu Ser
130 135 140

Gly Ala Glu Cys Thr Asn Trp Asn Ser Ser Ala Leu Ala Gln Lys Pro
145 150 155 160

Tyr Ser Gly Arg Arg Pro Asp Ala Ile Arg Leu Gly Leu Gly Asn His
165 170 175

Asn Tyr Cys Arg Asn Pro Asp Arg Asp Ser Lys Pro Trp Cys Tyr Val
180 185 190

Phe Lys Ala Gly Lys Tyr Ser Ser Glu Phe Cys Ser Thr Pro Ala Cys
195 200 205

Ser Glu Gly Asn Ser Asp Cys Tyr Phe Gly Asn Gly Ser Ala Tyr Arg
210 215 220

Gly Thr His Ser Leu Thr Glu Ser Gly Ala Ser Cys Leu Pro Trp Asn

```
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
        355                 360                 365

Thr Val Ile Leu Gly Arg Thr Tyr Arg Val Val Pro Gly Glu Glu Glu
    370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
        435                 440                 445

Tyr Gly Lys His Glu Ala Leu Ser Pro Phe Tyr Ser Glu Arg Leu Lys
    450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
            500                 505                 510

Ser Gly Gly Pro Leu Val Cys Leu Asn Asp Gly Arg Met Thr Leu Val
        515                 520                 525

Gly Ile Ile Ser Trp Gly Leu Gly Cys Gly Gln Lys Asp Val Pro Gly
    530                 535                 540

Val Tyr Thr Lys Val Thr Asn Tyr Leu Asp Trp Ile Arg Asp Asn Met
545                 550                 555                 560

Arg Pro


<210> SEQ ID NO 2
<211> LENGTH: 562
<212> TYPE: PRT
<213> ORGANISM: Artificial Sequence
<220> FEATURE:
<223> OTHER INFORMATION: recombinant human TPA

<400> SEQUENCE: 2

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30
```

-continued

```
Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
        355                 360                 365

Thr Val Ile Leu Gly Arg Thr Tyr Arg Val Val Pro Gly Glu Glu Glu
    370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
        435                 440                 445
```

Tyr Gly Lys His Glu Ala Leu Ser Pro Phe Tyr Ser Glu Arg Leu Lys
    450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
            500                 505                 510

Ser Gly Gly Pro Leu Val Cys Leu Asn Asp Gly Arg Met Thr Leu Val
        515                 520                 525

Gly Ile Ile Ser Trp Gly Leu Gly Cys Gly Gln Lys Asp Val Pro Gly
    530                 535                 540

Val Tyr Thr Lys Val Thr Asn Tyr Leu Asp Trp Ile Arg Asp Asn Met
545                 550                 555                 560

Arg Pro

<210> SEQ ID NO 3
<211> LENGTH: 6
<212> TYPE: PRT
<213> ORGANISM: Artificial Sequence
<220> FEATURE:
<223> OTHER INFORMATION: VH CDR1 A

<400> SEQUENCE: 3

Gly Asn Thr Ser Tyr Trp
1               5

<210> SEQ ID NO 4
<211> LENGTH: 3
<212> TYPE: PRT
<213> ORGANISM: Artificial Sequence
<220> FEATURE:
<223> OTHER INFORMATION: VH CDR1 B

<400> SEQUENCE: 4

Trp Ile Thr
1

<210> SEQ ID NO 5
<211> LENGTH: 9
<212> TYPE: PRT
<213> ORGANISM: Artificial Sequence
<220> FEATURE:
<223> OTHER INFORMATION: VH CDR2 A

<400> SEQUENCE: 5

Arg Ile Asp Pro Gly Gly Gly Ser Thr
1               5

<210> SEQ ID NO 6
<211> LENGTH: 17
<212> TYPE: PRT
<213> ORGANISM: Artificial Sequence
<220> FEATURE:
<223> OTHER INFORMATION: VH CDR2 B

<400> SEQUENCE: 6

Arg Ile Asp Pro Gly Gly Gly Ser Thr Tyr Val Asn Glu Ile Phe Lys
1               5                   10                  15

Gly

<210> SEQ ID NO 7

<211> LENGTH: 9
<212> TYPE: PRT
<213> ORGANISM: Artificial Sequence
<220> FEATURE:
<223> OTHER INFORMATION: VH CDR3 A

<400> SEQUENCE: 7

Ala Ser Tyr Tyr Tyr Ala Met Ala Tyr
1 5

<210> SEQ ID NO 8
<211> LENGTH: 7
<212> TYPE: PRT
<213> ORGANISM: Artificial Sequence
<220> FEATURE:
<223> OTHER INFORMATION: VH CDR3 B

<400> SEQUENCE: 8

Tyr Tyr Tyr Ala Met Ala Tyr
1 5

<210> SEQ ID NO 9
<211> LENGTH: 11
<212> TYPE: PRT
<213> ORGANISM: Artificial Sequence
<220> FEATURE:
<223> OTHER INFORMATION: VK CDR1 A

<400> SEQUENCE: 9

Gln Ser Ile Val His Ser Asn Gly Asn Thr Tyr
1 5 10

<210> SEQ ID NO 10
<211> LENGTH: 16
<212> TYPE: PRT
<213> ORGANISM: Artificial Sequence
<220> FEATURE:
<223> OTHER INFORMATION: VK CDR1 B

<400> SEQUENCE: 10

Arg Ser Ser Gln Ser Ile Val His Ser Asn Gly Asn Thr Tyr Leu Glu
1 5 10 15

<210> SEQ ID NO 11
<211> LENGTH: 3
<212> TYPE: PRT
<213> ORGANISM: Artificial Sequence
<220> FEATURE:
<223> OTHER INFORMATION: VK CDR2 A

<400> SEQUENCE: 11

Lys Val Ser
1

<210> SEQ ID NO 12
<211> LENGTH: 7
<212> TYPE: PRT
<213> ORGANISM: Artificial Sequence
<220> FEATURE:
<223> OTHER INFORMATION: VK CDR2 B

<400> SEQUENCE: 12

Lys Val Ser Asn Arg Phe Ser
1 5

<210> SEQ ID NO 13
<211> LENGTH: 9

<212> TYPE: PRT
<213> ORGANISM: Artificial Sequence
<220> FEATURE:
<223> OTHER INFORMATION: VK CDR3

<400> SEQUENCE: 13

Phe Gln Gly Ser His Val Pro Trp Thr
1 5

<210> SEQ ID NO 14
<211> LENGTH: 114
<212> TYPE: PRT
<213> ORGANISM: Artificial Sequence
<220> FEATURE:
<223> OTHER INFORMATION: Engineered AntibodySequence, Heavy Chain Variable Domain

<400> SEQUENCE: 14

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly
50 55 60

Arg Val Thr Met Thr Arg Asn Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 15
<211> LENGTH: 114
<212> TYPE: PRT
<213> ORGANISM: Artificial Sequence
<220> FEATURE:
<223> OTHER INFORMATION: Engineered Antibody Sequence, Heavy Chain Variable Domain

<400> SEQUENCE: 15

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly
50 55 60

Arg Val Thr Met Thr Arg Asp Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 16
<211> LENGTH: 114
<212> TYPE: PRT
<213> ORGANISM: Artificial Sequence
<220> FEATURE:
<223> OTHER INFORMATION: Engineered Antibody Sequence, Heavy Chain Variable Domain

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Ser Tyr Trp Ile
            20                  25                  30

Thr Trp Ile Arg Gln Ala Thr Gly Gln Gly Leu Glu Trp Met Gly Arg
        35                  40                  45

Ile Asp Pro Gly Gly Gly Ser Thr Tyr Tyr Asn Gln Lys Phe Gln Gly
    50                  55                  60

Arg Val Thr Leu Thr Val Asn Thr Ser Ile Ser Thr Ala Tyr Met Glu
65                  70                  75                  80

Leu Ser Ser Leu Arg Ser Glu Asp Thr Ala Val Tyr Tyr Cys Ala Ser
                85                  90                  95

Tyr Tyr Tyr Ala Met Ala Tyr Trp Gly Gln Gly Thr Leu Val Thr Val
            100                 105                 110

Ser Ser
```

<210> SEQ ID NO 17
<211> LENGTH: 114
<212> TYPE: PRT
<213> ORGANISM: Artificial Sequence
<220> FEATURE:
<223> OTHER INFORMATION: Engineered Antibody Sequence, Heavy Chain Variable Domain

<400> SEQUENCE: 17

```
Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Ser Tyr Trp Ile
            20                  25                  30

Thr Trp Val Arg Gln Ala Thr Gly Gln Gly Leu Glu Trp Met Gly Arg
        35                  40                  45

Ile Asp Pro Gly Gly Gly Ser Thr Gly Tyr Ala Gln Lys Phe Gln Gly
    50                  55                  60

Arg Val Thr Met Thr Arg Asn Thr Ser Ile Ser Thr Ala Tyr Met Glu
65                  70                  75                  80

Leu Ser Ser Leu Arg Ser Glu Asp Thr Ala Val Tyr Tyr Cys Ala Ser
                85                  90                  95

Tyr Tyr Tyr Ala Met Ala Tyr Trp Gly Gln Gly Thr Leu Val Thr Val
            100                 105                 110

Ser Ser
```

<210> SEQ ID NO 18
<211> LENGTH: 114
<212> TYPE: PRT
<213> ORGANISM: Artificial Sequence
<220> FEATURE:
<223> OTHER INFORMATION: Engineered Antibody Sequence, Heavy Chain Variable Domain

<400> SEQUENCE: 18

```
Gln Val Gln Leu Val Gln Ser Gly Ala Glu Val Lys Lys Pro Gly Ala
```

1 5 10 15

Ser Val Lys Val Ser Cys Lys Ala Ser Gly Asn Thr Ser Tyr Trp Ile
20 25 30

Asn Trp Ile Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly
50 55 60

Arg Val Thr Met Thr Arg Asn Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 19
<211> LENGTH: 114
<212> TYPE: PRT
<213> ORGANISM: Artificial Sequence
<220> FEATURE:
<223> OTHER INFORMATION: Engineered Antibody Sequence, Heavy Chain Variable Domain

<400> SEQUENCE: 19

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Tyr Tyr Ala Gln Lys Phe Gln Gly
50 55 60

Arg Val Thr Met Thr Arg Asn Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 20
<211> LENGTH: 114
<212> TYPE: PRT
<213> ORGANISM: Artificial Sequence
<220> FEATURE:
<223> OTHER INFORMATION: Engineered Antibody Sequence, Heavy Chain Variable Domain

<400> SEQUENCE: 20

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Asn Gln Lys Phe Gln Gly
50 55 60

Arg Val Thr Met Thr Arg Asn Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 21
<211> LENGTH: 114
<212> TYPE: PRT
<213> ORGANISM: Artificial Sequence
<220> FEATURE:
<223> OTHER INFORMATION: Engineered Antibody Sequence, Heavy Chain Variable Domain

<400> SEQUENCE: 21

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly
50 55 60

Arg Val Thr Leu Thr Arg Asn Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 22
<211> LENGTH: 114
<212> TYPE: PRT
<213> ORGANISM: Artificial Sequence
<220> FEATURE:
<223> OTHER INFORMATION: Engineered Antibosy Sequence, Heavy Chain Variable Domain

<400> SEQUENCE: 22

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly
50 55 60

Arg Val Thr Met Thr Val Asn Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 23
<211> LENGTH: 114
<212> TYPE: PRT
<213> ORGANISM: Artificial Sequence
<220> FEATURE:
<223> OTHER INFORMATION: Engineered Antibody Sequence, Heavy Chain
Variable Domain

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Ser Tyr Trp Ile
            20                  25                  30

Thr Trp Val Arg Gln Ala Thr Gly Gln Gly Leu Glu Trp Met Gly Arg
        35                  40                  45

Ile Asp Pro Gly Gly Gly Ser Thr Gly Tyr Ala Gln Lys Phe Gln Gly
    50                  55                  60

Arg Val Thr Met Thr Arg Asp Thr Ser Ile Ser Thr Ala Tyr Met Glu
65                  70                  75                  80

Leu Ser Ser Leu Arg Ser Glu Asp Thr Ala Val Tyr Tyr Cys Ala Ser
                85                  90                  95

Tyr Tyr Tyr Ala Met Ala Tyr Trp Gly Gln Gly Thr Leu Val Thr Val
            100                 105                 110

Ser Ser
```

<210> SEQ ID NO 24
<211> LENGTH: 114
<212> TYPE: PRT
<213> ORGANISM: Artificial Sequence
<220> FEATURE:
<223> OTHER INFORMATION: Engineered Antibody Sequence, Heavy Chain
Variable Domain

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Ser Tyr Trp Ile
            20                  25                  30

Asn Trp Ile Arg Gln Ala Thr Gly Gln Gly Leu Glu Trp Met Gly Arg
        35                  40                  45

Ile Asp Pro Gly Gly Gly Ser Thr Gly Tyr Ala Gln Lys Phe Gln Gly
    50                  55                  60

Arg Val Thr Met Thr Arg Asp Thr Ser Ile Ser Thr Ala Tyr Met Glu
65                  70                  75                  80

Leu Ser Ser Leu Arg Ser Glu Asp Thr Ala Val Tyr Tyr Cys Ala Ser
                85                  90                  95

Tyr Tyr Tyr Ala Met Ala Tyr Trp Gly Gln Gly Thr Leu Val Thr Val
            100                 105                 110

Ser Ser
```

<210> SEQ ID NO 25
<211> LENGTH: 114
<212> TYPE: PRT
<213> ORGANISM: Artificial Sequence
<220> FEATURE:
<223> OTHER INFORMATION: Engineered Antibody Sequence, Heavy Chain
Variable Domain

<400> SEQUENCE: 25

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Tyr Tyr Ala Gln Lys Phe Gln Gly
50 55 60

Arg Val Thr Met Thr Arg Asp Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 26
<211> LENGTH: 114
<212> TYPE: PRT
<213> ORGANISM: Artificial Sequence
<220> FEATURE:
<223> OTHER INFORMATION: Engineered Antibody Sequence, Heavy Chain
Variable Domain

<400> SEQUENCE: 26

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Asn Gln Lys Phe Gln Gly
50 55 60

Arg Val Thr Met Thr Arg Asp Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 27
<211> LENGTH: 114
<212> TYPE: PRT
<213> ORGANISM: Artificial Sequence
<220> FEATURE:
<223> OTHER INFORMATION: Engineered Antibody Sequence, Heavy Chain
Variable Domain

<400> SEQUENCE: 27

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly
50 55 60

Arg Val Thr Leu Thr Arg Asp Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 28
<211> LENGTH: 114
<212> TYPE: PRT
<213> ORGANISM: Artificial Sequence
<220> FEATURE:
<223> OTHER INFORMATION: Engineered Antibody Sequence, Heavy Chain Variable Domain

<400> SEQUENCE: 28

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly
50 55 60

Arg Val Thr Met Thr Val Asp Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser

<210> SEQ ID NO 29
<211> LENGTH: 112
<212> TYPE: PRT
<213> ORGANISM: Artificial Sequence
<220> FEATURE:
<223> OTHER INFORMATION: Engineered Antibody Sequence, Light Chain Variable Domain

<400> SEQUENCE: 29

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Ile Val His Ser
20 25 30

Asn Gly Asn Thr Tyr Leu Asp Trp Tyr Leu Gln Lys Pro Gly Gln Ser
35 40 45

Pro Gln Leu Leu Ile Tyr Lys Val Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Trp Thr Phe Gly Gly Gly Thr Lys Val Glu Ile Lys
100 105 110

<210> SEQ ID NO 30
<211> LENGTH: 112
<212> TYPE: PRT
<213> ORGANISM: Artificial Sequence
<220> FEATURE:
<223> OTHER INFORMATION: Engineered Antibody Sequence, Light Chain Variable Domain

<400> SEQUENCE: 30

Asp Val Val Val Thr Gln Ser Pro Leu Ser Leu Pro Val Thr Pro Gly
1 5 10 15

Glu Pro Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Trp Thr Phe Gly Gly Gly Thr Lys Val Glu Ile Lys
100 105 110

<210> SEQ ID NO 31
<211> LENGTH: 217
<212> TYPE: PRT
<213> ORGANISM: Artificial Sequence
<220> FEATURE:
<223> OTHER INFORMATION: Engineered Antibody Sequence, Fab Fd

<400> SEQUENCE: 31

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly
50 55 60

Arg Val Thr Met Thr Arg Asn Thr Ser Ile Ser Thr Ala Tyr Met Glu
65 70 75 80

Leu Ser Ser Leu Arg Ser Glu Asp Thr Ala Val Tyr Tyr Cys Ala Ser
85 90 95

Tyr Tyr Tyr Ala Met Ala Tyr Trp Gly Gln Gly Thr Leu Val Thr Val
100 105 110

Ser Ser Ala Ser Thr Lys Gly Pro Ser Val Phe Pro Leu Ala Pro Ser
115 120 125

Ser Lys Ser Thr Ser Gly Gly Thr Ala Ala Leu Gly Cys Leu Val Lys
130 135 140

Asp Tyr Phe Pro Glu Pro Val Thr Val Ser Trp Asn Ser Gly Ala Leu
145 150 155 160

Thr Ser Gly Val His Thr Phe Pro Ala Val Leu Gln Ser Ser Gly Leu
165 170 175

Tyr Ser Leu Ser Ser Val Val Thr Val Pro Ser Ser Ser Leu Gly Thr
180 185 190

Gln Thr Tyr Ile Cys Asn Val Asn His Lys Pro Ser Asn Thr Lys Val
195 200 205

```
Asp Lys Lys Val Glu Pro Lys Ser Cys
    210                 215


<210> SEQ ID NO 32
<211> LENGTH: 217
<212> TYPE: PRT
<213> ORGANISM: Artificial Sequence
<220> FEATURE:
<223> OTHER INFORMATION: Engineered Antibody Sequence, Fab Fd

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Ser Tyr Trp Ile
            20                  25                  30

Asn Trp Val Arg Gln Ala Thr Gly Gln Gly Leu Glu Trp Met Gly Arg
        35                  40                  45

Ile Asp Pro Gly Gly Gly Ser Thr Gly Tyr Ala Gln Lys Phe Gln Gly
    50                  55                  60

Arg Val Thr Met Thr Arg Asp Thr Ser Ile Ser Thr Ala Tyr Met Glu
65                  70                  75                  80

Leu Ser Ser Leu Arg Ser Glu Asp Thr Ala Val Tyr Tyr Cys Ala Ser
                85                  90                  95

Tyr Tyr Tyr Ala Met Ala Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys
    210                 215


<210> SEQ ID NO 33
<211> LENGTH: 219
<212> TYPE: PRT
<213> ORGANISM: Artificial Sequence
<220> FEATURE:
<223> OTHER INFORMATION: Engineered Antibody Sequence, Fab light chain

<400> SEQUENCE: 33

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Lys Val Ser Asn Arg Ala Ser Gly Val Pro
    50                  55                  60

Asp Arg Phe Ser Gly Ser Gly Ser Gly Thr Asp Phe Thr Leu Lys Ile
```

```
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 34
<211> LENGTH: 12
<212> TYPE: PRT
<213> ORGANISM: Artificial Sequence
<220> FEATURE:
<223> OTHER INFORMATION: scFv linker

<400> SEQUENCE: 34

Gly Gly Gly Ser Gly Gly Gly Ser Gly Gly Gly Ser
1               5                   10


<210> SEQ ID NO 35
<211> LENGTH: 16
<212> TYPE: PRT
<213> ORGANISM: Artificial Sequence
<220> FEATURE:
<223> OTHER INFORMATION: scFv linker

<400> SEQUENCE: 35

Gly Gly Gly Ser Gly Gly Gly Ser Gly Gly Gly Ser Gly Gly Gly Ser
1               5                   10                  15


<210> SEQ ID NO 36
<211> LENGTH: 18
<212> TYPE: PRT
<213> ORGANISM: Artificial Sequence
<220> FEATURE:
<223> OTHER INFORMATION: scFv linker

<400> SEQUENCE: 36

Gly Gly Ser Ser Arg Ser Ser Ser Ser Gly Gly Gly Gly Ser Gly Gly
1               5                   10                  15

Gly Gly


<210> SEQ ID NO 37
<211> LENGTH: 14
<212> TYPE: PRT
<213> ORGANISM: Artificial Sequence
<220> FEATURE:
<223> OTHER INFORMATION: scFv linker

<400> SEQUENCE: 37
```

Gly Ser Thr Ser Gly Ser Gly Lys Ser Ser Glu Gly Lys Gly
1 5 10

<210> SEQ ID NO 38
<211> LENGTH: 238
<212> TYPE: PRT
<213> ORGANISM: Artificial Sequence
<220> FEATURE:
<223> OTHER INFORMATION: Engineered Antibody Sequence, scFv

<400> SEQUENCE: 38

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Ile Val His Ser
20 25 30

Asn Gly Asn Thr Tyr Leu Asp Trp Tyr Leu Gln Lys Pro Gly Gln Ser
35 40 45

Pro Gln Leu Leu Ile Tyr Lys Val Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Trp Thr Phe Gly Gly Gly Thr Lys Val Glu Ile Lys
100 105 110

Gly Gly Gly Ser Gly Gly Gly Ser Gly Gly Gly Ser Gln Val Gln Leu
115 120 125

Val Gln Ser Gly Ala Glu Val Lys Lys Pro Gly Ala Ser Val Lys Val
130 135 140

Ser Cys Lys Ala Ser Gly Asn Thr Ser Tyr Trp Ile Asn Trp Val Arg
145 150 155 160

Gln Ala Thr Gly Gln Gly Leu Glu Trp Met Gly Arg Ile Asp Pro Gly
165 170 175

Gly Gly Ser Thr Gly Tyr Ala Gln Lys Phe Gln Gly Arg Val Thr Met
180 185 190

Thr Arg Asp Thr Ser Ile Ser Thr Ala Tyr Met Glu Leu Ser Ser Leu
195 200 205

Arg Ser Glu Asp Thr Ala Val Tyr Tyr Cys Ala Ser Tyr Tyr Tyr Ala
210 215 220

Met Ala Tyr Trp Gly Gln Gly Thr Leu Val Thr Val Ser Ser
225 230 235

<210> SEQ ID NO 39
<211> LENGTH: 238
<212> TYPE: PRT
<213> ORGANISM: Artificial Sequence
<220> FEATURE:
<223> OTHER INFORMATION: Engineered Antibody Sequence, scFv

<400> SEQUENCE: 39

Gln Val Gln Leu Val Gln Ser Gly Ala Glu Val Lys Lys Pro Gly Ala
1 5 10 15

Ser Val Lys Val Ser Cys Lys Ala Ser Gly Asn Thr Ser Tyr Trp Ile
20 25 30

Asn Trp Val Arg Gln Ala Thr Gly Gln Gly Leu Glu Trp Met Gly Arg
35 40 45

Ile Asp Pro Gly Gly Gly Ser Thr Gly Tyr Ala Gln Lys Phe Gln Gly

```
    50                  55                  60

Arg Val Thr Met Thr Arg Asp Thr Ser Ile Ser Thr Ala Tyr Met Glu
65                  70                  75                  80

Leu Ser Ser Leu Arg Ser Glu Asp Thr Ala Val Tyr Tyr Cys Ala Ser
                85                  90                  95

Tyr Tyr Tyr Ala Met Ala Tyr Trp Gly Gln Gly Thr Leu Val Thr Val
            100                 105                 110

Ser Ser Gly Gly Gly Ser Gly Gly Gly Ser Gly Gly Gly Ser Asp Val
        115                 120                 125

Val Met Thr Gln Ser Pro Leu Ser Leu Pro Val Thr Pro Gly Glu Pro
    130                 135                 140

Ala Ser Ile Ser Cys Arg Ser Ser Gln Ser Ile Val His Ser Asn Gly
145                 150                 155                 160

Asn Thr Tyr Leu Asp Trp Tyr Leu Gln Lys Pro Gly Gln Ser Pro Gln
                165                 170                 175

Leu Leu Ile Tyr Lys Val Ser Asn Arg Ala Ser Gly Val Pro Asp Arg
            180                 185                 190

Phe Ser Gly Ser Gly Ser Gly Thr Asp Phe Thr Leu Lys Ile Ser Arg
        195                 200                 205

Val Glu Ala Glu Asp Val Gly Val Tyr Tyr Cys Phe Gln Gly Ser His
    210                 215                 220

Val Pro Trp Thr Phe Gly Gly Gly Thr Lys Val Glu Ile Lys
225                 230                 235


<210> SEQ ID NO 40
<211> LENGTH: 444
<212> TYPE: PRT
<213> ORGANISM: Artificial Sequence
<220> FEATURE:
<223> OTHER INFORMATION: Engineered Antibody Sequence, IgG1 Heavy Chain

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Ser Tyr Trp Ile
            20                  25                  30

Asn Trp Val Arg Gln Ala Thr Gly Gln Gly Leu Glu Trp Met Gly Arg
        35                  40                  45

Ile Asp Pro Gly Gly Gly Ser Thr Gly Tyr Ala Gln Lys Phe Gln Gly
    50                  55                  60

Arg Val Thr Met Thr Arg Asn Thr Ser Ile Ser Thr Ala Tyr Met Glu
65                  70                  75                  80

Leu Ser Ser Leu Arg Ser Glu Asp Thr Ala Val Tyr Tyr Cys Ala Ser
                85                  90                  95

Tyr Tyr Tyr Ala Met Ala Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
```

```
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440


<210> SEQ ID NO 41
<211> LENGTH: 444
<212> TYPE: PRT
<213> ORGANISM: Artificial Sequence
<220> FEATURE:
<223> OTHER INFORMATION: Engineered Antibody Sequence, IgG1 Heavy Chain

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Ser Tyr Trp Ile
            20                  25                  30

Asn Trp Val Arg Gln Ala Thr Gly Gln Gly Leu Glu Trp Met Gly Arg
        35                  40                  45

Ile Asp Pro Gly Gly Gly Ser Thr Gly Tyr Ala Gln Lys Phe Gln Gly
    50                  55                  60

Arg Val Thr Met Thr Arg Asp Thr Ser Ile Ser Thr Ala Tyr Met Glu
65                  70                  75                  80

Leu Ser Ser Leu Arg Ser Glu Asp Thr Ala Val Tyr Tyr Cys Ala Ser
                85                  90                  95

Tyr Tyr Tyr Ala Met Ala Tyr Trp Gly Gln Gly Thr Leu Val Thr Val
```

```
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 42
<211> LENGTH: 219
<212> TYPE: PRT
<213> ORGANISM: Artificial Sequence
<220> FEATURE:
<223> OTHER INFORMATION: Engineered Antibody Sequence, Light Chain

<400> SEQUENCE: 42

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
```

-continued

```
            20                  25                  30

Asn Gly Asn Thr Tyr Leu Asp Trp Tyr Leu Gln Lys Pro Gly Gln Ser
        35                  40                  45

Pro Gln Leu Leu Ile Tyr Lys Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```